United States Patent
Vaka et al.

(10) Patent No.: US 11,547,670 B2
(45) Date of Patent: *Jan. 10, 2023

(54) DELAYED RELEASE METHYLPHENIDATE COMPOSITIONS

(71) Applicant: Amneal Complex Products Research LLC, Bridgewater, NJ (US)

(72) Inventors: Siva Ram Kiran Vaka, Piscataway, NJ (US); Atsawin Thongsukmak, Basking Ridge, NJ (US); Jaydeep Vaghashiya, Franklin Park, NJ (US); Dipen Desai, Whippany, NJ (US); Navnit H. Shah, Monmouth Junction, NJ (US); Wantanee Phuapradit, Lewes, DE (US); Paras Jariwala, Somerset, NJ (US)

(73) Assignee: Amneal Complex Products Research LLC, Bridgewater, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/431,868

(22) PCT Filed: Mar. 5, 2020

(86) PCT No.: PCT/US2020/021250
§ 371 (c)(1),
(2) Date: Aug. 18, 2021

(87) PCT Pub. No.: WO2020/181127
PCT Pub. Date: Sep. 10, 2020

(65) Prior Publication Data
US 2022/0133635 A1    May 5, 2022

Related U.S. Application Data

(60) Provisional application No. 62/814,237, filed on Mar. 5, 2019, provisional application No. 62/872,492, filed on Jul. 10, 2019.

(51) Int. Cl.
| A61K 9/24 | (2006.01) |
| A61K 9/20 | (2006.01) |
| A61K 31/165 | (2006.01) |
| A61K 31/4402 | (2006.01) |

(52) U.S. Cl.
CPC ............ *A61K 9/2086* (2013.01); *A61K 9/205* (2013.01); *A61K 9/2027* (2013.01); *A61K 9/2031* (2013.01); *A61K 31/165* (2013.01); *A61K 31/4402* (2013.01)

(58) Field of Classification Search
None
See application file for complete search history.

(56) References Cited

U.S. PATENT DOCUMENTS

| 5,156,850 A | 10/1992 | Wong et al. | |
| 6,368,626 B1 * | 4/2002 | Bhatt | A61K 9/0004 514/774 |
| 7,521,067 B1 | 4/2009 | Greerke et al. | |
| 2001/0012847 A1 | 8/2001 | Lam et al. | |
| 2010/0112052 A1 | 5/2010 | Chen et al. | |
| 2010/0260844 A1 * | 10/2010 | Scicinski | A61K 9/1617 424/484 |

FOREIGN PATENT DOCUMENTS

| EP | 0768867 | 4/1997 |
| WO | WO 99/62496 | 12/1999 |

OTHER PUBLICATIONS

Kurlan R, et al., Clonidine and methylphenidate were effective for attention deficit hyperactivity disorder in children with comorbid tics, Evidence-based medicine, BMJ Group, UK, US, vol. 7, No. 5, Sep. 1, 2002, p. 157 XP002724188, ISSN: 1356-5524, DOI: 10.1136/EBM.7.5.157.
Robinson, et al., The osmotic coefficients of some organic compounds in relation to their chemical constitution, Trans. Faraday Soc., vol. 38, Jan. 1, 1942, pp. 63-70, XP5589305, Figure 1, table V.
International Search Report.

* cited by examiner

*Primary Examiner* — Susan T Tran
(74) *Attorney, Agent, or Firm* — Amneal Complex Products Research LLC; Vandana Awasthi

(57) ABSTRACT

The present disclosure provides programmable osmotic-controlled oral compositions providing delayed extended release of a therapeutically acceptable amount of methylphenidate hydrochloride. The programmable osmotic-controlled compositions of the disclosure provide a lag time that is independent of the presence or absence of food, type of food, pH, gastric emptying, and volume of gastric fluid. The compositions of the disclosure can be programmed to provide a desired and precise lag time, and release drug, after the lag time, at a rhythm that matches the circadian rhythm of an individual being treated to optimize therapeutic outcome and minimize side effects.

18 Claims, 27 Drawing Sheets

DELAYED RELEASE METHYLPHENIDATE COMPOSITIONS

1. RELATED APPLICATIONS

Figure 1:
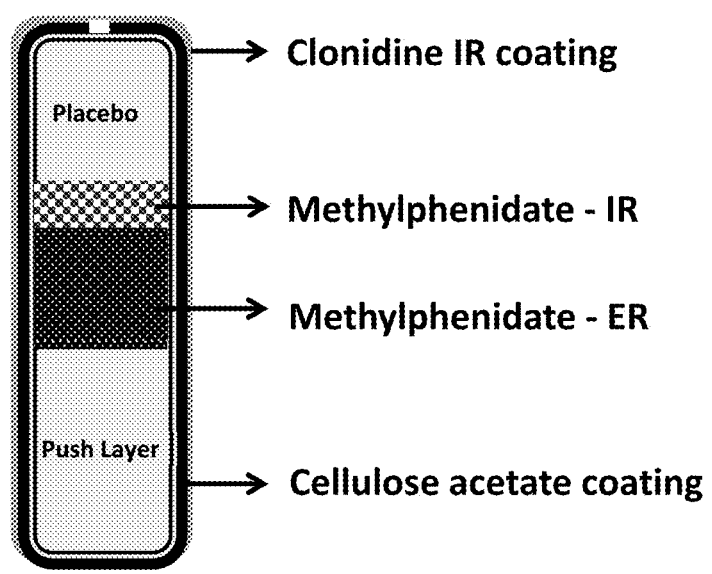

This application is a U.S. National Stage Patent Application under 35 U.S.C. § 371 of International Application No. PCT/US2020/021250, filed on Mar. 5, 2020, which claims priority to U.S. Provisional Patent Application Nos. 62/814,237, filed Mar. 5, 2019, and 62/872,492, filed Jul. 10, 2019, the disclosures of which are hereby incorporated by reference in their entireties.

2. TECHNICAL FIELD

The presently disclosed subject matter relates to therapeutic compositions and methods for the treatment of attention deficit disorder (ADD), or attention deficit hyperactivity disorder (ADHD). The present disclosure relates to programmable osmotic-controlled oral compositions providing delayed controlled release of stimulants, e.g., methylphenidate or pharmaceutically acceptable salts thereof, and mixed amphetamines. The osmotic-controlled oral compositions of the disclosure can be programmed to provide a desired and precise lag time, and a desired release profile after the lag time to provide therapeutic plasma concentrations of stimulants, e.g., methylphenidate or pharmaceutically acceptable salts thereof, even while releasing the drugs in the lower portions of the GI tract. The compositions of the disclosure provide a precise lag time that is substantially independent of the presence or absence of food, type of food, pH, gastric emptying time, and volume and viscosity of immediate microenvironment of drug release.

3. BACKGROUND

Attention deficit hyperactivity disorder (ADHD) and attention deficit disorder (ADD) are two of the most common developmental disorders in children which are characterized by symptoms such as impulsiveness, hyperactivity, and inattentiveness. Hyperactivity is particularly common in children with ADHD. Treatment of these disorders include various stimulate medications. Methylphenidate hydrochloride, and mixed amphetamines are among stimulants that have been approved by FDA. However, treatment of ADHD/ADD, as well as other stimulant-responsive conditions provides challenges associated with delivering and maintaining an effective stimulant concentration in patients, particularly children, throughout the day. This is particularly important during the morning hours when cognitive abilities and concentration are needed for school or work, and during the late afternoon or evening when students often do homework. Furthermore, parents and caregivers of children suffering from ADHD/ADD often experience early morning symptom control as a major obstacle for getting the children ready for school.

Stimulant-based medications are typically dosed two hours prior to beginning an early morning routine, with an onset of treatment effect usually about two hours after administration. Such medications require twice-daily administration and cause compliance issues. Commercially available products of methylphenidate have been approved by the FDA for the treatment of ADHD in patients six years and older. Certain methylphenidate formulations are administered in the evening in an attempt to improve ADHD symptoms in the early morning and throughout the day. However, drug release from formulations can be affected by pH, food, and gastric transit time, with a potential for variable drug release during the night and early morning leading to insomnia.

There remains a need to develop compositions that can be programmed to control attention disorders, which improve symptoms in the early morning and throughout the day, without the potential for variable drug release during the night and early morning, leading to insomnia. In particular, there remains a need to develop extended release methylphenidate compositions that can be taken, in the evening or before bed time, with or without food, to delay the release of methylphenidate by at least about 6 hours with minimal inter-subject variability, independent of pH, viscosity, and GI transit time, to control symptoms of attention disorder in the early morning and throughout the day.

The present disclosure addresses the unmet needs by providing osmotic-controlled, oral, delayed-release methylphenidate compositions that can improve the symptoms of ADHD/ADD in the early morning and throughout the day, without the need for early morning dosing that requires an onset time of about two hours. The compositions of the disclosure provide a precise lag time, with minimal variability in drug release, independent of the presence or absence of food, type of food, pH, gastric emptying, gastric transit time, and volume of fluid in the immediate microenvironment of drug release. In particular, the disclosure provides desired drug bioavailability while releasing the drug in lower portions of the GI tract, e.g., in the colon in a viscous alkaline microenvironment.

4. SUMMARY

The purpose and advantages of the disclosed subject matter will be set forth and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these advantages and in accordance with the purpose of the disclosed subject matter, as embodied and broadly described subject matter includes an osmotic-controlled oral pharmaceutical composition providing delayed extended release of a therapeutically effective amount of methylphenidate or a pharmaceutically acceptable salt thereof, the composition including a multilayer core including an active layer sandwiched between a placebo layer and a push layer, wherein the placebo layer includes at least one wicking agent and/or an osmogen, and at least one polyethylene oxide polymer having an average molecular weight of from about 300,000 Da to about 900,000 Da; the active layer includes a methylphenidate or a pharmaceutically acceptable salt thereof, a wicking agent, and at least one polyethylene oxide polymer having a molecular weight of from about 100,000 Da to about 300,000 Da; the push layer includes at least one polyethylene oxide polymer having an average molecular weight of greater than or equal to 1,000,000 Da, and at least one osmogen; and a semipermeable membrane surrounding the multilayer core, wherein the semipermeable membrane is present in an amount of from about 5 wt % to about 15 wt % coating weight gain, based on the total weight of the multilayer core. In certain embodiments, the semipermeable membrane includes at least one orifice facing the placebo layer. In certain embodiments, the orifice has an optimum orifice diameter of from about 0.6 mm to about 2.0 mm. In certain embodiments, the placebo layer is present in an amount of from about 25 wt % to about 50 wt %, based on the total weight of the multilayer core. In certain embodiments, the active layer is substantially free of sodium chloride, and includes methylphenidate or a salt thereof: polyethylene oxide polymer in a ratio of between about 20:80 and about 70:30 by weight. In certain embodiments, the osmogen in the push layer is present in an amount of from about10 w % to about 30 wt %, based on total weight of the push layer.

In certain embodiments, the composition provides a lag time of at least about 6 hours, during which the composition releases no more than 10 wt % of the methylphenidate or a pharmaceutically acceptable salt thereof, followed by extended release of the methylphenidate or a pharmaceutically acceptable salt thereof for about 10 hours to about 12 hours.

In certain embodiments, the composition exhibits not more than 30% variability in the lag time with variations in pH, viscosity, and volume of a dissolution medium. In certain embodiments, the composition of claim 1, wherein the lag time does not depend upon gastric motility and presence of food in the GI tract.

In certain embodiments, the semipermeable membrane includes a pH-independent water-insoluble polymer and a pH-independent pore former at a polymer to pore former ratio of between about 80:20 and about 99.5:0.5 by weight.

In certain embodiments, the semipermeable membrane includes a pH-independent water-insoluble polymer and a pH-independent pore former at a polymer to pore former ratio of between about 90:10 and about 95:5 by weight.

In certain embodiments, the pH-independent water-insoluble polymer is selected from the group consisting of cellulose acetate, cellulose acetate butyrate, and cellulose triacetate.

In certain embodiments, the pH-independent pore former is selected from the group consisting of polyethylene glycol, hydroxypropyl cellulose, polyvinyl pyrolidone, polyvinyl acetate, mannitol, and methyl cellulose, poloxamer, triethyl citrate, triacetin, hydroxypropyl methylcellulose, glycerol, and combinations thereof.

In certain embodiments, the semipermeable membrane further includes at least one plasticizer selected from the group consisting of polyethylene glycols, triethyl citrate, triacetin, diethyl tartrate, dibutyl sebacate, and combinations thereof.

In certain embodiments, the polyethylene oxide polymer in the placebo layer has an average molecular weight of about 300,000 Da, about 600,000 Da, about 900,000 Da, or intermediate values therein.

In certain embodiments, the polyethylene oxide polymer in the placebo layer has an average molecular weight of about 600,000 Da.

In certain embodiments, the polyethylene oxide polymer in the active layer has an average molecular weight of about 200,000 Da.

In certain embodiments, the active layer includes methylphenidate or a salt thereof: polyethylene oxide polymer in a ratio of about 70:30 by weight.

14. The composition of claim 1, wherein the polyethylene oxide polymer in the push layer has an average molecular weight of about 1000,000 Da, about 2000,000 Da, about 4000,000 Da, about 5000,000 Da, or about 7000,000 Da.

In certain embodiments, the placebo layer includes at least one wicking agent selected from the group consisting of croscarmellose sodium, calcium carboxymethyl cellulose, crospovidone, low-substituted hydroxypropyl celluloses, sodium starch glycolate, colloidal silicon dioxide, alginic acid and alginates, acrylic acid derivatives, and various starches.

In certain embodiments, the placebo layer includes an osmogen selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, or combinations thereof.

In certain embodiments, the placebo layer includes a wicking agent and an osmogen, wherein the wicking agent is crospovidone the osmogen is sodium chloride.

In certain embodiments, the wicking agent in the active layer is crospovidone.

In certain embodiments, at least one of the placebo layer, the active layer, and the push layer further includes a stabilizer selected from the group consisting of ascorbic acid, succinic acid, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof.

In certain embodiments, the composition further includes an immediate release layer containing a sedative, wherein the immediate release layer is placed over the semipermeable membrane.

In certain embodiments, the sedative is selected from the group consisting of clonidine, guanfacine, diphenhydramine, and melatonin, or pharmaceutically acceptable salts thereof.

In certain embodiments, the present disclosure provides an osmotic-controlled oral pharmaceutical composition providing an immediate release of a sedative and a delayed extended release of a therapeutically effective amount of methylphenidate or a pharmaceutically acceptable salt thereof, the composition including a multilayer core includes an active layer sandwiched between a placebo layer and a push layer, wherein the placebo layer includes at least one wicking agent and/or an osmogen, and at least one polyethylene oxide polymer having an average molecular weight of from about 300,000 Da to about 900,000 Da, the active layer includes a methylphenidate or a pharmaceutically acceptable salt thereof, a wicking agent, and at least one polyethylene oxide polymer having a molecular weight of from about 100,000 Da to about 300,000 Da, the push layer includes at least one polyethylene oxide polymer having an average molecular weight of greater than or equal to 1000,000 Da, and at least one osmogen; a semipermeable membrane surrounding the multilayer core; and an immediate release drug layer over the semipermeable membrane. In certain embodiments, the semipermeable membrane is present in an amount of from about 5 wt % to about 15 wt % coating weight gain, based on the total weight of the multilayer core. In certain embodiments, the semipermeable membrane includes at least one orifice facing the placebo layer. In certain embodiments, the orifice includes an optimum orifice diameter of from about 0.6 mm to about 2.0 mm. In certain embodiments, the immediate release drug layer includes a sedative for immediate release. In certain embodiments, the placebo layer is present in an amount of from about 25 wt % to about 50 wt %, based on the total weight of the multilayer core. In certain embodiments, the active layer is substantially free of sodium chloride, and includes methylphenidate or a salt thereof: polyethylene oxide polymer in a ratio of between about 20:80 and about 70:30 by weight. In certain embodiments, the osmogen in the push layer is present in an amount of from about 10 w % to about 30 wt %, based on total weight of the push layer.

In certain embodiments, the composition provides an immediate release of a sedative followed by a lag time of at least about 6 hours during which the composition releases no more than 10% of methylphenidate or a salt thereof, followed by delayed extended release of methylphenidate or a salt thereof.

In certain embodiments, the present disclosure provides a method for treating ADHD in a subject, the method includes orally administering to the subject an osmotic-controlled oral pharmaceutical composition providing delayed extended release of a therapeutically effective amount of methylphenidate or a pharmaceutically acceptable salt thereof, the composition includes a multilayer core includes an active layer sandwiched between a placebo layer and a push layer, wherein the placebo layer includes at least one wicking agent and/or an osmogen, and at least one polyethylene oxide polymer having an average molecular weight of from about 300,000 Da to about 900,000 Da, the active layer includes a methylphenidate or a pharmaceutically acceptable salt thereof, a wicking agent, and at least one polyethylene oxide polymer having a molecular weight of from about 100,000 Da to about 300,000 Da, the push layer includes at least one polyethylene oxide polymer having an average molecular weight of greater than or equal to 1000,000 Da, and at least one osmogen; and a semipermeable membrane surrounding the multilayer core. In certain embodiments, the semipermeable membrane is present in an amount of from about 5 wt % to about 15 wt % coating weight gain, based on the total weight of the multilayer core. In certain embodiments, the semipermeable membrane includes at least one orifice facing the placebo layer. In certain embodiments, the orifice includes an optimum orifice diameter of from about 0.6 mm to about 2.0 mm. In certain embodiments, the placebo layer is present in an amount of from about 25 wt % to about 50 wt %, based on the total weight of the multilayer core. In certain embodiments, the active layer is substantially free of sodium chloride, and includes methylphenidate or a salt thereof: polyethylene oxide polymer in a ratio of between about 20:80 and about 70:30 by weight. In certain embodiments, the osmogen in the push layer is present in an amount of from about 10 w % to about 30 wt %, based on total weight of the push layer.

5. BRIEF DESCRIPTION OF THE DRAWINGS

The subject matter will be more readily understood from the following detailed description when read in conjunction with the accompanying drawings in which:

FIG. 1 depicts a cross-section view of a four-layer osmotic dosage form comprising an IR clonidine coating; a cellulose acetate coating containing an orifice, placed below the clonidine IR coating; a placebo layer facing the orifice; a delayed immediate release layer, containing methylphenidate or a pharmaceutically acceptable salt thereof, placed below the placebo layer; a delayed extended release layer, containing methylphenidate or a pharmaceutically acceptable salt thereof, placed below the delayed immediate release layer; and a push layer placed below the delayed extended release layer.

Figure 2:
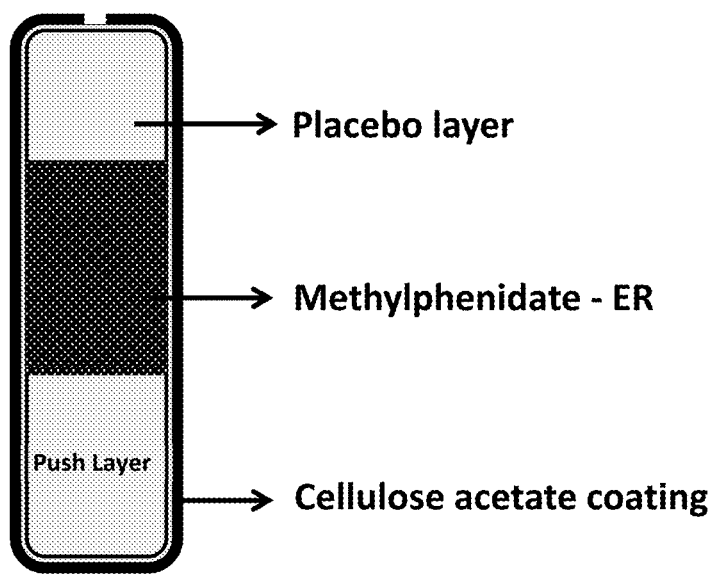

FIG. 2 depicts a cross-section view of a three-layer osmotic dosage form comprising a cellulose acetate coating containing an orifice; a placebo layer facing the orifice; a delayed extended release layer, containing methylphenidate or a pharmaceutically acceptable salt thereof, placed below the placebo layer; and a push layer placed below the delayed extended release layer.

Figure 3:
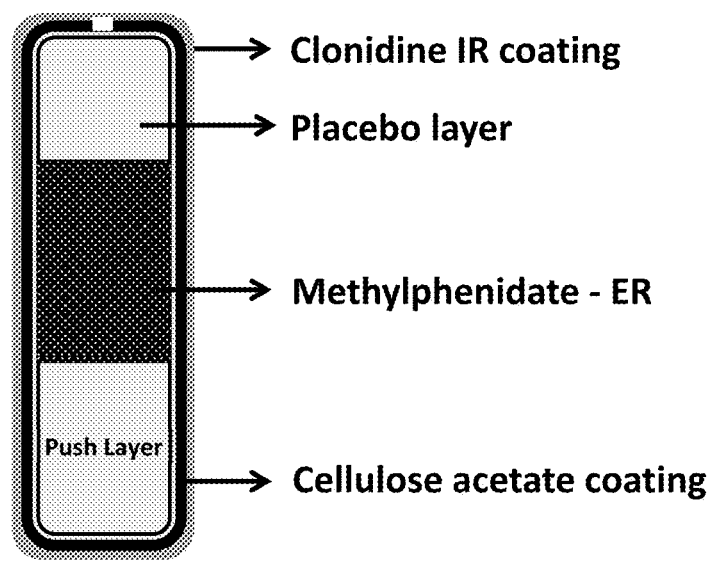

FIG. 3 depicts a cross-section view of a three-layer osmotic dosage form comprising an IR clonidine coating; a cellulose acetate coating containing an orifice, placed below the clonidine IR coating; a placebo layer facing the orifice; a delayed extended release layer containing methylphenidate or a pharmaceutically acceptable salt thereof, placed below the placebo layer; and a push layer placed below the delayed extended release layer.

Figure 4:
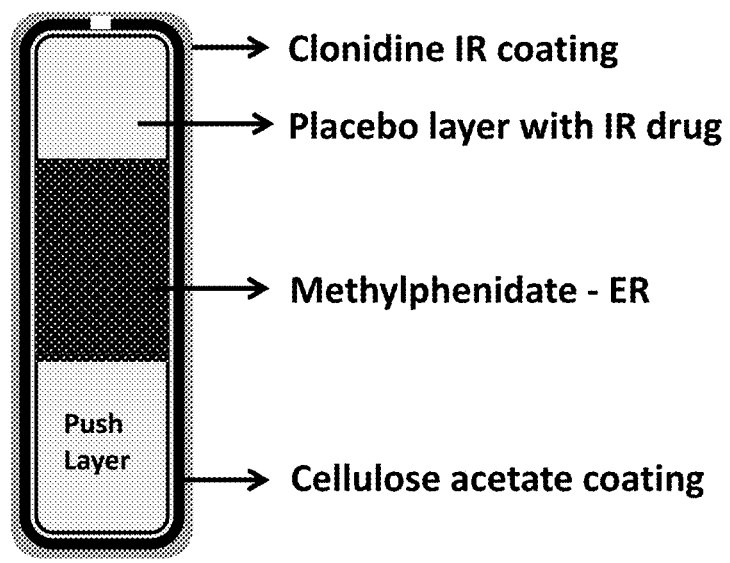

FIG. 4 depicts a cross-section view of a three-layer osmotic dosage form comprising an IR clonidine coating; a cellulose acetate coating containing an orifice, placed below the clonidine IR coating; a placebo layer containing small amounts of a drug for immediate release and facing the orifice; a delayed extended release layer, containing methylphenidate or a pharmaceutically acceptable salt thereof, placed below the placebo layer; and a push layer placed below the delayed extended release layer.

Figure 5:
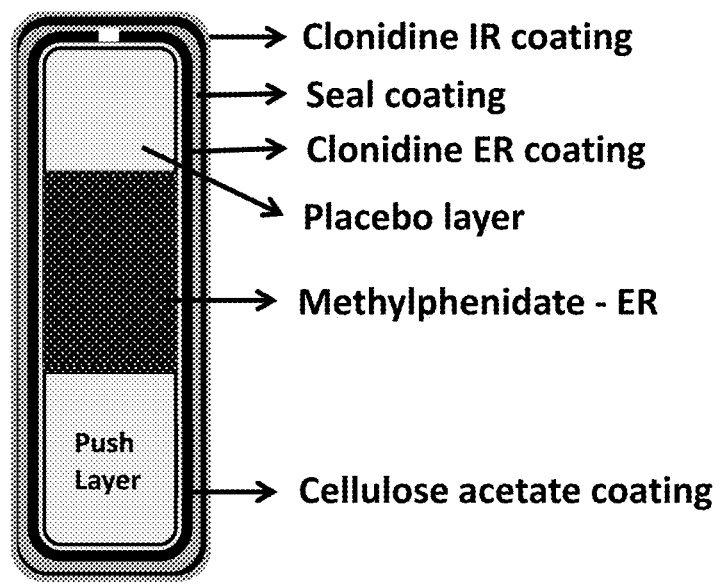

FIG. 5 depicts a cross-section view of a three-layer osmotic dosage form comprising an IR clonidine coating; a seal coating below the IR clonidine coating; a clonidine ER coating below the seal coating; a cellulose acetate coating containing an orifice, placed below the ER clonidine coating; a placebo layer facing the orifice; a delayed extended release layer containing methylphenidate or a pharmaceutically acceptable salt thereof, placed below the placebo layer; and a push layer placed below the delayed extended release layer.

Figure 6:
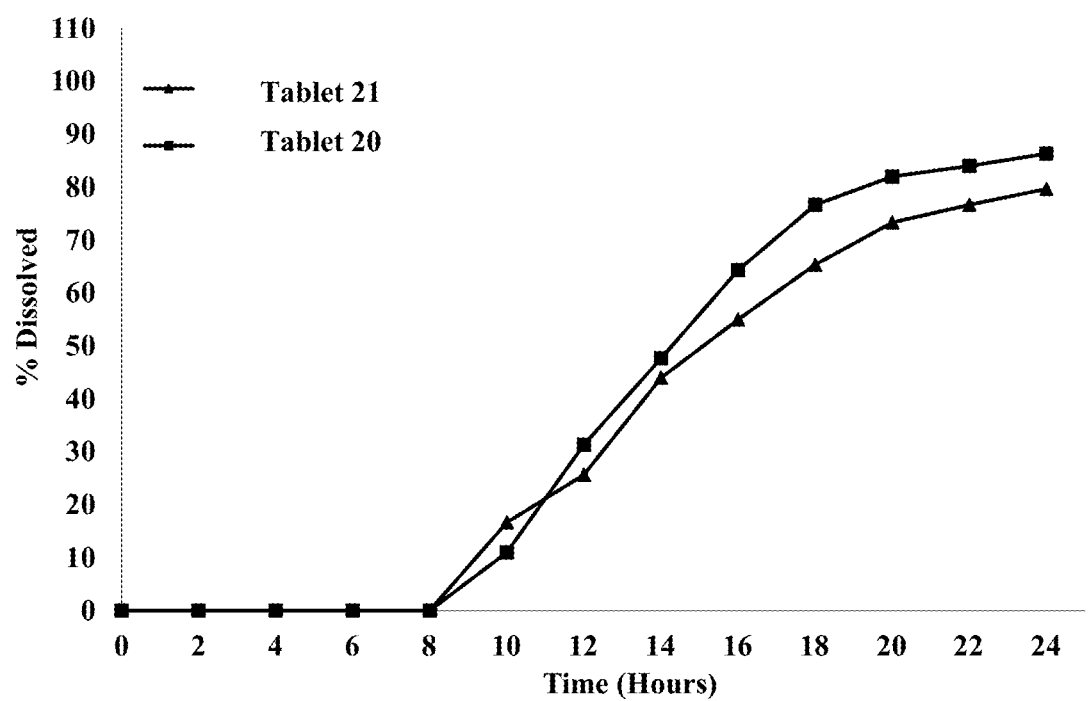

FIG. 6 shows the effect of the amount of POLYOX® present in the placebo layer on dissolution profile of the tablet placed in about 900 ml of about 0.01N HCl, using USP II (sinkers) at about 50 rpm and about 37° C. Placebo layer in Tablet 20 contained about 150 mg of POLYOX® WSR 1105. Placebo layer in Tablet 21 contained about 75 mg of POLYOX® WSR 1105. Percent drug dissolved was plotted over time (hours). FIG. 6 demonstrates that Tablet 20 exhibits higher dissolution rate and higher drug recovery compared to Tablet 21. FIG. 6 further demonstrates that the POLYOX® WSR 1105 amount in the placebo layer does not affect lag time.

Figure 7:
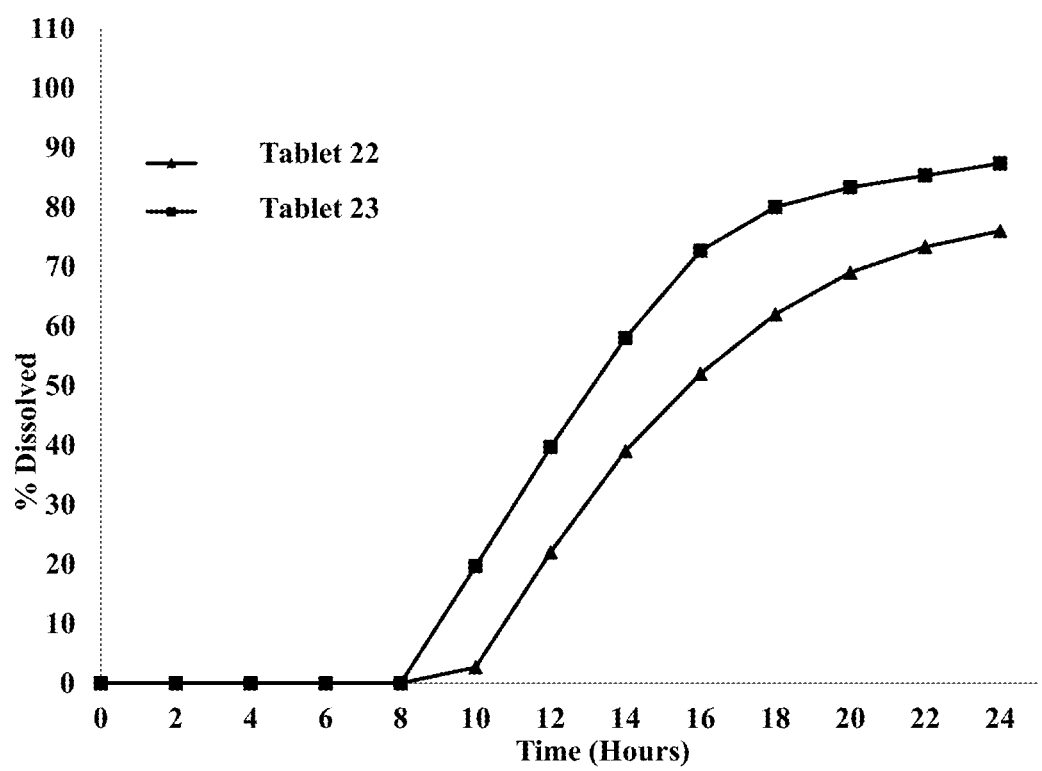

FIG. 7 shows the effect of drug to polymer weight ratio in the active layer on dissolution profiles of the tablets placed in about 900 ml of about 0.01N HCl, using USP II (sinkers) at 50 rpm and 37° C. Active layer in Tablet 22 contained a drug to polymer weight ratio of about 20:80. Active layer in Tablet 23 contained a drug to polymer weight ratio of about 30:70. Percent drug dissolved was plotted over time (hours). FIG. 7 demonstrates that release rate, and drug recovery is improved with increasing drug to polymer weight ratio in the active layer.

Figure 8:
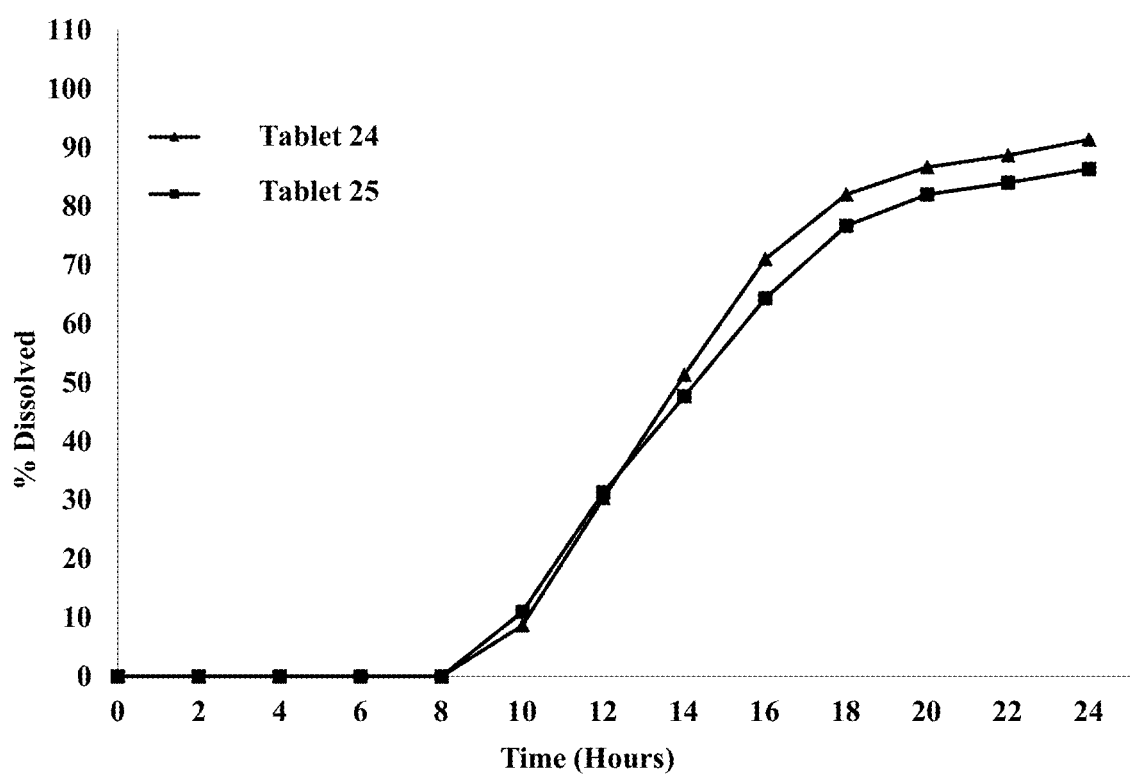

FIG. 8 shows the effect of the presence of sodium chloride in the active layer on dissolution profile of tablets placed in about 900 ml of about 0.01N HCl, using USP II (sinkers) at 50 rpm and 37° C. Tablet 24 contained sodium chloride in the active layer. Tablet 25 did not contain any sodium chloride in the active layer. Percent drug dissolved was plotted over time (hours). FIG. 8 demonstrates that Tablet 24 containing NaCl in the active layer exhibits higher drug recovery compared to Tablet 25 containing no amount of sodium chloride in the active layer.

Figure 9:
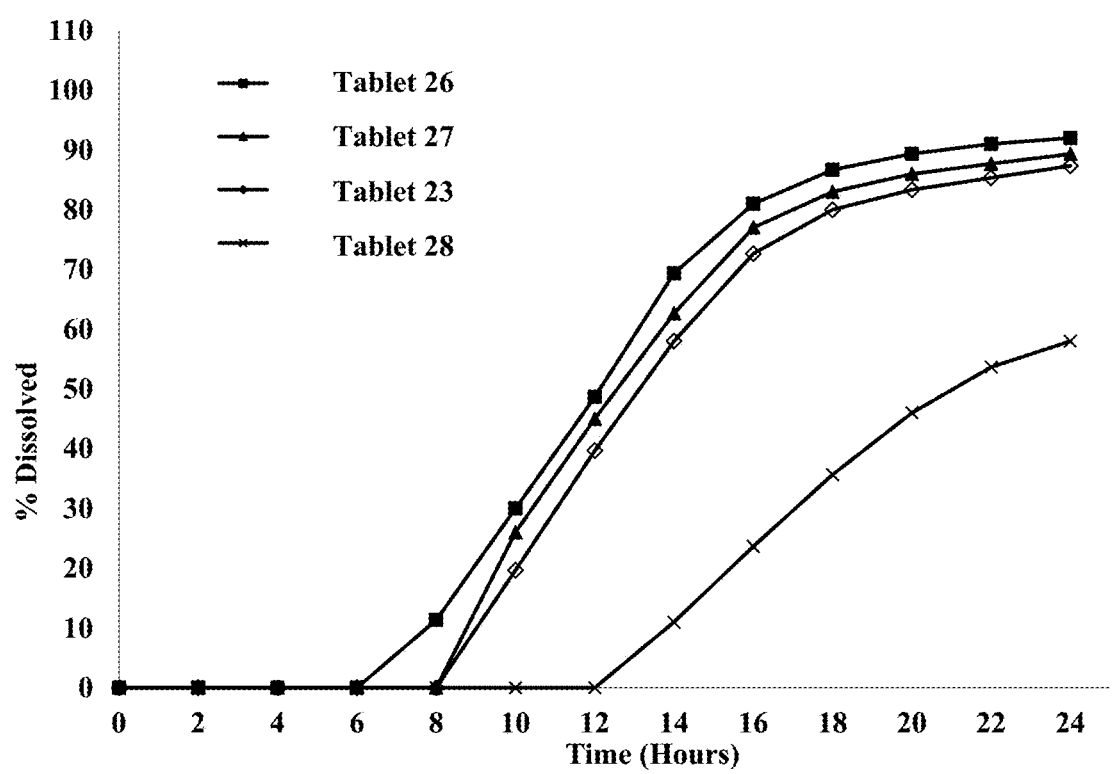

FIG. 9 shows the effect of sodium chloride in the push layer on lag time and drug recovery. FIG. 9 compares dissolution profiles of the tablets 23, 26, 27, and 28 in about 900 ml of about 0.01N HCl, using USP II (sinkers) at 50 rpm and 37° C. Tablet 28 contained no sodium chloride in the push layer; Tablet 23 contained about 10 wt % of sodium chloride, based on the total weight of the push layer; Tablet 27 contained about 18 wt % of sodium chloride, based on the total weight of the push layer; and tablet 26 contained about 25 wt % of sodium chloride, based on the in push layer. Percent drug dissolved was plotted over time (hours). FIG. 9 demonstrates that presence of sodium chloride in push layer reduces lag time and improves release rate and drug recovery, when compared with compositions without any sodium chloride in the push layer. FIG. 9 further demonstrates that increasing the amount of sodium chloride in the push layer reduces lag time.

Figure 10:
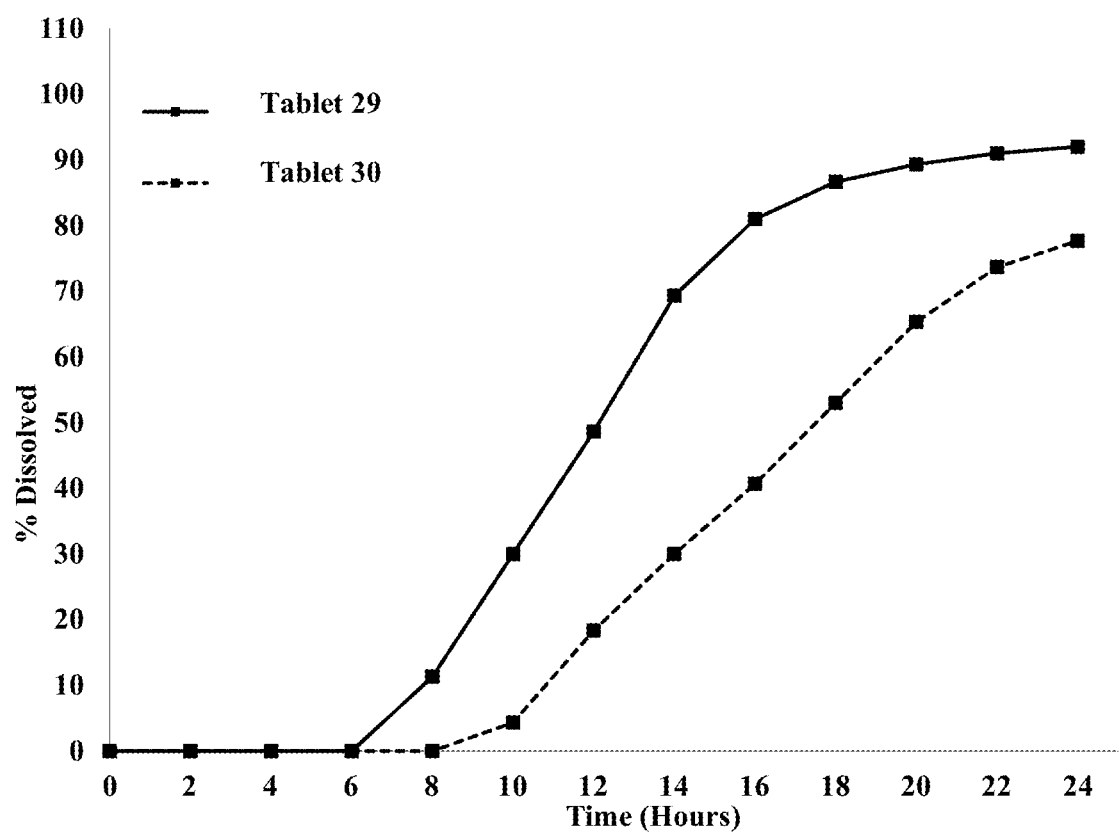

FIG. 10 shows the effect of the cellulose acetate to polyethylene glycol weight ratio in the semipermeable membrane on lag time and drug recovery of the tablets with 15% coating weight gain. FIG. 10 shows comparison of dissolution profiles of tablets 29 and 30 in about 900 ml of about 0.01N HCl, using USP II (sinkers) at 50 rpm and 37° C. Tablet 29 contained OPADRY® CA with CA:PEG ratio of about 95:5; and Tablet 30 contained OPADRY® CA with CA:PEG ratio of about 98:2. Percent drug dissolved was plotted over time (hours). FIG. 10 demonstrates that increasing the amount of cellulose acetate in the membrane, at a same coating weight gain, increases lag time and reduces drug recovery.

Figure 11:
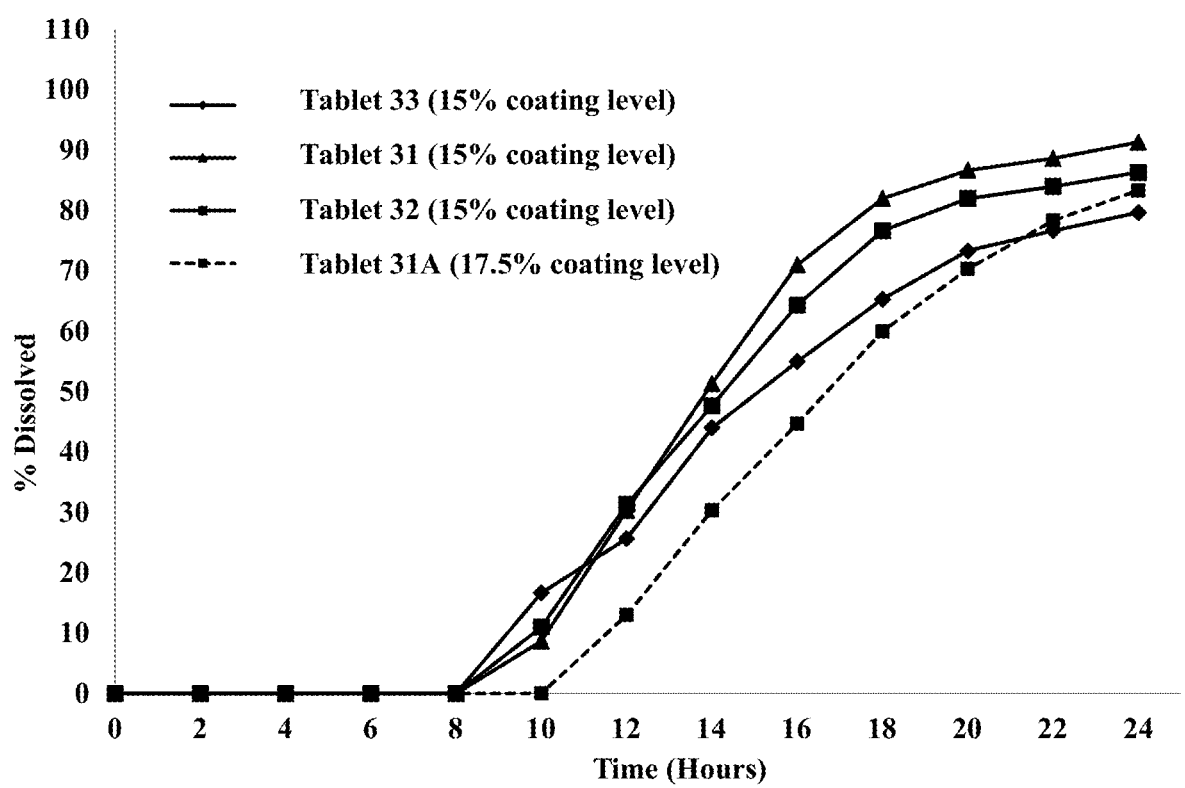

FIG. 11 shows the effect of the presence of sodium chloride in the active layer, and the effect of the coating weight gain/coating level of the semipermeable membrane on lag time and drug recovery. FIG. 11 compares dissolution profiles of Tablets 31, 31A, 32, and 33 in about 900 ml of about 0.01N HCl, using USP II (sinkers) at 50 rpm and 37° C. Percent drug dissolved was plotted over time (hours). FIG. 11 demonstrates that Tablet 31A containing about 17.5 wt % coating weight gain of the functional coat exhibits reduced drug recovery and increased lag time compared to Tablet 31 with about 15 wt % of the coating weight gain. FIG. 11 further compares drug recovery between coated tablets with and without sodium chloride in active layer. FIG. 11 demonstrates that Tablet 31 containing sodium chloride in the active layer, at same coating weight gain, exhibits improved drug recovery compared to Tablets 32 and 33 containing no amount of sodium chloride in the active layer.

Figure 12:
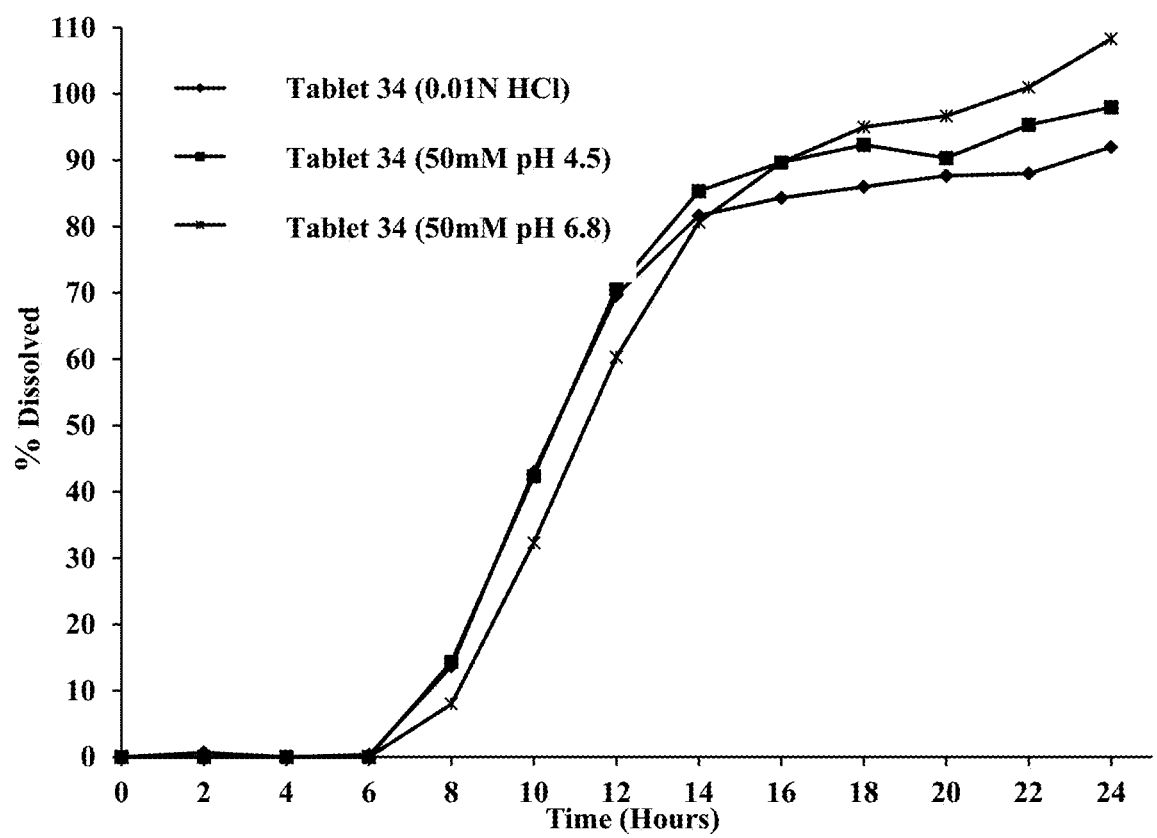

FIG. 12 compares lag time and dissolution profile of a composition of the disclosure in about 900 ml of about 0.01N HCl, pH 4.5 acetate buffer, and pH 6.8 phosphate buffer, using USP II (sinkers) at 50 rpm and 37° C. Percent drug dissolved was plotted over time (hours). FIG. 12 shows effect of pH on lag time in a tablet with a drug to polymer weight ratio of about 30:70. FIG. 12 demonstrates that the tablets exhibit minimal variability in lag time with variations in pH of the dissolution medium.

Figure 13:
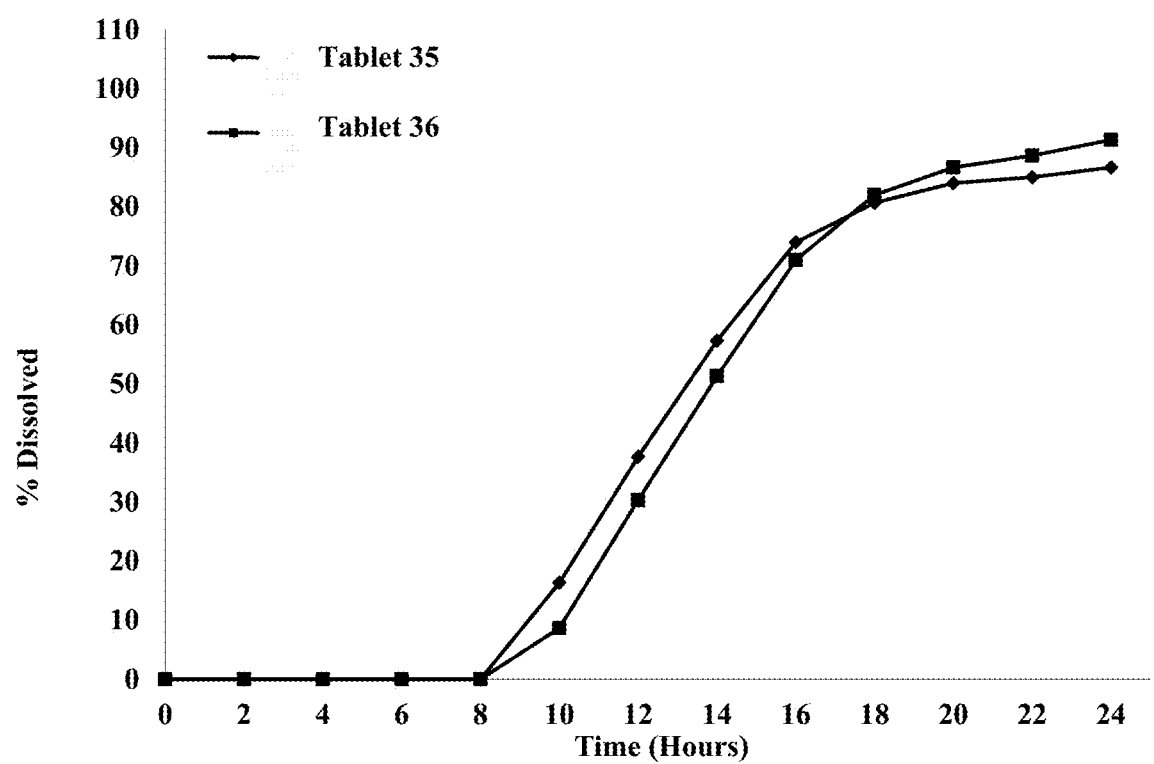

FIG. 13 compares lag time and dissolution profiles of Tablets 35 and 36 in about 900 ml of about 0.01N HCl, using USP II (sinkers) at 50 rpm and 37° C. Tablet 35 contained push layer in an amount of about 102.5 mg; and Tablet 36 contained push layer in an amount of about 120.6 mg. Percent drug dissolved was plotted over time (hours). FIG. 13 shows the effect of push layer amount on lag time in tablets containing POLYOX® 1105 in placebo layer, and containing a drug to polymer weight ratios of about 40:60. FIG. 13 demonstrates that an increase in push layer amount, from 108.5 mg to 120.6 mg, improves drug recovery without affecting the lag time.

Figure 14:
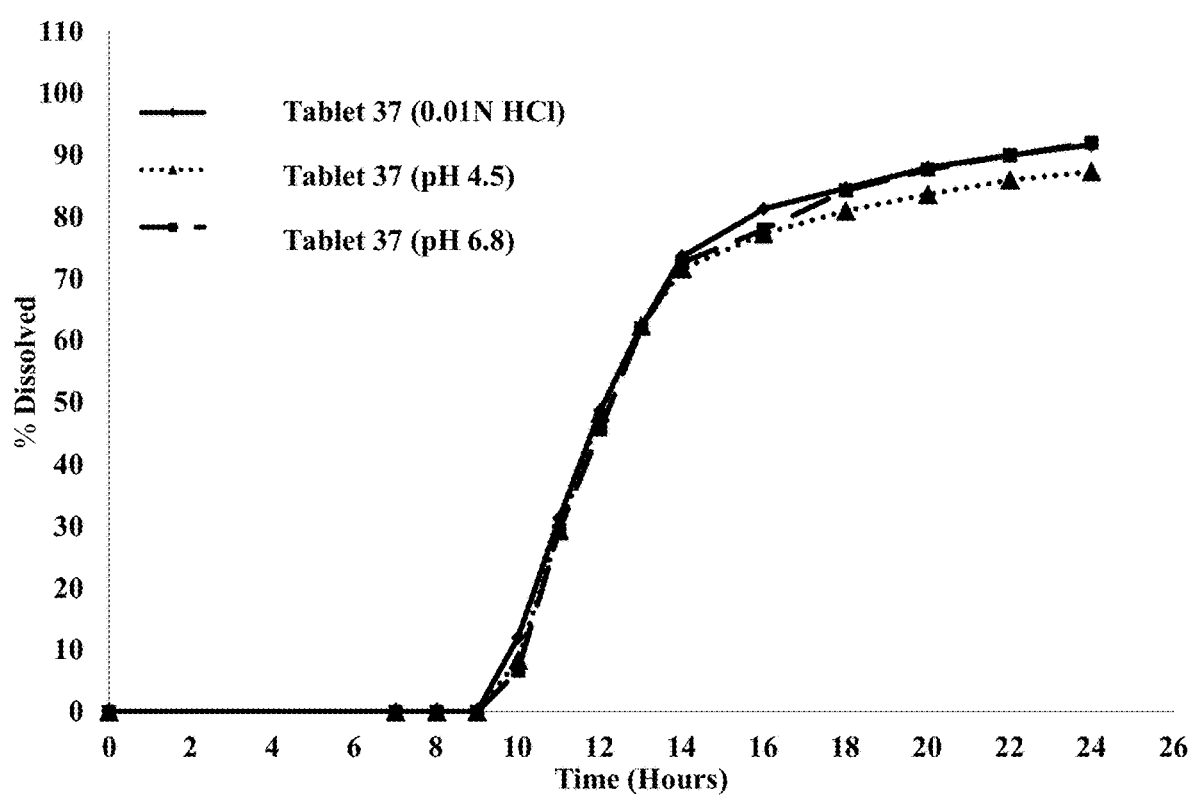

FIG. 14 compares the dissolution profiles of Tablet 37 in about 0.01N HCl, in a pH 4.5 acetate buffer, and in a pH 6.8 phosphate buffer, using USP II (sinkers) at 50 rpm and 37° C. Percent drug dissolved was plotted over time (hours). FIG. 14 demonstrates that Tablet 37 exhibits minimal variability in lag time with variations in pH of the dissolution medium.

Figure 15:
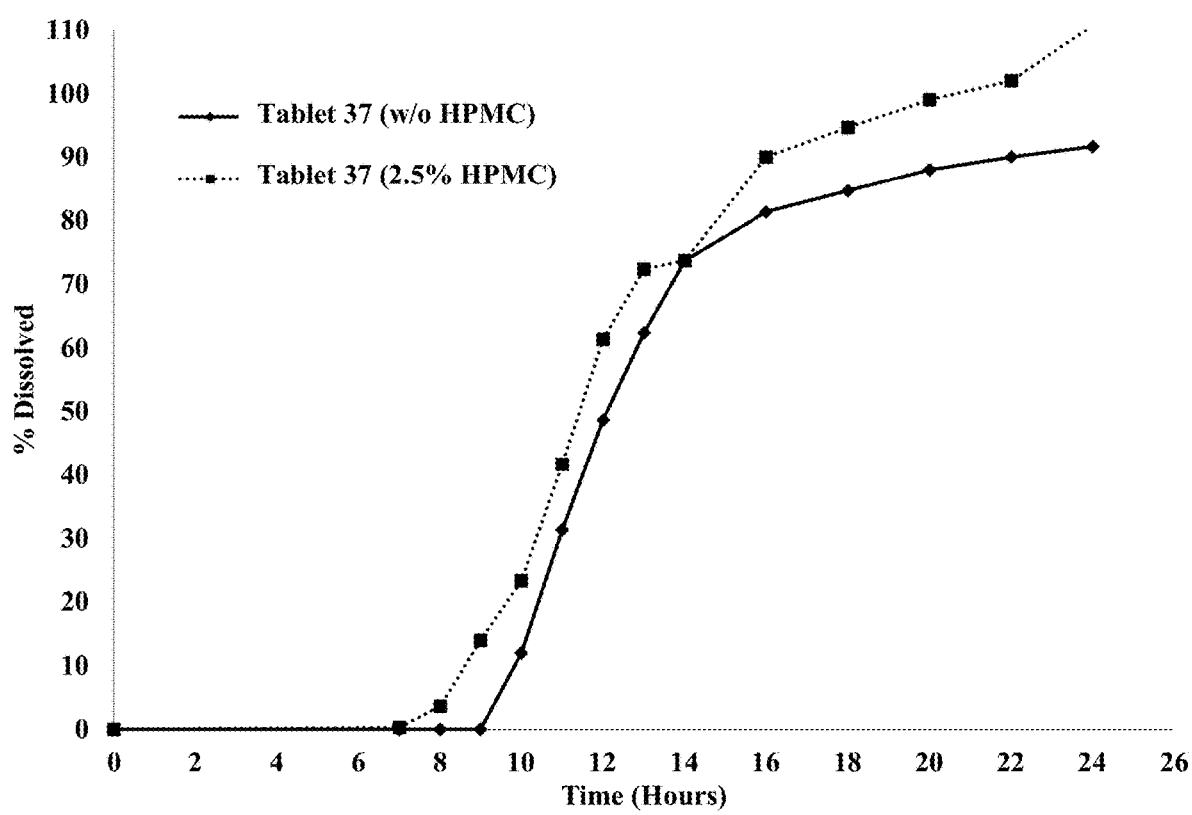

FIG. 15 provides dissolution profiles of Tablet 37 in dissolution mediums with different viscosities, e.g., a dissolution medium containing hydroxypropyl methylcellulose and a dissolution medium without hydroxypropyl methylcellulose, using USP II (sinkers) at 50 rpm and 37° C. Percent drug dissolved was plotted over time (hours). FIG. 15 demonstrates that Tablet 37 exhibits minimal variability in lag time with variations in viscosity of the dissolution medium.

Figure 16:
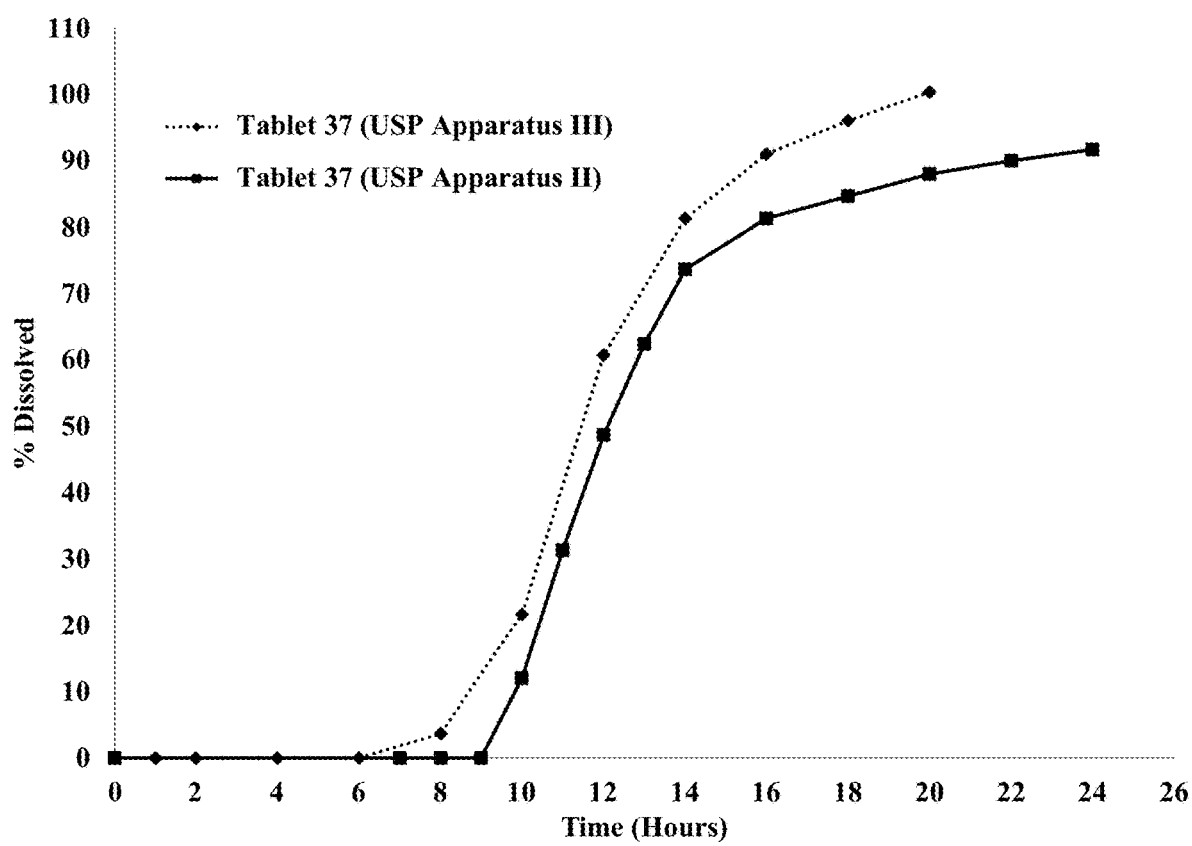

FIG. 16 compares the dissolution profiles of Tablet 37 using USP methods simulating hydrodynamic conditions of the GI tract in about 900ml of about 0.01N HCl, using USP II (sinkers) at 50 rpm and 37° C.; and in about 900 ml of about 0.01N HCl, using USP III (BioDis) at 25 dpm and 37° C. Percent drug dissolved was plotted over time (hours). FIG. 16 demonstrates that there is no substantial change in the lag time with changing hydrodynamics of the dissolution medium.

Figure 17:
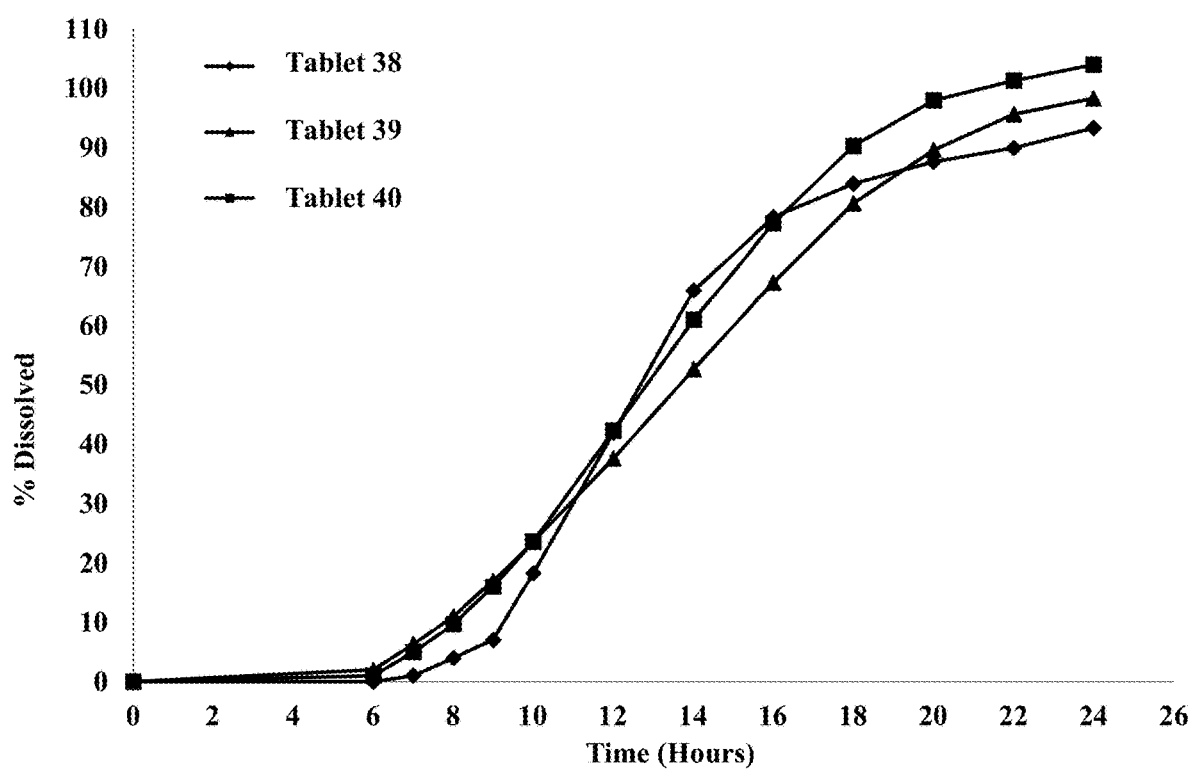

FIG. 17 compares the dissolution profiles of Tablets 38, 39, and 40 in about 900 ml of about 0.01N HCl, using USP II (sinkers) at 50 rpm and 37° C. Tablet 38 contained no sodium chloride in the placebo layer; Tablet 39 contained about 5% sodium chloride in the placebo layer; and Tablet 40 contained about 10% sodium chloride in the placebo layer, based on the total weight of the placebo layer. All the three tablets contained POLYOX® WSR 303 in the push layer. Percent drug dissolved was plotted over time (hours). FIG. 17 demonstrates that the presence and amount of sodium chloride in placebo layer has negligible effect on lag time and release rate.

Figure 18:
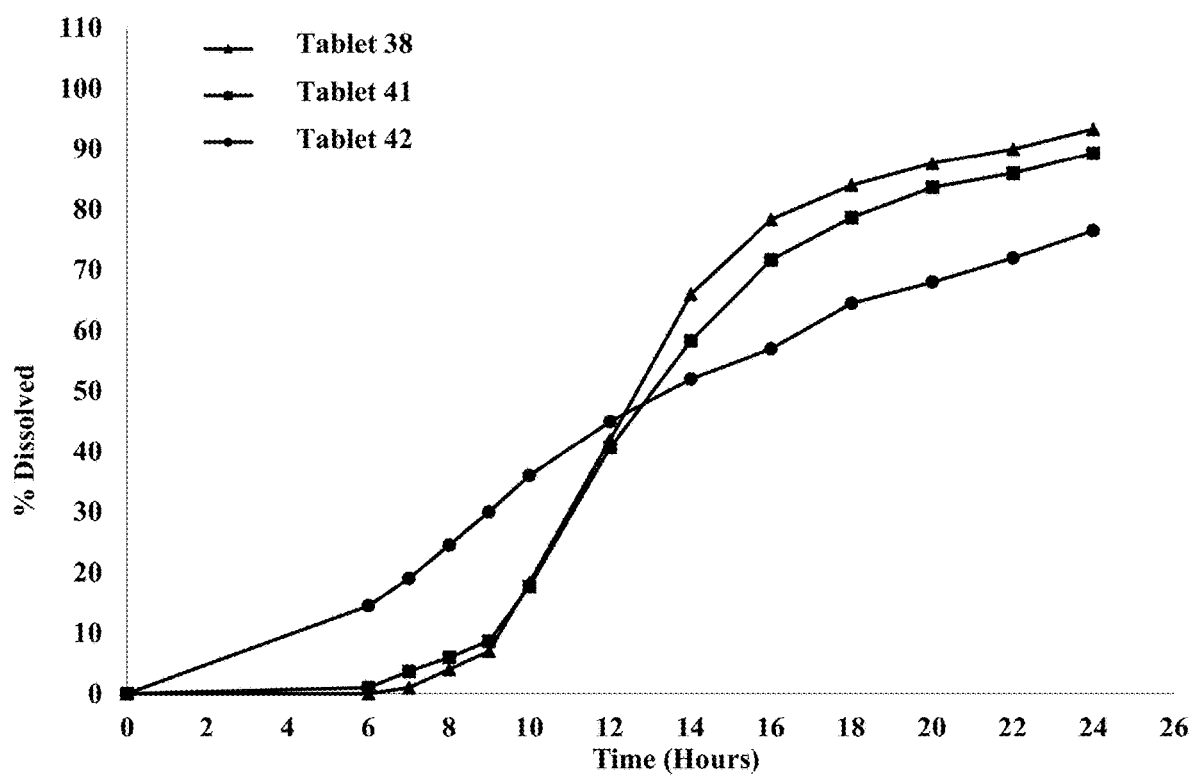

FIG. 18 compares the dissolution profiles of Tablets 38, 41, and 42 in about 900 ml of about 0.01N HCl, using USP II (sinkers) at 50 rpm and 37° C. Tablet 38 contained POLYOX® 1105 in the placebo layer; Tablet 41 contained POLYOX® N80 in the placebo layer; and Tablet 42 contained POLYOX® 750 in the placebo layer. Percent drug dissolved was plotted over time (hours). FIG. 18 demonstrates that average molecular weight of the POLYOX® present in the placebo layer should be at least about 300,000 Da for providing a lag time of at least about 6 hours.

Figure 19:
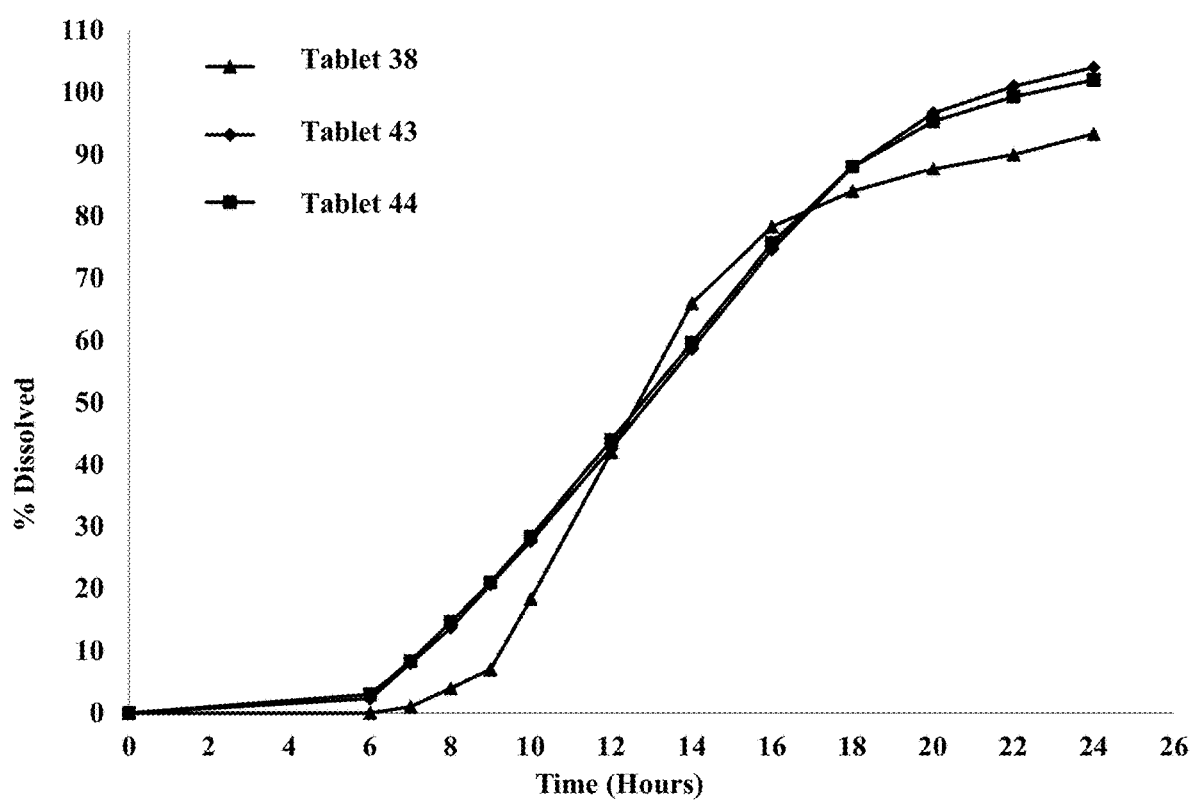

FIG. 19 compares the dissolution profiles of Tablets 38, 43, and 44 in about 900 ml of about 0.01N HCl, using USP II (sinkers) at 50 rpm and 37° C. Tablet 38 contained POLYOX® 1105 in the placebo layer and POLYOX® WSR 303 in the push layer; Tablet 43 contained POLYOX® N750 in the placebo layer and POLYOX® WSR 301 in the push layer; and Tablet 44 contained POLYOX® N80 in the placebo layer and POLYOX® WSR Coagulant in the push layer. Percent drug dissolved was plotted over time (hours). FIG. 19 demonstrates that compositions containing POLYOX® N750 in the placebo layer and POLYOX® WSR 301 in the push layer or compositions containing POLYOX® N80 in the placebo layer and POLYOX® WSR Coagulant in the push layer provide higher drug recovery, compared to compositions containing POLYOX® 1105 in the placebo layer and POLYOX® WSR 303 in the push layer.

Figure 20:
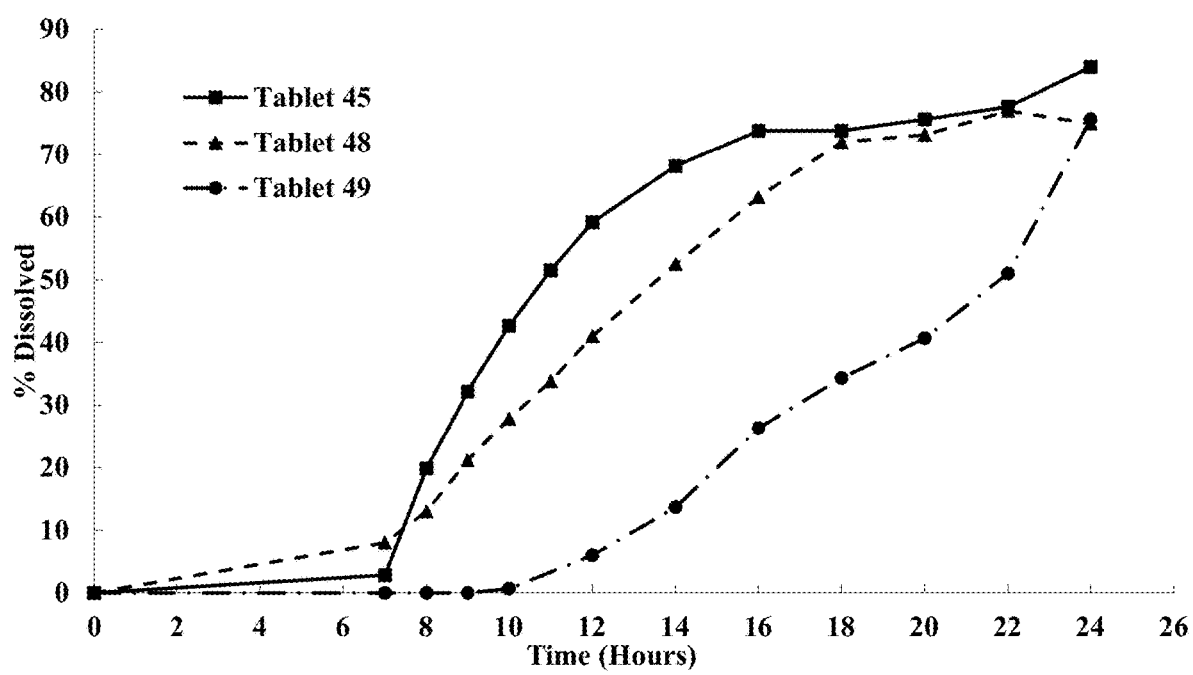

FIG. 20 provides dissolution profiles of Tablets 45, 48, and 49 in 5 ml of pH 6.8 buffer, using USP Apparatus II (Sinkers), at 5 rpm and 37° C. (low-volume, low-RPM condition). FIG. 20 demonstrates that Tablet 45, with about 10% coating weight gain, provides an improved release rate and improved drug recovery compared to Tablets 48 and 49, with about 12.5% coating weight gain. FIG. 20 further demonstrates that tablets with higher amount of pore former (Polyethylene glycol present in OPADRY® CA clear (90:10)) in the coating layer (e.g., Tablet 48), provide faster drug release compared to tablets containing less amount of pore former in OPADRY® CA clear (95:5) in the coating layer (e.g., Tablet 49), at a same coating weight gain. FIG. 20 also demonstrates that tablets containing POLYOX® 1105 in placebo layer and POLYOX® WSR 303 in push layer (Tablet 49) provided longer lag time compared to tablets containing POLYOX® 205 in placebo layer and POLYOX® WSR coagulant in the push layer (Tablets 45 and 48).

Figure 21:
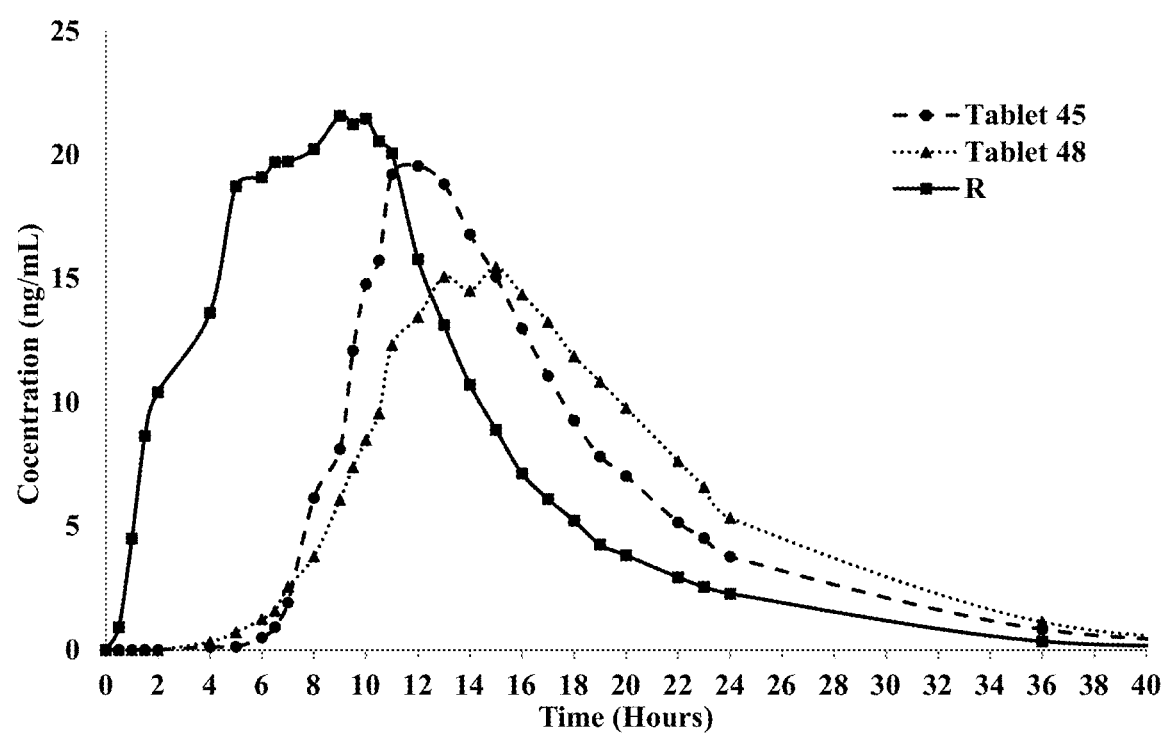

FIG. 21 compares pharmacokinetic performance of extended release compositions of the disclosure with marketed extended release methylphenidate product. FIG. 21 demonstrates that the compositions of the disclosure provide a lag time of about 7 hours and a $C_{max}$ of about 22 ng at 12 hours post administration.

Figure 22:
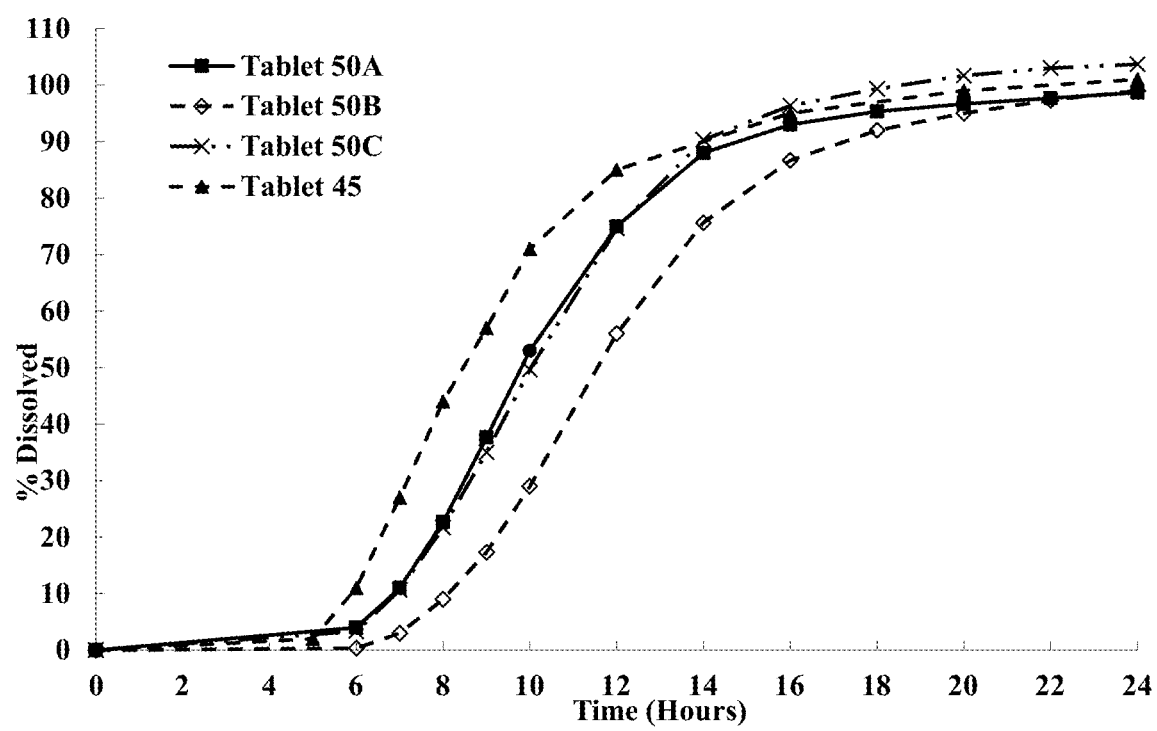

FIG. 22 provides dissolution profiles of Tablets 45, 50A, 50B, and 50C in 900 ml of 0.01N HCl, using USP Apparatus II (Sinkers), at 50 rpm and 37° C. Tablet 45 contained about 32 wt % of placebo layer, based on the total weight of the tablet core; Tablets 50A, 50B, and 50C contained about 35 wt % of placebo layer, based on the total weight of the tablet core. FIG. 22 demonstrates that lag time increases from about 5 hours to about 6 hours with increasing placebo layer amount from about 32 wt % to about 35 wt %, based on the total weight of the uncoated tablet core. FIG. 22 further demonstrates that drug recovery increases with increasing size of the orifice.

Figure 23:
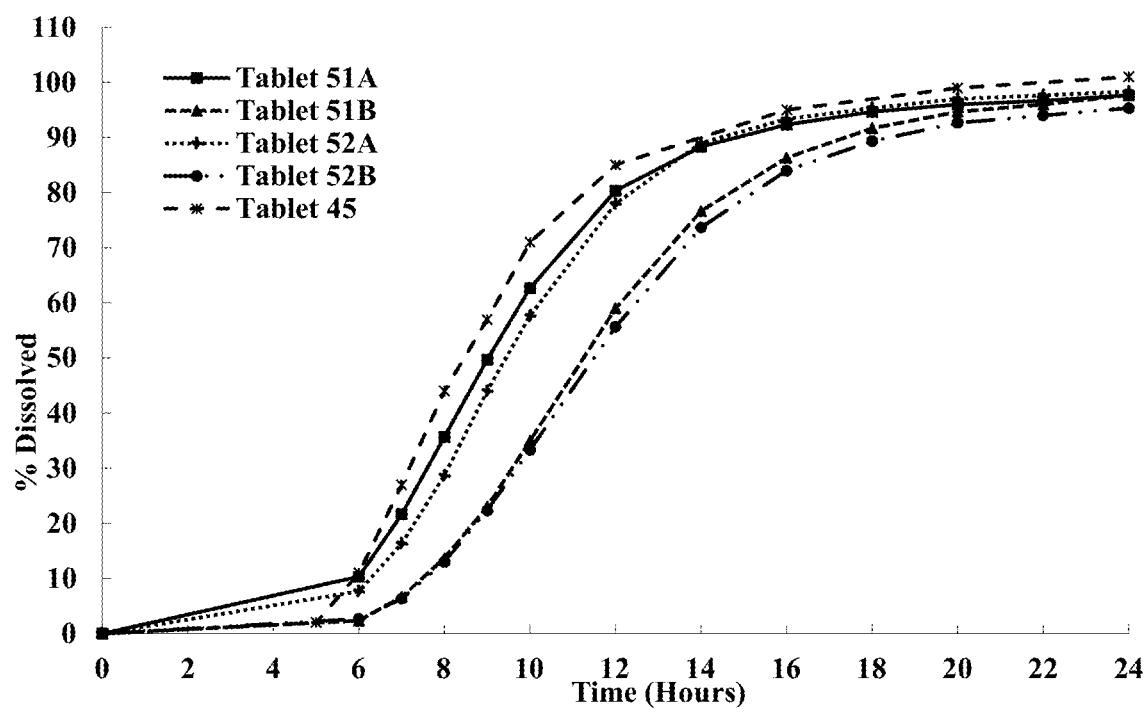

FIG. 23 provides dissolution profiles of Tablets 45, 51A, 51B, 52A, and 52B in 900 ml of 0.01N HCl, using USP Apparatus II (Sinkers), at 50 rpm and 37° C. Percent drug dissolved is plotted over time (hours). Placebo layer granules in Tablet 51A and Tablet 51B were made using 100% alcohol as the granulating solvent. Placebo layer granules in Tablet 52A and 52B were made using a mixture of alcohol and water as the granulating solvent. FIG. 23 demonstrates that granulation solvent does not have significant effect on release profile and lag time of the composition.

Figure 24:
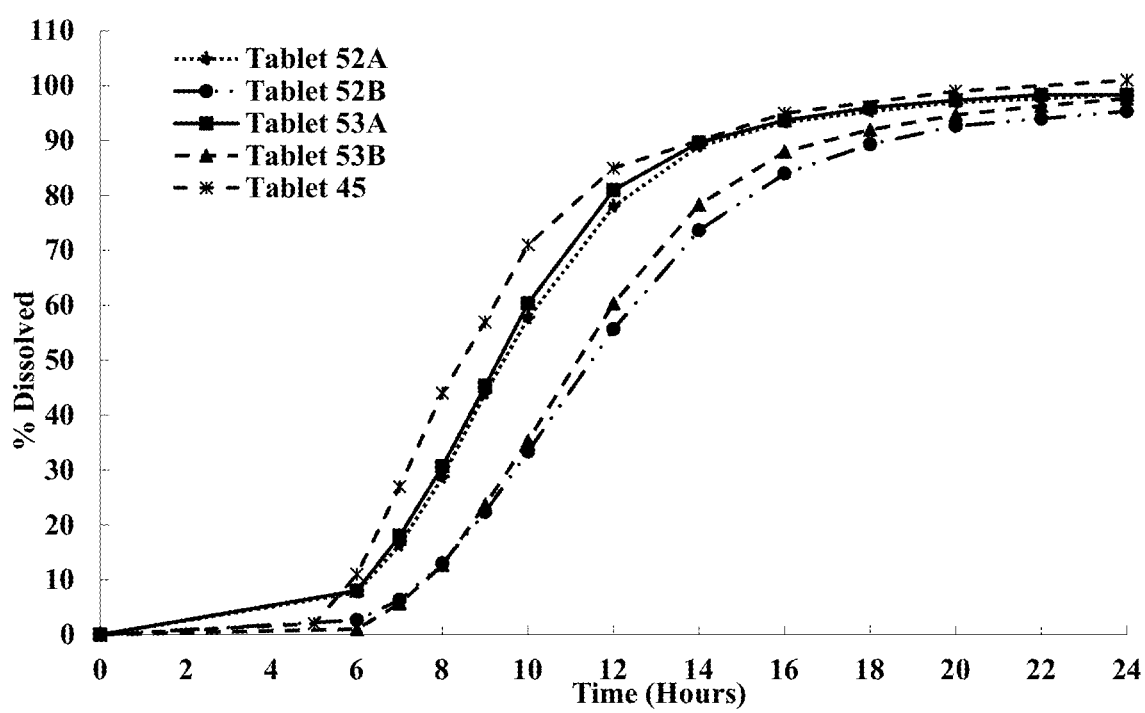

FIG. 24 provides dissolution profiles of Tablets 45, 52A, 52B, 53A, and 53B in 900 ml of 0.01N HCl, using USP Apparatus II (Sinkers), at 50 rpm and 37° C. Percent drug dissolved was plotted over time (hours). Placebo layer granules in Tablet 52A and Tablet 52B contained POLYOX® WSR 205. Placebo layer granules in Tablet 53A and 53B contained POLYOX® WSR 1105. FIG. 24 demonstrates that average molecular weight of POLYOX® present in the placebo layer does not have significant effect on release profile and lag time.

Figure 25:
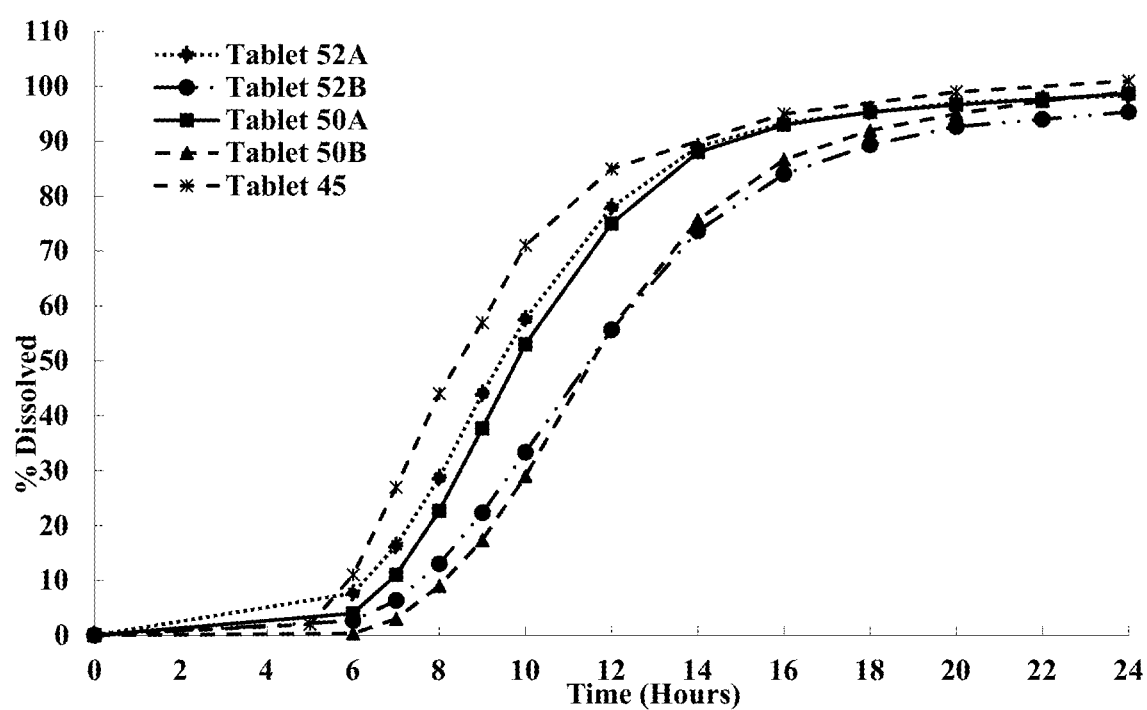

FIG. 25 provides dissolution profiles of Tablets 45, 50A, 50B, 52A, and 52B in 900 ml of 0.01N HCl, using USP Apparatus II (Sinkers), at 50 rpm and 37° C. Percent drug dissolved was plotted over time (hours). FIG. 25 demonstrates that the amount of POLYOX® present in the placebo layer does not have significant effect on release profile and lag time.

Figure 26:
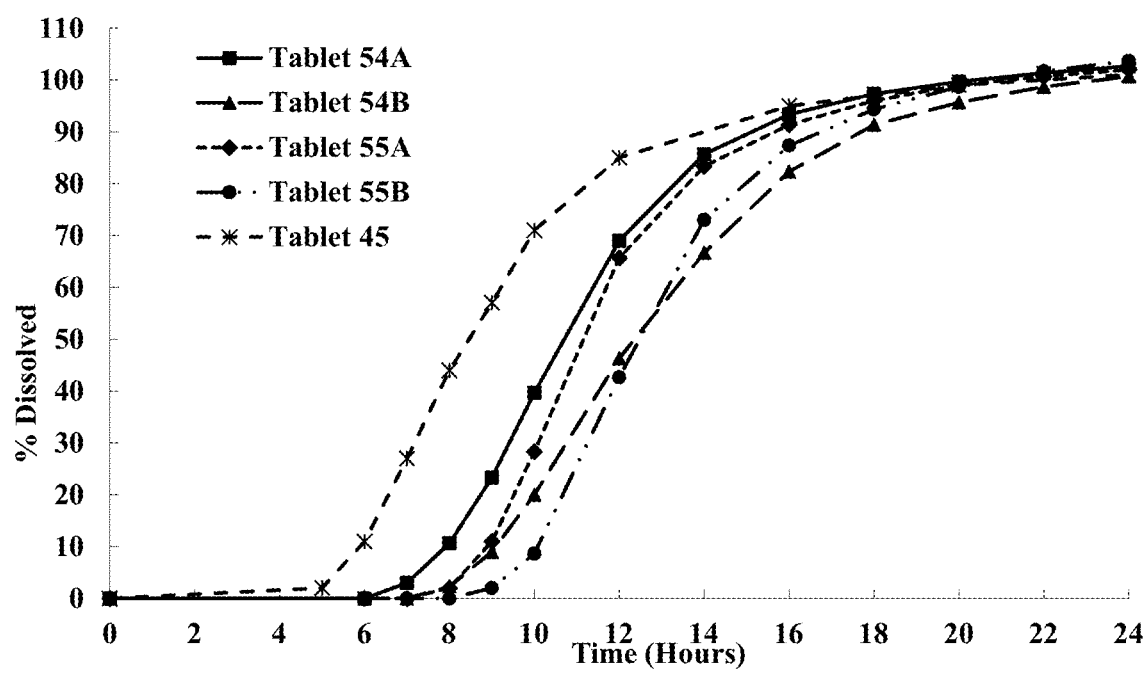

FIG. 26 provides dissolution profiles of Tablets 45, 54A, 54B, 55A, and 55B in 50 ml of pH 6.8 buffer, using USP Apparatus II (Sinkers), at 5 rpm and 37° C. Percent drug dissolved was plotted over time (hours). Placebo layer granules and active layer granules in Tablet 45 were made using dehydrated alcohol as granulation solvent. Placebo layer granules and active layer granules in Tablets 54A, 54B, 55A, and 55B were made using a mixture of alcohol and water as the granulation solvent. Tablets 45 and 54A and 54B contained 81 mg of POLYOX® N80 (Drug: polymer weight ratio of 40:60) in the active layer and Tablets 55A and 55B contained 33.67 mg of POLYOX® N80 (Drug: polymer weight ratio of 60:40) in the active layer. Further, Tablet 45 and 54 differed only in the amounts of placebo layer. Tablet 45 contained 122 mg of placebo layer and Tablet 54 contained 196 mg of placebo layer. FIG. 26 demonstrates that amount of POLYOX® present in the active layer, and granulation medium for making active layer granules and placebo layer granules affects lag time. FIG. 26 further demonstrates that the drug: polymer weight ratio affects the release rate, i.e., compositions with higher drug: polymer weight ratio provide faster release rate compared to compositions with lower drug: polymer weight ratio. FIG. 26 further demonstrates that lag time increases with increasing weight of the placebo layer, e.g., Tablet 54 exhibits higher lag time compared to Tablet 45.

Figure 27:
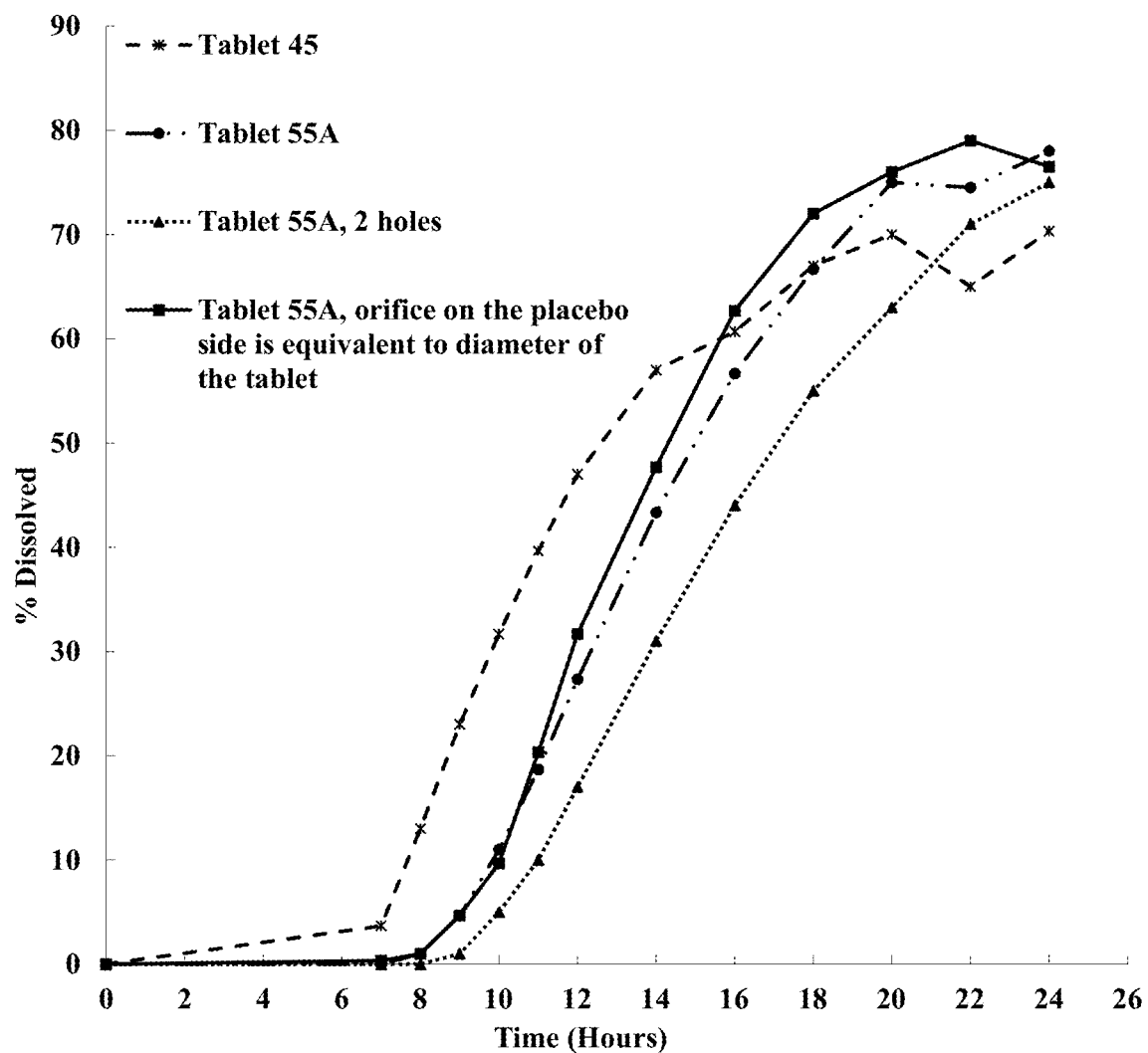

FIG. 27 provides dissolution profiles of Tablets 45, 55A with one 0.6 mm diameter orifice, Tablet 55A with two 0.6 mm diameter orifices, and Tablet 55A with placebo layer top diameter orifice, in 50 ml of pH 6.8 buffer, using USP Apparatus II (Sinkers), at 5 rpm and 37° C. Percentage dissolution of the tablets was measured at 2, 4, 6, 8, 10, 12, 14, 16, 18, 20, 22, and 24 hours.

6. DETAILED DESCRIPTION

The present disclosure is directed to delayed release methylphenidate compositions, amongst other things.

6.1. Definitions

The terminology used in the present disclosure is for the purpose of describing particular embodiments only and is not intended to be limiting. Certain terms are discussed below, or elsewhere in the specification, to provide additional guidance in describing the compositions and methods of the disclosure and how to make and use them. Unless otherwise defined, all terms, including technical and scientific terms used in the description, have the same meaning as commonly understood by one of ordinary skill in the art to which this disclosure belongs.

As used herein, the use of the word "a" or "an" when used in conjunction with the term "comprising" in the claims and/or when used in the specification can mean "one," but it is also consistent with the meaning of "one or more," "at least one," and "one or more than one." Still further, the terms "having," "including," "containing," and "comprising" are interchangeable, and one of skill in the art is cognizant that these terms are open-ended terms.

As used herein, "and/or" refers to and encompasses any and all possible combinations of one or more of the associated listed items.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 15%, up to 10%, up to 5%, up to 1%, up to 0.5%, or even up to 0.1% of a given value.

As used herein, a "therapeutically effective," "therapeutic," or "therapeutically acceptable" amount refers to an amount that will elicit a therapeutically useful response in a subject and includes an additional amount or overage of active ingredient deemed necessary in the formulation to provide the desired amount upon administration. The therapeutically useful response can provide some alleviation, mitigation, and/or decrease in at least one clinical symptom in the subject. Those skilled in the art will appreciate that the therapeutically useful response need not be complete or curative, as long as some benefit is provided to the subject.

As used herein, the term "drug recovery" refers to percentage of the total amount of drug present in the dosage form that is released in a dissolution medium. The term "complete drug recovery" refers to release of about 90% to about 105% of the drug present in the dosage form.

The term "bioavailability" refers to the fraction of an administered dose of unchanged drug that reaches the systemic circulation.

As used herein, the terms "treatment," "treat," and "treating" refer to reversing, alleviating, delaying the onset of, and/or inhibiting the progress of a disease or disorder as described herein. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example to prevent or delay their recurrence.

The term "chrono release" refers to drug release in a sequential order of time. In particular, the term "chrono release" means timed or programmed release of one or more drugs at a rhythm that matches the circadian rhythm of a condition's symptoms and/or of the individual being treated in the application of the therapy to optimize the therapeutic outcome and minimize side effects. In certain embodiments, the term "chrono release" includes immediate release of a drug followed by an extended release of the same or different drug.

The term "lag time", as used herein, refers to the time for which release of a drug is delayed from the time of administration/ingestion of the composition. Not more than 20% of the maximum plasma concentration ($C_{max}$) of the drug is released during the lag time.

The term "release rate", as used herein, refers to the quantity of drug released per unit time, e.g., mg of drug released per hour (mg/hour), from a dosage form. In certain embodiments, drug release rates can be calculated under in vitro dosage form dissolution testing conditions known in the art.

The term "delayed release" as used herein, refers to release of a discrete portion(s) of a drug at a time(s) other than immediately after administration/ingestion.

The term "immediate release", as used herein, refers to substantially complete release of a drug within a time period of about 1 hour or less, preferably within 30 minutes or less, post-administration.

The term "immediate release drug layer", as used herein, refers to an immediate release coating layer comprising a drug and at least one pharmaceutically acceptable carrier. The immediate release drug layer dissolves rapidly upon administration and provides an immediate release dose of the drug.

The term "controlled release", as used herein, refers to drug release that is controlled to alter the timing and/or rate of release of the drug substance from that of a conventional immediate release dosage form. The controlled release dosage forms of the disclosure can include modified release dosage forms providing delayed release (DR), extended release (ER), target release (TR), pulsatile release, chrono release, or any combination thereof, of drug substance.

The term "extended release", as used herein, refers to modified release dosage forms or compositions that are formulated to allow the drug to be available over an extended period of time after administration, thereby allowing a reduction in dosing frequency, as compared to a drug presented as an immediate release dosage form.

The terms "gastric medium," "simulated gastric fluid," "simulated intestinal fluid," "intestinal medium," and the like, as used herein, refer to media occurring in stomach and in intestines, correspondingly, or to the solutions that are used to mimic their chemical environment in vitro.

As used herein, the term "dissolution medium" refers to a medium used to mimic pH of gastric fluid in fed or fasted state of an individual. In certain embodiments, the medium used to mimic fed state of an individual includes pH 6.8 acetate buffer; and the medium used to mimic fasted state of an individual includes 0.01N HCl.

The term "discriminatory method," as used herein, refers to a biorelevant method that is used to mimic conditions of immediate microenvironment of release of methylphenidate or a pharmaceutically acceptable salt thereof. The "discriminating method" comprises measuring in vitro dissolution using USP II (Sinkers) in a small vessel containing 50 ml of pH 6.8 buffer, at 37° C., and at 5 rpm.

The term "solubility" is defined in terms of ability to dissolve in water. The term "highly soluble" includes drugs with a solubility of greater than 100 mg/ml of water; the term "moderately soluble" includes drugs with a solubility of between 100 mg/ml and 1 mg/ml of water; the term "sparingly soluble" includes drugs with a solubility of between 1 mg/ml and 0.1 mg/ml of water.; and the term "insoluble" includes drugs with a solubility of less than 0.1 mg/ml of water.

The term "osmosis" refers to a spontaneous movement of a solvent from a solution of lower solute concentration to a solute or a solution of higher solute concentration through a semipermeable membrane, wherein the membrane is permeable to the solvent and impermeable to the solute.

The term "osmotic pressure" refers to a pressure exerted on a higher solvent concentration side of the dosage form to inhibit solvent flow into the dosage form.

The term "substantially free", as used herein, refers to excluding any functional (e.g., noncontaminating) amount, i.e., any amount that contributes or has an effect on release profile or lag time of the composition.

The term "semipermeable membrane", as used herein, refers to a membrane or film that is substantially impermeable to the passage of solutes, e.g., a drug and other excipients, and substantially permeable to passage of fluids. As used herein, the terms functional coat and semipermeable membrane are used interchangeably.

The term "coating weight gain", as used herein, refers to coating weight gain with respect to the weight of the uncoated tablet. For example, a coating weight gain of 15% refers to a 15 wt % increase in tablet weight during coating with respect to the uncoated tablet weight.

The terms "pore former" and the like, as used herein, refer to water-soluble polymers and/or water-soluble small molecules that will form pores or channels (i.e., behave as a channeling agent) in a membrane/functional coat to improve permeability of the membrane/functional coat.

The terms "shear" and "shear effect," as used interchangeably herein, refer to peristaltic waves, particularly under fed conditions, moving from the mid-corpus of the stomach to the pylorus. Dissolution of compositions using USP Apparatus II (Sinkers) at 50 rpm and 37° C.; or using USP Apparatus III (Biodis) at 25 dpm and 37° C., mimics the effects of stomach shear on the dissolution profile of the composition.

The terms "orifice," "delivery port," and "hole," as used interchangeably herein, refer to an opening/exit means in coatings, e.g., in the semipermeable membrane/functional coat, the seal coat, and/or the overcoat, of an osmotic-controlled composition, on the placebo layer end of the multilayer core. The appropriate opening can be formed by any means know in the art, e.g., manual or laser drilling of the membrane. In certain embodiments, the semipermeable membrane facing the top of the placebo layer is completely removed to provide an orifice comprising an optimum diameter that is equivalent to the diameter of the top of the placebo layer end of the multilayer core. In certain embodiments, the optimum orifice diameter is from about 0.6 mm and about 1.5 mm.

The term "osmotic agent" as used herein, refers to swellable hydrophilic polymers, and osmogens/ionic compounds consisting of inorganic salts.

The term "wicking agent" as used herein, refers to a material with the ability to draw water into the porous network of the osmotic composition. The wicking agent helps to increase the contact surface area of the drug with the incoming aqueous fluid.

The term "patient" or "subject," as used herein, refers to a human or nonhuman mammal that is in need or may be in need to receive an osmotic dosage form of the present disclosure.

The terms "drug," "active agent," "active ingredient," and "active pharmaceutical ingredient/agent" are used interchangeably herein and include compounds that elicit a therapeutically useful response in a subject. The terms "drug," "active agent," "active ingredient," and "active pharmaceutical ingredient/agent" include all pharmaceutically acceptable polymorphs, salts, solvates, hydrates, esters, and functionally equivalent chemical compounds.

The term "methylphenidate" and "methylphenidate hydrochloride" are used interchangeably herein. The term "methylphenidate" includes all pharmaceutically acceptable polymorphs, salts, solvates, hydrates, esters, and functionally equivalent chemical compounds.

The terms "clonidine" and "clonidine hydrochloride" are used interchangeably herein. The term "clonidine" includes all pharmaceutically acceptable salts, esters, and functionally equivalent chemical compounds.

6.2 Multi-layer Osmotic Tablet Core

The present disclosure provides programmable osmotic-controlled oral compositions comprising a multilayer tablet core comprising methylphenidate or a pharmaceutically acceptable salt thereof (herein after as methylphenidate), wherein the core is coated with a semipermeable membrane comprising at least one orifice and, optionally, an immediate release coating, comprising a sedative for immediate release, over the semipermeable membrane. Non-limiting examples of sedatives suitable for inclusion in dosage forms described herein include clonidine, diphenhydramine, guanfacine, melatonin, or pharmaceutically acceptable polymorphs, salts, solvates, and hydrates thereof. In certain embodiments, the compositions of the disclosure do not include any sedative. The multilayered tablet core comprises a pull layer containing methylphenidate, and a push layer. The pull layer comprises at least two layers: a placebo layer, for providing a desired lag time for the release of methylphenidate, and an active layer containing methylphenidate for providing a delayed controlled release of methylphenidate. In certain embodiments, the orifice is present on the placebo layer side of the multilayer tablet core. In certain embodiments, the delayed controlled release is a delayed extended release. In certain embodiments, the tablets are vertically compressed producing a capsule-shaped product. In certain embodiments, such shape ensures complete extrusion of drug from the orifice.

For any of the dosage forms, compositions, and methods of the disclosure, the push layer is present in an amount that expands in volume to a size that pushes the entire drug solution or suspension in the pull layer, e.g., the placebo and active layers, out of the tablet through a delivery port/orifice, providing, e.g., a substantially complete drug recovery from the dosage form. In certain embodiments, the pull layer and the push layer are present in a weight ratio of about 2:1, about 1.5:1, about 1:1, or any intermediate values therein. In certain embodiments, the tablet core is a trilayer core comprising a pull layer comprising a placebo layer and an active layer; and a push layer. In certain embodiments, the weight of push layer is about 33% or more of the total weight of the trilayer core. In certain embodiments, the weight of the placebo layer or the active layer is about 33% or more of the total weight of the trilayer core. In certain embodiments, the weight of the placebo layer or the active layer is half or more of the total weight of the trilayer core. In certain embodiments, the weight of the placebo layer, the active layer, or the push layer can be from about 10 wt % to about 60 wt %, based on the total weight of the trilayer core. In certain embodiments, the weight of the placebo layer, the active layer, or the push layer can be from about 20 wt % to about 60 wt %, from about 25 wt % to about 50 wt %, or from about 30 wt % to about 50 wt %.

Furthermore, each of the layers, i.e., the active layer, the placebo layer, and the push layer, can comprise at least one polyethylene oxide polymer.

In certain embodiments, the placebo layer and the push layer are free of methylphenidate. In certain embodiments, methylphenidate contained in the active layer does not leach/migrate into the placebo layer or the push layer during an in vitro drug release test. In certain embodiments, less that about 20 wt %, less than about 15 wt %, less than about 10 wt %, less than about 7.5 wt %, or less than about 5 wt % of methylphenidate, based on the total weight of methylphenidate in the dosage form, is released along with the placebo layer. In certain embodiments, less that about 5 wt %, less than about 4 wt %, less than about 3 wt %, less than about 2 wt %, or less than about 1 wt %, based on the total dose of methylphenidate in the dosage form, is released between about 2 hours and about 10 hours, between about 2 hours and about 8 hours, between about 2 hours and about 7 hours, or between about 2 hours and about 6 hours following administration of the dosage form, thereby providing a lag time.

Placebo Layer

In certain embodiments, the placebo layer/placebo layer blend, is located adjacent to and in continuity with the orifice in the semipermeable membrane. In certain embodiments, the placebo layer blend comprises a swellable hydrophilic polymer, e.g., POLYOX® with an average molecular weight of from about 300,000 Da to about 900,000 Da, a binder, a lubricant, and a glidant. In certain embodiments, the placebo layer further comprises a color pigment. In certain embodiments, the placebo layer is substantially free of methylphenidate. In certain embodiments, the placebo layer blend further includes a stabilizer. In certain embodiments, the placebo layer blend further includes at least one osmogen and/or at least one wicking agent. In certain embodiments, the placebo layer blend includes granules containing a swellable hydrophilic polymer, a binder, a stabilizer, and a color pigment. In certain embodiments, the glidants and the lubricants are present as extragranular excipients in the placebo layer blend. In certain embodiments, the placebo layer blend is made by dry granulation/slugging. In certain embodiments, the placebo layer is made by direct compaction. In certain embodiments, placebo layer blend includes granules and extragranular excipients. In certain embodiments, the granules comprise a swellable hydrophilic polymer, a binder, an osmogen, a stabilizer, and a color pigment. In certain embodiments, granules further include a wicking agent. In certain embodiments, glidant and lubricant are present as extragranular excipients in the placebo layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol: water ratio of between about 60:40 and about 99:1.

In certain embodiments, the molecular weight/grade of the POLYOX® in the placebo layer affects drug recovery, lag time, and/or release profile, of the composition. In certain embodiments, the POLYOX® has an average molecular weight of about 300K (POLYOX® N-750), about 600K (POLYOX® N-205), about 900K (POLYOX® N-1105), or intermediate values thereof. In certain embodiments, viscosity of the placebo layer can be adjusted to provide a desired and consistent lag time. In certain embodiments, the viscosity of the placebo layer depends upon the average molecular weight of the POLYOX® present in the placebo layer. In certain embodiments, the placebo layer contains POLYOX® 205 or POLYOX® 1105. In certain embodiments, the placebo layer contains POLYOX® 1105. In certain embodiments, the placebo layer contains POLYOX® 205. In certain embodiments, the POLYOX® is present in an amount of about from 50 wt % to about 99 wt %, from about 50 wt % to about 95 wt %, from about 50 wt % to about 90 wt %, from about 50 wt % to about 85 wt %, from about 50 wt % to about 80 wt %, from about 50 wt % to about 75 wt %, from about 50 wt % to about 70 wt %, from about 50 wt % to about 65 wt %, from about 50 wt % to about 60 wt %, from about 55 wt %, to about 99 wt %, from about 60 wt % to about 99 wt %, from about 65 wt % to about 99 wt %, from about 70 wt % to about 99 wt %, from about 75 wt % to about 99 wt %, from about 80 wt % to about 99 wt %, from about 85 wt % to about 99 wt %, from about 90 wt % to about 99 wt %, from about 95 wt % to about 99 wt %, from about 55 wt % to about 95 wt %, from about 60 wt % to about 85 wt %, from about 65 wt % to about 80 wt %, or from about 70 wt % to about 75 wt %, based on the total weight of the placebo layer. In certain embodiments, the POLYOX® is present in an amount of about 50 wt %, about 55 wt %, about 60 wt %, about 65 wt %, about 70 wt %, about 75 wt %, about 80 wt %, about 81 wt %, about 82 wt %, about 83 wt %, about 84 wt %, about 85 wt %, about 86 wt %, about 87 wt %, about 88 wt %, about 89 wt %, about 90 wt %, about 91 wt %, about 92 wt %, about 93 wt %, about 94 wt %, about 95 wt %, about 96 wt %, about 97 wt %, about 98 wt %, about 99 wt %, or any intermediate values therein, based on the total weight of the placebo layer.

In certain embodiments, the placebo layer includes binders comprising, but not limited to, povidone (e.g., medium molecular weight KOLLIDON® 30 LP), hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide, polyethylene glycol, alginates, pegylated polyvinyl alcohol, or any combination thereof. In certain embodiments, the binder is povidone. In certain embodiments, the binders are present in an amount of from about 0.5 wt % to about 30 wt %, from about 0.5 wt % to about 29 wt %, from about 0.5 wt % to about 28 wt %, from about 0.5 wt % to about 27 wt %, from about 0.5 wt % to about 26 wt %, from about 0.5 wt % to about 25 wt %, from about 0.5 wt % to about 24 wt %, from about 0.5 wt % to about 23 wt %, from about 0.5 wt % to about 22 wt %, from about 0.5 wt % to about 21 wt %, from about 0.5 wt % to about 20 wt %, from about 0.5 wt % to about 19 wt %, from about 0.5 wt % to about 18 wt %, from about 0.5 wt % to about 17 wt %, from about 0.5 wt % to about 16 wt %, from about 0.5 wt % to about 15 wt %, from about 0.5 wt % to about 14 wt %, from about 0.5 wt % to about 13 wt %, from about 0.5 wt % to about 12 wt %, from about 0.5 wt % to about 11 wt %, from about 0.5 wt % to about 10 wt %, from about 0.5 wt % to about 9 wt %, from about 0.5 wt % to about 8 wt %, from about 0.5 wt % to about 7 wt %, from about 0.5 wt % to about 6 wt %, from about 0.5 wt % to about 5 wt %, from about 0.5 wt % to about 4 wt %, from about 0.5 wt % to about 3 wt %, from about 0.5 wt % to about 2 wt %, from about 0.5 wt % to about 1 wt %, from about 1 wt % to about 20 wt %, from about 2 wt %, to about 20 wt %, from about 3 wt % to about 20 wt %, from about 4 wt % to about 20 wt %, from about 5 wt % to about 20 wt %, from about 6 wt % to about 20 wt %, from about 7 wt % to about 20 wt %, from about 8 wt % to about 20 wt %, from about 9 wt % to about 20 wt %, from about 10 wt % to about 20 wt %, from about 11 wt % to about 20 wt %, from about 12 wt % to about 20 wt %, from about 13 wt % to about 20 wt %, from about 14 wt % to about 20 wt %, from about 15 wt % to about 20 wt %, from about 16 wt % to about 20 wt %, from about 17 wt % to about 20 wt %, from about 18 wt % to about 20 wt %, from about 19 wt % to about 20 wt %, from about 5 wt % to about 15 wt %, from about 5 wt % to about 10 wt %, or from about 10 wt % to about 15 wt %, based on the total weight of the placebo layer. In certain embodiments, the binders are present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, or any intermediates values therein, based on the total weight of the placebo layer.

In certain embodiments, the placebo layer includes at least one stabilizer to prevent degradation of POLYOX®. In certain embodiments, the stabilizer comprises antioxidants including, but not limited to, ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof. In certain embodiments, the antioxidant is butylated hydroxytoluene. In certain embodiments, the stabilizer is present in an amount of from about 0.01 wt % to about 0.5 wt %, from about 0.1 wt % to about 0.5 wt %, from about 0.2 wt % to about 0.5 wt %, from about 0.3 wt % to about 0.5 wt %, from about 0.4 wt % to about 0.5 wt %, from about 0.01 wt % to about 0.5 wt %, from about 0.01 wt % to about 0.4 wt %, from about 0.01 wt % to about 0.3 wt %, from about 0.01 wt % to about 0.2 wt %, from about 0.01 wt % to about 0.1 wt %, or from about 0.05% to about 0.3 wt %, based on the total weight of the placebo layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.10 wt %, about 0.2 wt %, about 0.3 wt %, about 0.4 wt %, about 0.5 wt %, or any intermediate values therein, based on the total weight of the placebo layer.

In certain embodiments, the placebo layer includes at least one lubricant comprising, but not limited to, magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, or any combination thereof. In certain embodiments, the lubricant is stearic acid. In certain embodiments, the lubricant is present as an extragranular excipient. In certain embodiments, the lubricant is present in an amount of from about 0.5 wt % to about 2 wt %, from about 0.5 wt % to about 1.5 wt %, from about 0.5 wt % to about 1.0 wt %, from about 1.0 wt % to about 2 wt %, or from about 1.0 wt % to about 1.5 wt %, based on the total weight of the placebo layer. In certain embodiments, the lubricant is present in an amount of about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, based on the total weight of the placebo layer.

In certain embodiments, the placebo layer includes at least one glidant, comprising, but not limited to, talc, colloidal silicon dioxide, magnesium trisilicate, powdered cellulose, starch, tribasic calcium phosphate, or any combinations thereof. In certain embodiments, the glidant is colloidal silicon dioxide (CAB-O-SIL®). In certain embodiments, the glidant is present as an extragranular excipient. In certain embodiments, the glidant is present in an amount of from about 0.05 wt % to about 5 wt %, from about 0.1 wt % to about 5 wt %, from about 0.5 wt % to about 5 wt %, from about 1 wt % to about 5 wt %, from about 1.5 wt % to about 5 wt %, from about 2 wt % to about 5 wt %, from about 2.5 wt % to about 5 wt %, from about 3 wt % to about 5 wt %, from about 3.5 wt % to about 5 wt %, from about 4 wt % to about 5 wt %, from about 4.5 wt % to about 5 wt %, from about 0.05 wt % to about 4.5 wt %, from about 0.05 wt % to about 4.0 wt %, from about 0.05 wt % to about 3.5 wt %, from about 0.05 wt % to about 3.0 wt %, from about 0.05 wt % to about 2.5 wt %, from about 0.05 wt % to about 2.0 wt %, from about 0.05 wt % to about 1.5 wt %, from about 0.05 wt % to about 1.0 wt %, from about 0.05 wt % to about 0.5 wt %, from about 0.05 wt % to about 0.1 wt %, from about 0.1 wt % to about 4.5 wt %, from about 1 wt % to about 4 wt %, or from about 1.5 wt % to about 3 wt %, based on the total weight of the placebo layer. In certain embodiments, the glidant is present in an amount of about 0.05 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, or any intermediate valued therein, based on the total weight of the placebo layer.

In certain embodiments, the placebo layer includes at least one color pigment to distinguish the placebo layer from the active layer. In certain embodiments, the color pigment comprises iron oxide or lake-based colors. In certain embodiments, the pigment is a lake-based color. In certain embodiments, the pigment is an iron oxide pigment, e.g., oxide pigment red, or oxide pigment black. In certain embodiments, the pigment is present in an amount of about 0.01 wt % to about 0.5 wt %, based on the total weight of the placebo layer.

In certain embodiments, the placebo layer further comprises osmogens, any disintegrants or water-entraining agents/wicking agents.

In certain embodiments, the osmogen is an ionic compound comprising, but not limited to, sodium chloride, potassium chloride, potassium sulfate, lithium sulfate, sodium sulfate, lactose-sucrose, lactose-dextrose, mannitol-dextrose, mannitol-lactose, lactose-fructose, dextrose-fructose, sucrose, dextrose, mannitol, sorbitol, xylitol, dibasic sodium phosphate, and combinations thereof. In certain embodiments, the osmogen is sodium chloride. In certain embodiments, the osmogen is present in an amount of from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 10 wt % to about 20 wt %, from about 15 wt % to about 20 wt %, or from about 10 wt % to about 15 wt %, based on the total weight of the placebo layer. In certain embodiments, the osmogen is present in an amount of about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, or any intermediate values therein, based on the total weight of the placebo layer.

In certain embodiments, the placebo layer comprises at least one wicking agent selected from the group comprising crospovidone, croscarmellose sodium, carmellose calcium, polyvinyl pyrolidone, low-substituted hydroxypropyl celluloses, sodium starch glycolate, alginic acid and alginates, acrylic acid derivatives, corn starch, maize starch, modified starches, and combinations thereof. In certain embodiments, the wicking agent is crospovidone. In certain embodiments, the wicking agent is present in an amount of from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 10 wt % to about 20 wt %, from about 15 wt % to about 20 wt %, or from about 10 wt % to about 15 wt %, based on the total weight of the placebo layer. In certain embodiments, the wicking agent is present in an amount of about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, or any intermediate values therein, based on the total weight of the placebo layer.

In certain embodiments, the relative weight percentage of the placebo layer, based on the total weight of the uncoated trilayer core, can be between about 10 wt % and about 60 wt %, between about 10 wt % and about 55 wt %, or between about 10 wt % and about 50 wt %

Active Layer

In certain embodiments, the active layer is located between (and adjacent to) and in contact with the placebo layer and the push layer. In certain embodiments, the active layer/active layer blend includes an active agent, a swellable hydrophilic polymer, a binder, an osmogen, and a lubricant. In certain embodiments, the active layer blend further includes a glidant and/or a stabilizer. In certain embodiments, the active layer blend further includes at least one osmogen and/or at least one wicking agent. In certain embodiments, the active layer blend includes granules containing a swellable hydrophilic polymer, a binder, an osmogen, a stabilizer, and a color pigment. In certain embodiments, the glidants and the lubricants are present as extragranular excipients in the active layer blend. In certain embodiments, the active layer blend is made by dry granulation/slugging. In certain embodiments, the active layer is made by direct compaction. In certain embodiments, active layer blend includes granules and extragranular excipients. In certain embodiments, the granules comprise methylphenidate, a swellable hydrophilic polymer, a binder, an osmogen, a stabilizer, and a color pigment. In certain embodiments, granules further include a surfactant and/or a wicking agent. In certain embodiments, glidant and lubricant are present as extragranular excipients in the active layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying weight ratios. In certain embodiments, the granulation solvent is a hydroalcoholic solvent containing dehydrated alcohol: water weight ratio of between about 60:40 and about 99:1. In certain embodiments, the swellable hydrophilic polymers comprise polyethylene oxide polymers with an average molecular weight of from about 100,000 Da to about 300,000 Da. In certain embodiments, the polyethylene oxide polymer has an average molecular weight of about 100,000 Da (POLYOX® N-10), about 200,000 Da (POLYOX® N-80), or about 300,000 Da (POLYOX® N-750). In certain embodiments, the average molecular weight of POLYOX® is about 200,000 Da.

In certain embodiments, the viscosity of the active layer is adjusted to provide a desired and consistent release profile. In certain embodiments, the viscosity of active layer depends upon the average molecular weight/grade of the POLYOX® present in the active layer. In certain embodiments, the active layer contains POLYOX® N-80 (200K). In certain embodiments, the POLYOX® is present in an amount of from about 30 wt % to about 80 wt %, from about 35 wt % to about 80 wt %, from about 40 wt % to about 80 wt %, from about 45 wt %, to about 80 wt %, from about 50 wt % to about 80 wt %, from about 55 wt % to about 80 wt %, from about 60 wt % to about 80 wt %, from about 65 wt % to about 80 wt %, from about 70 wt % to about 80 wt %, from about 75 wt % to about 80 wt %, from about 50 wt % to about 75 wt %, from about 50 wt % to about 70 wt %, from about 50 wt % to about 65 wt %, from about 50 wt % to about 60 wt %, from about 50 wt % to about 55 wt %, from about 55 wt % to about 75 wt %, or from about 60 wt % to about 70 wt %, based on the total weight of the active layer. In certain embodiments, the POLYOX® is present in an amount of about 40 wt %, about 45 wt %, about 50 wt %, about 55 wt %, about 60 wt %, about 65 wt %, about 70 wt %, about 71 wt %, about 72 wt %, about 73 wt %, about 74 wt %, about 75 wt %, about 76 wt %, about 77 wt %, about 78 wt %, about 79 wt %, about 80 wt %, or intermediate values therein, based on the total weight of the active layer.

In certain embodiments, the drug to POLYOX® weight ratio in the active layer, affects the lag time, release rate, and drug recovery of the composition. In certain embodiments, release rate and drug recovery from the composition increases with increasing the drug to POLYOX® ratio. In certain embodiments, the weight ratio of methylphenidate and POLYOX® is between about 10:90 and about 90:10. In certain embodiments, the weight ratio of methylphenidate and POLYOX® is about 10:90, about 20:80, about 30:70, about 40:60, about 50:50, about 60:40, about 70:30, 80:20, about 90:10, or any intermediate values therein. In certain embodiments, the methylphenidate HCl: POLYOX® weight ratio is from about 20:80 and about 70:30. In certain embodiments, compositions containing methylphenidate to POLYOX® weight ratio of about 60:40 provide a lag time of about 6-8 hours, a therapeutic release profile to provide complete drug recovery by 22 hours from the time of administration of the dosage form.

In certain embodiments, the active layer includes binders comprising, but not limited to, povidone (e.g., medium molecular weight KOLLIDON® 30 LP), hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide, polyethylene glycol, alginates, pegylated polyvinyl alcohol, or any combination thereof. In certain embodiments, the binder is povidone. In certain embodiments, the binders are present in an amount of about 0.5 wt % to about 30 wt %, 0.5 wt % to about 29 wt %, from about 0.5 wt % to about 28 wt %, from about 0.5 wt % to about 27 wt %, from about 0.5 wt % to about 26 wt %, from about 0.5 wt % to about 25 wt %, from about 0.5 wt % to about 24 wt %, from about 0.5 wt % to about 23 wt %, from about 0.5 wt % to about 22 wt %, from about 0.5 wt % to about 21 wt %, from about 0.5 wt % to about 20 wt %, from about 0.5 wt % to about 19 wt %, from about 0.5 wt % to about 18 wt %, from about 0.5 wt % to about 17 wt %, from about 0.5 wt % to about 16 wt %, from about 0.5 wt % to about 15 wt %, from about 0.5 wt % to about 14 wt %, from about 0.5 wt % to about 13 wt %, from about 0.5 wt % to about 12 wt %, from about 0.5 wt % to about 11 wt %, from about 0.5 wt % to about 10 wt %, from about 0.5 wt % to about 9 wt %, from about 0.5 wt % to about 8 wt %, from about 0.5 wt % to about 7 wt %, from about 0.5 wt % to about 6 wt %, from about 0.5 wt % to about 5 wt %, from about 0.5 wt % to about 4 wt %, from about 0.5 wt % to about 3 wt %, from about 0.5 wt % to about 2 wt %, from about 0.5 wt % to about 1 wt %, from about 1 wt % to about 20 wt %, from about 2 wt %, to about 20 wt %, from about 3 wt % to about 20 wt %, from about 4 wt % to about 20 wt %, from about 5 wt % to about 20 wt %, from about 6 wt % to about 20 wt %, from about 7 wt % to about 20 wt %, from about 8 wt % to about 20 wt %, from about 9 wt % to about 20 wt %, from about 10 wt % to about 20 wt %, from about 11 wt % to about 20 wt %, from about 12 wt % to about 20 wt %, from about 13 wt % to about 20 wt %, from about 14 wt % to about 20 wt %, from about 15 wt % to about 20 wt %, from about 16 wt % to about 20 wt %, from about 17 wt % to about 20 wt %, from about 18 wt % to about 20 wt %, from about 19 wt % to about 20 wt %, from about 5 wt % to about 15 wt %, from about 5 wt % to about 10 wt %, or from about 10 wt % to about 15 wt %, based on the total weight of the active layer. In certain embodiments, the binders are present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, or any intermediates values therein, based on the total weight of the active layer.

In certain embodiments, the active layer comprises osmogens and/or any disintegrants or water-entraining agents/wicking agents. In certain embodiments, the active layer comprises at least one osmogen. In certain embodiments, the osmogen is an ionic compound comprising, but not limited to, sodium chloride, potassium chloride, potassium sulfate, lithium sulfate, sodium sulfate, lactose-sucrose, lactose-dextrose, mannitol-dextrose, mannitol-lactose, lactose-fructose, dextrose-fructose, sucrose, dextrose, mannitol, sorbitol, xylitol, dibasic sodium phosphate, and combinations thereof. In certain embodiments, the osmogen is sodium chloride. In certain embodiments, the osmogen is present in an amount of from about 2 wt % to about 40 wt %, from about 2 wt % to about 35 wt %, from about 2 wt % to about 30 wt %, from about 2 wt % to about 25 wt %, from about 2 wt % to about 20 wt %, from about 2 wt % to about 19 wt %, from about 2 wt % to about 18 wt %, from about 2 wt % to about 17 wt %, from about 2 wt % to about 16 wt %, from about 2 wt % to about 15 wt %, from about 2 wt % to about 14 wt %, from about 2 wt % to about 13 wt %, from about 2 wt % to about 12 wt %, from about 2 wt % to about 11 wt %, from about 2 wt % to about 10 wt %, from about 2 wt % to about 9 wt %, from about 2 wt % to about 8 wt %, from about 2 wt % to about 7 wt %, from about 2 wt % to about 6 wt %, from about 2 wt % to about 5 wt %, from about 2 wt % to about 4 wt %, from about 2 wt % to about 3 wt %, from about 3 wt % to about 20 wt %, from about 4 wt % to about 20 wt %, from about 5 wt % to about 20 wt %, from about 6 wt % to about 20 wt %, from about 7 wt % to about 20 wt %, from about 8 wt % to about 20 wt %, from about 9 wt % to about 20 wt %, from about 10 wt % to about 20 wt %, from about 11 wt % to about 20 wt %, from about 12 wt % to about 20 wt %, from about 13 wt % to about 20 wt %, from about 14 wt % to about 20 wt %, from about 15 wt % to about 20 wt %, from about 16 wt % to about 20 wt %, from about 17 wt % to about 20 wt %, from about 18 wt % to about 20 wt %, from about 19 wt % to about 20 wt %, from about 5 wt % to about 15 wt %, from about 5 wt % to about 10 wt %, or from about 10 wt % to about 15 wt %, based on the total weight of the active layer. In certain embodiments, the osmogen is present in an amount of about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, or any intermitates values therein, based on the total weight of the active layer.

In certain embodiments, the active layer comprises at least one wicking agent selected from the group comprising crospovidone, croscarmellose sodium, carmellose calcium, polyvinyl pyrolidone, low-substituted hydroxypropyl celluloses, sodium starch glycolate, alginic acid and alginates, acrylic acid derivatives, corn starch, maize starch, modified starches, and combinations thereof. In certain embodiments, the wicking agent is crospovidone. In certain embodiments, the wicking agent is present in an amount of from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 10 wt % to about 20 wt %, from about 15 wt % to about 20 wt %, or from about 10 wt % to about 15 wt %, based on the total weight of the active layer. In certain embodiments, the wicking agent is present in an amount of about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, or any intermediate values therein, based on the total weight of the active layer.

In certain embodiments, the active layer comprises at least one stabilizer to prevent/reduce the degradation of POLYOX®. In certain embodiments, the stabilizer comprises, but is not limited to, ascorbic acid, succinic acid, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof. In certain embodiments, the stabilizer is BHT. In certain embodiments, the stabilizer is succinic acid. In certain embodiments, the stabilizer is a combination of BHT and succinic acid. In certain embodiments, the stabilizer is present in an amount of about 0.01 wt % to about 0.5 wt %, from about 0.1 wt % to about 0.5 wt %, from about 0.2 wt % to about 0.5 wt %, from about 0.3 wt % to about 0.5 wt %, from about 0.4 wt % to about 0.5 wt %, from about 0.01 wt % to about 0.5 wt %, from about 0.01 wt % to about 0.4 wt %, from about 0.01 wt % to about 0.3 wt %, from about 0.01 wt % to about 0.2 wt %, from about 0.01 wt % to about 0.1 wt %, or from about 0.05% to about 0.3 wt %, based on the total weight of the active layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, or any intermediate values therein, based on the total weight of the active layer.

In certain embodiments, the active layer further includes surfactants to modulate the solubility of the active agent. In certain embodiments, surfactant comprises, but is not limited to, esters of fatty acids; sorbitan fatty acid esters ethoxylated with from 2 to 30 moles of ethylene oxide; polyethylene glycol fatty acid esters; polyethylene glycol esters and polyethylene glycol ethers; and polyethoxylated carboxylic acids, PEG-7 hydrogenated castor oil, and PEG-30 dipolyhydroxystearate; block copolymers based on ethylene oxide and propylene oxide; dioctyl sodium sulfosuccinate (docusate sodium); sodium lauryl sulfate; PEG-32 glyceryl laurate; PEG-32 glyceryl palmitostearate; PEG-8 glyceryl caprylate/caprate; PEG-6 glyceryl caprylate/caprate; macrogol 15 hydroxystearate; polyoxyethylene 20 sorbitan monolaurate (polysorbate 20); polyoxyethylene 20 sorbitan monooleate (polysorbate 80); sorbitan monolaurate; sorbitan monooleate; polyoxyl 40 stearate, and any combinations thereof.

In certain embodiments, the active layer includes lubricants comprising, but not limited to, magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, or any combination thereof. In certain embodiments, the lubricant is stearic acid. In certain embodiments, the lubricant is present in an amount of about 0.01 wt % to about 2 wt %, from about 0.01 wt % to about 1.5 wt %, from about 0.01 wt % to about 1.0 wt %, from about 0.01 wt % to about 0.5 wt %, from about 0.01 wt % to about 0.1 wt %, from about 0.1 wt % to about 2 wt %, from about 1.0 wt % to about 2.0 wt %, from about 1.5 wt % to about 2.0 wt %, from about 0.1 wt % to about 1.0 wt %, or from about 0.5 wt % to about 1.5 wt % based on the total weight of the active layer. In certain embodiments, the lubricant is present in an amount of about 0.01 wt %, about 0.02 wt %, about 0.03 wt %, about 0.04 wt %, about 0.05 wt %, about 0.1 wt %, about 0.2 wt %, about 0.3 wt %, about 0.4 wt % about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, based on the total weight of the active layer.

In certain embodiments, the active layer includes glidants comprising, but not limited to, talc, colloidal silicon dioxide, magnesium trisilicate, powdered cellulose, starch, tribasic calcium phosphate, or combinations thereof. In certain embodiments, the glidant is colloidal silicon dioxide (CAB-0-SIO. In certain embodiments, the glidant is present in an amount of about 0.05 wt % to about 5 wt %, from about 0.05 wt % to about 4 wt %, from about 0.05 wt % to about 3 wt %, from about 0.05 wt % to about 2 wt %, from about 0.05 wt % to about 1.0 wt %, from about 0.05 wt % to about 0.5 wt %, from about 0.1 wt % to about 5 wt %, from about 1.0 wt % to about 5 wt %, from about 1.5 wt % to about 5 wt %, from about 2.0 wt % to about 5 wt %, from about 2.5 wt % to about 5 wt %, from about 3.0 wt % to about 5 wt %, from about 3.5 wt % to about 5 wt %, from about 4.0 wt % to about 5 wt %, from about 4.5 wt % to about 5 wt %, from about 0.1 wt % to about 4.5 wt %, from about 1 wt % to about 4 wt %, or from about 1.5 wt % to about 3 wt %, based on the total weight of the placebo layer. In certain embodiments, the glidant is present in an amount of about 0.05 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, or any intermediate valued therein, based on the total weight of the active layer.

In certain embodiments, the weight percentage of the active layer, based on the total weight of the uncoated trilayer core, can be between about 10 wt % and about 60 wt %, between about 15 wt % and about 50 wt %, between about 20 wt % and about 45 wt %, between about 25 wt % and about 40 wt %, or about 30 wt %.

Push Layer

In certain embodiments, the push layer is located adjacent to the active layer. In certain embodiments, the push layer/push layer blend includes a swellable hydrophilic polymer, a binder, an osmogen, a lubricant, and a color pigment. In certain embodiments, the push layer blend further includes a glidant and/or a stabilizer. In certain embodiments, the push layer does not include any drug. In certain embodiments, the swellable hydrophilic polymer is a polyethylene oxide polymer having an average molecular weight of greater than or equal to 1000,000 Da. In certain embodiments, the push layer blend includes granules containing a swellable hydrophilic polymer, a binder, an osmogen, a stabilizer, and a color pigment. In certain embodiments, the glidants and the lubricants are present as extragranular excipients in the active layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying weight ratios. In certain embodiments, the granulation solvent is a hydroalcoholic solvent containing dehydrated alcohol: water weight ratio of between about 60:40 and about 99:1. In certain embodiments, the push layer blend is made by dry granulation/slugging. In certain embodiments, the push layer is made by direct compaction.

In certain embodiments, the average molecular weight of the polyethylene oxide polymer in the push layer is about 1000,000 Da (POLYOX® WSR N 12K), about 2000,000 Da (POLYOX® WSR N 60K), about 4000,000 Da (POLYOX® WSR 301), about 5000,000 Da (POLYOX® WSR coagulant), about 7000,000 Da (POLYOX® WSR 303), or any intermediate values therein. In certain embodiments, swelling of POLYOX® WSR coagulant (5M) can be enhanced by mixing with a portion of POLYOX® WSR 303 (7M). In certain embodiments, swelling of POLYOX® coagulant can be reduced by mixing with a portion of POLYOX®WSR 301 (4M). In certain embodiments, the POLYOX® is present in an amount of about 40 wt % to about 80 wt %, from about 40 wt % to about 75 wt %, from about 40 wt % to about 70 wt %, from about 40 wt % to about 65 wt %, from about 40 wt % to 60 wt %, from about 40 wt % to 55 wt %, from about 40 wt % to 50 wt %, from about 40 wt % to 45 wt %, from about 45 wt % to about 80 wt %, from about 50 wt % to about 80 wt %, from about 55 wt % to about 80 wt %, from about 60 wt % to about 80 wt %, from about 65 wt % to about 80 wt %, from about 70 wt % to about 80 wt %, from about 75 wt % to about 80 wt %, from about 45 wt % to about 75 wt %, from about 50 wt % to about 70 wt %, or from about 55 wt % to about 65 wt %, based on the total weight of the push layer. In certain embodiments, the POLYOX® is present in an amount of about 45 wt %, about 50 wt %, about 55 wt %, about 60 wt %, about 65 wt %, about 70 wt %, about 75 wt %, about 80 wt %, or any intermediate values therein, based on the total weight of the push layer.

In certain embodiments, the amount and grade of the POLYOX® present in the push layer affects the release profile of the drug from the dosage form, i.e., an increase in the molecular weight or amount of POLYOX® in the push layer will increase the force exerted on the pull layer for fast and complete drug recovery. In certain embodiments, the grade of POLYOX® is selected to provide desired lag time, release rate, and complete drug recovery in about 22 hours from the time of administration of the dosage form.

In certain embodiments, the push layer comprises at least one osmogen. In certain embodiments, the presence of osmogen in the push layer is essential for uniform swelling of the tablet core. In certain embodiments, the osmogen provides a concentration gradient for osmotic flow of liquid into the composition. The rate at which the polyethylene oxide polymer in the push layer absorbs water depends on the osmotic pressure generated by the osmogen present in the push layer, and the permeability of the semipermeable membrane/functional coat. As the polyethylene oxide polymer present in the push layer absorbs water, it expands in volume, which pushes the drug solution or suspension in the pull layer out of the tablet through the orifice/hole in the membrane. The compositions release drug at a rate, which is independent of pH and hydrodynamics of the dissolution medium.

In certain embodiments, the osmogen is an ionic compound comprising, but not limited to, sodium chloride, potassium chloride, potassium sulfate, lithium sulfate, sodium sulfate, lactose-sucrose, lactose-dextrose, mannitol-dextrose, mannitol-lactose, lactose-fructose, dextrose-fructose, sucrose, dextrose, mannitol, sorbitol, xylitol, dibasic sodium phosphate, and combinations thereof. In certain embodiments, the osmogen is sodium chloride. In certain embodiments, the osmogen is present in an amount of about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 10 wt % to about 30 wt %, from about 15 wt % to about 30 wt %, from about 20 wt % to about 30 wt %, from about 25 wt % to about 30 wt %, or from about 10 wt % to about 25 wt %, or from about 15 wt % to about 20 wt %, based on the total weight of the push layer. In certain embodiments, the osmogen is present in an amount of about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, or any intermediate values therein, based on the total weight of the push layer. In certain embodiments, the osmogen is present in an amount of from about 10 wt % to about 30 wt %, based on the total weight of the push layer.

In certain embodiments, the push layer includes at least one binder selected from the group consisting of, but not limited toto, povidone (e.g., medium molecular weight KOLLIDON® 30 LP), hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide, polyethylene glycol, alginates, pegylated polyvinyl alcohol, and any combination thereof. In certain embodiments, the binder is povidone. In certain embodiments, the binders are present in an amount of from about 0.5 wt % to about 30 wt %, from about 0.5 wt % to about 29 wt %, from about 0.5 wt % to about 28 wt %, from about 0.5 wt % to about 27 wt %, from about 0.5 wt % to about 26 wt %, from about 0.5 wt % to about 25 wt %, from about 0.5 wt % to about 24 wt %, from about 0.5 wt % to about 23 wt %, from about 0.4 wt % to about 22 wt %, from about 0.5 wt % to about 21 wt %, from about 0.5 wt % to about 20 wt %, from about 0.5 wt % to about 19 wt %, from about 0.5 wt % to about 18 wt %, from about 0.5 wt % to about 17 wt %, from about 0.5 wt % to about 16 wt %, from about 0.5 wt % to about 15 wt %, from about 0.5 wt % to about 14 wt %, from about 0.5 wt % to about 13 wt %, from about 0.5 wt % to about 12 wt %, from about 0.5 wt % to about 11 wt %, from about 0.5 wt % to about 10 wt %, from about 0.5 wt % to about 9 wt %, from about 0.5 wt % to about 8 wt %, from about 0.5 wt % to about 7 wt %, from about 0.5 wt % to about 6 wt %, from about 0.5 wt % to about 5 wt %, from about 0.5 wt % to about 4 wt %, from about 0.5 wt % to about 3 wt %, from about 0.5 wt % to about 2 wt %, from about 0.5 wt % to about 1 wt %, from about 1 wt % to about 20 wt %, from about 2 wt %, to about 20 wt %, from about 3 wt % to about 20 wt %, from about 4 wt % to about 20 wt %, from about 5 wt % to about 20 wt %, from about 6 wt % to about 20 wt %, from about 7 wt % to about 20 wt %, from about 8 wt % to about 20 wt %, from about 9 wt % to about 20 wt %, from about 10 wt % to about 20 wt %, from about 11 wt % to about 20 wt %, from about 12 wt % to about 20 wt %, from about 13 wt % to about 20 wt %, from about 14 wt % to about 20 wt %, from about 15 wt % to about 20 wt %, from about 16 wt % to about 20 wt %, from about 17 wt % to about 20 wt %, from about 18 wt % to about 20 wt %, from about 19 wt % to about 20 wt %, from about 5 wt % to about 15 wt %, from about 5 wt % to about 10 wt %, or from about 10 wt % to about 15 wt %, based on the total weight of the push layer. In certain embodiments, the binders are present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, or any intermediates values therein, based on the total weight of the push layer.

In certain embodiments, the push layer includes at least one stabilizer to prevent degradation of POLYOX®. In certain embodiments, the stabilizer comprises, but is not limited to, ascorbic acid, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof. In certain embodiments, the stabilizer is BHT. In certain embodiments, the stabilizer is present in an amount of about 0.01 wt % to about 0.5 wt %, from about 0.1 wt % to about 0.5 wt %, from about 0.2 wt % to about 0.5 wt %, from about 0.3 wt % to about 0.5 wt %, from about 0.4 wt % to about 0.5 wt %, from about 0.01 wt % to about 0.4 wt %, from about 0.01 wt % to about 0.3 wt %, from about 0.01 wt % to about 0.2 wt %, from about 0.01 wt % to about 0.1 wt %, or from about 0.05% to about 0.3 wt %, based on the total weight of the push layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, or any intermediate values therein, based on the total weight of the push layer.

In certain embodiments, the push layer includes lubricants comprising, but not limited to, magnesium stearate, glyceryl monostearates, palmitic acid, talc, carnauba wax, calcium stearate sodium, sodium or magnesium lauryl sulfate, calcium soaps, zinc stearate, polyethylene oxide, polyethylene glycols, polyoxyethylene monostearates, calcium silicate, silicon dioxide, hydrogenated vegetable oils and fats, stearic acid, or any combination thereof. In certain embodiments, the lubricant is stearic acid. In certain embodiments, the lubricant is present in an amount of about 0.1 wt % to about 2 wt %, from about 0.1 wt % to about 1.5 wt %, from about 0.1 wt % to about 1.0 wt %, from about 0.1 wt % to about 0.5 wt %, from about 0.5 wt % to about 2 wt %, from about 1.0 wt % to about 2.0 wt %, from about 1.5 wt % to about 2.0 wt %, or from about 1.0 wt % to about 1.5 wt % based on the total weight of the push layer. In certain embodiments, the lubricant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, based on the total weight of the push layer.

In certain embodiments, the push layer includes at least one glidant comprising, but not limited to, talc, colloidal silicon dioxide, magnesium trisilicate, powdered cellulose, starch, and tribasic calcium phosphate. In certain embodiments, the glidant is colloidal silicon dioxide. In certain embodiments, the glidant is present in an amount of about 0.05 wt % to about 5 wt %, from about 0.1 wt % to about 1.5 wt %, from about 0.1 wt % to about 1.0 wt %, from about 0.1 wt % to about 0.5 wt %, from about 0.5 wt % to about 2 wt %, from about 1.0 wt % to about 2.0 wt %, from about 1.5 wt % to about 2.0 wt %, or from about 1.0 wt % to about 1.5 wt % based on the total weight of the push layer. In certain embodiments, the glidant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, or any intermediate valued therein, based on the total weight of the push layer.

In certain embodiments, the push layer includes at least one color pigment for identifying the push layer in the multilayer tablet core. In certain embodiments, the push layer and the placebo layer include the same color pigment. In certain embodiments, the placebo layer contains less amount of color pigment than the push layer. In certain embodiments, the push layer is darker in color than the placebo layer, which helps in identifying the placebo layer side while drilling a orifice in the membrane on the placebo layer side of the multilayer core. In certain embodiments, the push layer includes at least one pigment comprising iron oxide or lake-based colors. In certain embodiments, the pigment is a lake-based color. In certain embodiments, the pigment is an iron oxide pigment, e.g., oxide pigment red, and oxide pigment black. In certain embodiments, the pigment is present in an amount of about 0.5 wt % to about 2 wt % of the push layer.

In certain embodiments, the amount of push layer, based on the total weight of the uncoated trilayer core, can be between about 10 wt % and about 60 wt %, between about 20 wt % and about 55 wt %, between about 25 wt % and about 50 wt %, or between about 30 wt % and about 40 wt %.

Semipermeable Membrane

In certain embodiments, the trilayer tablet core is coated with a semipermeable membrane. In certain embodiments, the semipermeable membrane is a polymeric film coating containing at least one orifice/hole/delivery port for drug release. In certain embodiments, size of the orifice must be optimized to control drug release from the dosage form. The size of orifice should not be too large to allow solute diffusion from the orifice into the core, and not too small to build hydrostatic pressure within the core.

In certain embodiments, the orifice is made via manual or laser drilling. In certain embodiments, the optimum orifice diameter is less than about 12.0 mm. In certain embodiments, the optimum orifice diameter is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, or any intermediate values therein. In certain embodiments, the optimum orifice diameter is equivalent to the diameter of the top of placebo layer end of the tablet core coated with the semipermeable membrane. In certain embodiments, it is important that the semipermeable membrane is adequately perforated with an orifice without compromising the integrity of the tablet core.

In certain embodiments, the coating composition and/or coating weight gain of the semipermeable membrane determines the lag time provided by the composition. In certain embodiments, the coating weight gain of the semipermeable membrane ranges from about 1 wt % to about 50 wt %, from about 5 wt % to about 45 wt %, from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, or any intermediate ranges therein, based on the total weight of the uncoated tablet core. In certain embodiments, the coating weight gain is about 10 wt %, about 12.5 wt %, or about 15 wt %, based on the total weight of the uncoated tablet core.

In certain embodiments, the semipermeable membrane coat over the multilayered tablet core is substantially impermeable to drugs and excipients present in the multilayered tablet core. In certain embodiments, the semipermeable membrane is permeable to solvents, such as water, GI fluid, and simulated GI fluid. In certain embodiments, the semipermeable membrane doesn't react with gastric fluid regardless of the pH. In certain embodiments, the semipermeable membrane maintains the integrity of the composition to provide constant osmotic pressure during drug delivery. In certain embodiments, the semipermeable membrane comprises one or more pH-independent water-insoluble polymers that are permeable to water and substantially impermeable to solutes, e.g., drugs and excipients. Polymers suitable for inclusion in the semipermeable membrane comprise, but are not limited to, cellulose esters, e.g., cellulose acetate, cellulose diacetate, cellulose triacetate, cellulose propionate, cellulose acetate butyrate, and combinations thereof. In certain embodiments, the semipermeable membrane comprises cellulose acetate. In certain embodiments, the permeability of cellulose acetate is enhanced by increasing the acetyl content in cellulose acetate. In certain embodiments, the semipermeable membrane comprises cellulose acetate with at least 30% acetyl content. In certain embodiments, the semipermeable membrane comprises cellulose acetate with about 32% acetyl content, about 35% acetyl content, about 38% acetyl content, about 39% acetyl content, or about 39.8% acetyl content. In certain embodiments, permeability of the semipermeable membrane is enhanced by addition of water-soluble pore formers to the membrane composition. The pore formers create formation of a microporous membrane in situ. In certain embodiments, the water-soluble pore formers comprise, but are not limited to, of polyethylene glycol (PEG 400, PEG 1000, PEG 1450, PEG 3350), hydroxypropyl cellulose, polyvinyl pyrolidone (PVP), KOLLIDON® 30, KOLLICOAT® IR, sucrose, glucose, fructose, lactose, mannose, mannitol, sorbitol, methyl cellulose (METHOCEL™ E3, METHOCEL™ E5, METHOCEL™ E6), poloxamers, e.g., poloxamer 188, triethyl citrate, triacetin, hydroxypropyl methylcellulose, polyhydric alcohols such as glycerol, and combinations thereof. In certain embodiments, the semipermeable membrane comprises cellulose acetate and a pore former comprising polyethylene glycol. In certain embodiments, the pore former is polyethylene glycol 3350. In certain embodiments, the weight ratio of cellulose acetate to polyethylene glycol is between about 80:20 and about 99.5:0.5. In certain embodiments, the semipermeable membrane comprises cellulose acetate and a pore former comprising poloxamer. In certain embodiments, the weight ratio of cellulose acetate to poloxamer is between about 80:20 and about 99.5:0.5. In certain embodiments, the weight ratio of cellulose acetate and pore former affects variability in lag time. In certain embodiments, variability in lag time decreases with increasing the amount of pore former in the membrane. In certain embodiments, lag time decreases with increasing the amount of pore former in the membrane. In certain embodiments, the ratio of cellulose acetate and pore former is optimized to obtain a desired lag time with minimal variability. In certain embodiments, the weight ratio of cellulose acetate and pore former is about 80:20, about 85:15, about 90:10, about 95:5, about 96:4, about 97:3, about 98:2, about 99:1, about 99.5:0.5, or any intermediate values therein.

In certain embodiments, the semipermeable membranes include one or more plasticizers. Plasticizers play a significant role in adjusting flexibility and permeability of the semipermeable membrane. Plasticizers change the viscoelastic behavior and permeability of the polymer present in the semipermeable membrane. Plasticizers can convert a hard and brittle polymer into a softer and more pliable material that has more mechanical strength. Plasticizers used in the semipermeable membranes comprise, but are not limited to, polyethylene glycols, triethyl citrate, triacetin, diethyl tartrate, dibutyl sebacate, and combinations thereof. In certain embodiments, coating solvents used for coating comprise, but are not limited to, methylene chloride, carbon tetrachloride, acetone, methanol, ethanol, water, and/or any mixtures thereof. In certain embodiments, the coating solvent is a mixture of acetone and water. In certain embodiments, the acetone: water weight ratio is between 80:20 and 95:5. In certain embodiments, the acetone: water weight ratio is about 80:20, about 85:15, about 90:10, about 95:5, or any intermediate values therein.

In certain embodiments, the programmable osmotic-controlled oral compositions of the disclosure include an aesthetic coat over the semipermeable membrane. In certain embodiments, the aesthetic coat comprises colors, flavors, and sweeteners. In certain embodiments, the aesthetic coat is the outermost coat comprising OPADRY® II for pigmentation or OPADRY® clear for final glossiness.

6.3 Embodiments of the Dosage Form

In certain embodiments, additional programmable osmotic-controlled compositions containing additional pull layers, IR coatings, etc. are contemplated. A nonlimiting set of exemplary osmotic-controlled compositions follows.

In certain embodiments, the programmable osmotic-controlled compositions of the disclosure provide delayed extended release of methylphenidate. In certain embodiments, the programmable osmotic-controlled compositions of the disclosure comprise a multilayer tablet core coated with a semipermeable membrane containing at least one orifice. In certain embodiments, the tablet core comprises multiple layers in the following order: a placebo layer in continuity with the at least one orifice present in the semipermeable membrane, a delayed extended release layer containing methylphenidate, and a push layer, wherein the push layer is away (e.g., furthest away) from the orifice in the semipermeable membrane. In certain embodiments, the methylphenidate is methylphenidate hydrochloride. In certain embodiments, the number of orifices in the semipermeable membrane can be two, three, or four. In certain embodiments, the optimum orifice diameter is about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, from about 0.6 mm to about 1.2 mm, from about 0.6 mm to about 1.1 mm, from about 0.6 mm to about 1.0 mm, from about 0.6 mm to about 0.9 mm, from about 0.6 mm to about 0.8 mm, from about 0.7 mm to about 1.2 mm, from about 0.8 mm to about 1.2 mm, from about 0.9 mm to about 1.2 mm, from about 1.0 mm to about 1.2 mm, from about 1.1 mm to about 1.2 mm, from about 0.7 mm to about 1.1 mm, or from about 0.8 mm to about 1.0 mm. In certain embodiments, the semipermeable membrane facing the top of the placebo layer is completely removed to provide an orifice comprising an optimum diameter that is equivalent to the diameter of the top of the placebo layer end of the multilayer core.

In certain embodiments, the programmable osmotic-controlled composition of the disclosure comprises a combination composition providing an immediate release of a sedative and a delayed extended release of methylphenidate. In certain embodiments, the programmable osmotic-controlled composition of the disclosure comprises a multilayer tablet core coated with a semipermeable membrane containing an orifice, and a coating of a sedative for immediate release, over the semipermeable membrane. In certain embodiments, the methylphenidate is methylphenidate hydrochloride.

In certain embodiments, the programmable osmotic-controlled composition of the disclosure is a combination composition providing an immediate release of a sedative, followed by an extended release of a sedative, followed by a delayed extended release of methylphenidate. In certain embodiments, the programmable osmotic-controlled composition of the disclosure comprises an IR coat containing a sedative, a seal coat below the IR sedative coat, an ER coat containing a sedative and below the seal coat, a cellulose acetate coat containing an orifice and placed below the ER sedative coat, a placebo layer facing the orifice, a delayed extended release layer containing methylphenidate and placed below the placebo layer, and a push layer placed below the delayed extended release layer and facing away from the orifice. In certain embodiments, the methylphenidate is methylphenidate hydrochloride.

In certain embodiments, the programmable osmotic-controlled compositions of the disclosure comprise a combination composition providing immediate release of a sedative and a chrono release of a stimulant. In certain embodiments, the composition comprises a multilayer tablet core coated with a semipermeable membrane containing an orifice, and a coating of a drug for immediate release over the semipermeable membrane. In certain embodiments, the multilayered tablet core comprises a push layer, and a pull layer. In certain embodiments, the pull layer comprises a placebo layer, and an active layer containing a stimulant. In certain embodiments, the active layer comprises an immediate release layer and an extended release layer for providing chrono release of the stimulant. In certain embodiments, the tablet core comprises multiple layers in the following order: a placebo layer facing the orifice in the semipermeable membrane, a delayed immediate release layer containing a stimulant, a delayed extended release layer containing a stimulant, and a push layer, wherein the push layer is furthest away from the orifice in the semipermeable membrane. In certain embodiments, the delayed immediate release layer and the delayed extended release layer contain methylphenidate or a pharmaceutically acceptable salt thereof. In certain embodiments, the methylphenidate is methylphenidate hydrochloride.

In certain embodiments, the programmable osmotic-controlled compositions of the disclosure comprise a combination composition providing an immediate release of a sedative and a delayed chrono release of a stimulant, wherein the immediate release sedative is present as an immediate release layer in the tablet core. In certain embodiments, the tablet core comprises multiple layers in the following order: an immediate release layer containing a sedative and facing the orifice in the semipermeable membrane, a placebo layer, a delayed immediate release layer containing a stimulant, a delayed extended release layer containing a stimulant, and a push layer, facing away from the orifice. In certain embodiments, the delayed immediate release layer and the delayed extended release layer contain methylphenidate or a pharmaceutically acceptable salt thereof. In certain embodiments, the methylphenidate is methylphenidate hydrochloride. Salt forms of methylphenidate are prone to degradation and often have stability and shelf-life problems. Addition of a stabilizing agent, e.g. a pH-adjusting agent, to the composition decreases undesired degradation and improves product stability. In certain embodiments, the programmable osmotic-controlled methylphenidate compositions of the disclosure include a stabilizing agent to minimize the degradation of methylphenidate. In certain embodiments, the stabilizing agent comprises, but not limited to, succinic acid, potassium phosphate, sodium phosphate, fumaric acid, citric acid, tartaric acid, malic acid, hydrochloric acid, aspartic acid, glutamic acid, oxalic acid, lactic acid, malonic acid, glyceric acid, ascorbic acid, and any combination thereof. In certain embodiments, methylphenidate hydrochloride is stable without the presence of a stabilizing agent.

In certain embodiments, the programmable osmotic-controlled compositions of the disclosure comprise a combination composition providing an immediate release of a sedative and a delayed increasing (gradient) release of a stimulant. In certain embodiments, the composition comprises a multilayer tablet core coated with a semipermeable membrane containing an orifice. In certain embodiments, the tablet core comprises multiple layers in the following order: a placebo layer facing the orifice in the semipermeable membrane, at least two delayed release layers comprising a stimulant for delayed release, and a push layer, wherein the at least two delayed release layers releases the stimulant over a period of at least two successive intervals, wherein more stimulant is released in the second interval compared to the first interval. In certain embodiments, the stimulant is methylphenidate or a pharmaceutically acceptable salt thereof. In certain embodiments, the methylphenidate is methylphenidate hydrochloride.

In certain embodiments, the seal coat comprises hydroxypropyl methyl cellulose (HPMC), hydroxypropyl cellulose, hydroxyethyl cellulose, or povidone. In certain embodiments, the seal coat is present in an amount of from about 1 wt % to about 20 wt %, from about 5 wt % to about 20 wt %, or from about 5 wt % to about 15 wt %, based on the weight of the tablet core weight without seal coat.

In certain embodiments, the exemplary clinical situation described herein involves treatment of ADHD/ADD with a delayed release stimulant therapy. Accordingly, the present disclosure also pertains to making oral methylphenidate delayed release dosage forms that provide a delayed release of methylphenidate hydrochloride over an extended time period.

6.4 Features of the Dosage Form

The present disclosure provides programmable osmotic-controlled oral compositions that provide a delayed controlled release of a stimulant and can be programmed to release the stimulant after the delay period, with complete drug recovery. The osmotic-controlled oral compositions of the disclosure can be programmed to control lag time during the delay period and release the stimulant at a desired rate after the delay period. In certain embodiments, the osmotic-controlled oral compositions are programmed to provide a precise lag time of at least about 4, 5, 6, 7, 8, 9, 10, 11, 12 hours, or intermediate time periods within the range. In certain embodiments, the programmable osmotic-controlled oral compositions of the disclosure provide a delayed extended release, or a delayed chrono release of methylphenidate/methylphenidate hydrochloride. The programmable osmotic-controlled oral compositions of the disclosure provide pH-independent release of methylphenidate/methylphenidate hydrochloride at an osmotically determined rate for an extended time period, even as the dosage form transits the GI tract and encounters variable hydrodynamic environments of the GI tract, as well as microenvironments with significantly different pH values. In certain embodiments, the programmable osmotic-controlled oral compositions of the disclosure provide delayed controlled release of methylphenidate/methylphenidate hydrochloride, with minimum variability in lag time with varying pH and hydrodynamic conditions of a dissolution medium or the human GI tract.

In certain embodiments, the minimal variability in lag time comprises variability of not more than about 30%, not more than about 29%, not more than about 28%, not more than about 27%, not more than about 26%, not more than about 25%, not more than about 24%, not more than about 23%, not more than about 22%, not more than about 21%, not more than about 20%, not more than about 19%, not more than about 18%, not more than about 17%, not more than about 16%, not more than about 15%, not more than about 14%, not more than about 13%, not more than about 12%, not more than about 11%, not more than about 10%, not more than about 9%, not more than about 8%, not more than about 7%, not more than about 6%, not more than about 5%, not more than about 4%, not more than about 3%, not more than about 2%, not more than about 1%, or any intermediate values therein, with variations in pH, presence or absence of food, gastric motility, or viscosity of dissolution medium.

In certain embodiments, the minimal variability in lag time comprises variability of from 0% to about 30%, from 0% to about 29%, from 0% to about 28%, from 0% to about 27%, from 0% to about 26%, from 0% to about 25%, from 0% to about 24%, from 0% to about 23%, from 0% to about 22%, from 0% to about 21%, from 0% to about 20%, from 0% to about 19%, from 0% to about 18%, from 0% to about 17%, from 0% to about 16%, from 0% to about 15%, from 0% to about 14%, from 0% to about 13%, from 0% to about 12%, from 0% to about 11%, from 0% to about 10%, from 0% to about 9%, from 0% to about 8%, from 0% to about 7%, from 0% to about 6%, from 0% to about 5%, from 0% to about 4%, from 0% to about 3%, from 0% to about 2%, or from 0% to about 1%.

In certain embodiments, the programmable osmotic-controlled oral compositions of the disclosure provide a delayed extended release of methylphenidate hydrochloride. In certain embodiments, the timing of administration of the composition is titrated to optimize the tolerability and efficacy of the dose, as seen during the next morning and throughout the day. In certain embodiments, the osmotic-controlled oral compositions of methylphenidate hydrochloride are programmed to provide the drug release as follows: a lag time of at least about, e.g., 6-8 hours; a controlled release comprising about 15% to about 20% of drug release in about 1-4 hours after the lag time; a drug absorption window of about 1-2 hours; and an extended release of the drug with at least 95% drug recovery in about 10-12 hours after the lag time (or about 22 hours from the time of administration of the composition). In certain embodiments, the composition releases no more than 20% of the methylphenidate hydrochloride during the lag time. In certain embodiments, the composition releases no more than 10% of the methylphenidate hydrochloride during the lag time. In certain embodiments, the disclosure provides programmable osmotic-controlled oral compositions of methylphenidate hydrochloride that can be programmed to limit the amount of methylphenidate hydrochloride in plasma to less than 20 wt %, e.g., less than about 10 wt %, of the maximum concentration ($C_{max}$) during the lag time and beginning about 22 hours after the time of administration, to avoid side effects, e.g., insomnia.

The programmable osmotic-controlled oral compositions of the disclosure comprise a multilayer tablet core comprising methylphenidate hydrochloride, wherein the core is coated with a semipermeable membrane comprising an orifice and, optionally, an immediate release drug layer coating/immediate release drug layer, comprising a sedative for immediate release, over the semipermeable membrane. In certain embodiments, the multilayer tablet core comprises a push layer and a pull layer. In certain embodiments, the pull layer comprises a placebo layer and an active layer. In certain embodiments, the placebo layer comprises at least one wicking agent and/or an osmogen, and at least one polyethylene oxide polymer having an average molecular weight of from about 300,000 Da to about 900,000 Da. In certain embodiments, the active layer comprises methylphenidate hydrochloride for delayed extended release, a wicking agent, and at least one polyethylene oxide polymer having a molecular weight of between about 100,000 Da and about 300,000 Da. In certain embodiments, the push layer comprises at least one polyethylene oxide polymer having an average molecular weight of greater than or equal to 1000,000 Da, and at least one osmogen. In certain embodiments, the semipermeable membrane contains at least one orifice facing the placebo layer end of the core. In certain embodiments the active layer is substantially free of sodium chloride. In certain embodiments, the active layer contains a weight ratio of methylphenidate or a pharmaceutically acceptable salt thereof: polyethylene oxide of between about 20:60 and about 70:30. In certain embodiments, the active layer contains a weight ratio of methylphenidate or a pharmaceutically acceptable salt thereof: polyethylene oxide ratio of between about 20:60 and about 60:40. In certain embodiments, the osmogen in the push layer is present in an amount of from about 5 wt % to about 40 wt %, e.g., from about 10 wt % to about 30 wt %, based on the total weight of the push layer.

In certain embodiments, the lag time and release rate of the osmotic-controlled oral compositions of the disclosure does not substantially depend upon the pH of the dissolution medium. FIG. 12 shows a comparison of lag time and dissolution profiles of Tablet 34 in about 900 ml of about 0.01N HCl, pH 4.5 acetate buffer, and pH 6.8 phosphate buffer, using USP II (sinkers) at 50 rpm and 37° C. FIG. 12 shows effect of pH on lag time in a tablet with a drug to polymer weight ratio of about 30:70. Figure12 demonstrates that the tablets exhibit minimal variability in lag time with variations in pH of the dissolution medium.

Similarly, FIG. 14 compares the dissolution profiles of Tablet 37 in about 0.01N HCl, in a pH 4.5 acetate buffer, and in a pH 6.8 phosphate buffer, using USP II (sinkers) at 50 rpm and 37° C. FIG. 14 demonstrates that the tablets exhibit minimal variability in lag time with variations in pH of the dissolution medium.

In certain embodiments, the compositions of the disclosure exhibit minimal variability in lag time with variations in the viscosity of the dissolution medium. FIG. 15 compares dissolution profiles of Tablet 37 in dissolution mediums with different viscosities, e.g., with and without hydroxypropyl methyl cellulose, using USP II (sinkers) at 50 rpm and 37° C. The figure demonstrates that Tablet 37 exhibits minimal variability in lag time with variations in viscosity of the dissolution medium.

In certain embodiments, the lag time and release rate of the osmotic-controlled oral compositions of the disclosure is independent of the hydrodynamics of the dissolution medium. FIG. 16 shows a comparison of lag time and dissolution profiles of Tablet 37 using USP methods simulating hydrodynamic conditions of the GI tract-about 900 ml of about 0.01N HCl, using USP II (sinkers) at 50 rpm and 37° C.; and in about 900 ml of about 0.01N HCl, using USP III (BioDis) at 25 dpm and 37° C. FIG. 16 demonstrates that there is no substantial change in the lag time and release rate with changing hydrodynamics of the dissolution medium.

In certain embodiments, the programmable osmotic-controlled oral compositions of the disclosure are programmed to obtain a desired lag time by adjusting the composition of the placebo layer and/or the push layer, e.g., the amount and/or molecular weight/grade of the polyethylene oxide polymer (e.g., POLYOX®) in the placebo layer and/or the push layer, the coating composition of the semipermeable membrane, and/or the coating level of the semipermeable membrane.

In certain embodiments, the placebo layer provides a desired lag time by delaying the release of methylphenidate in the environment of use. In certain embodiments, the lag time depends upon the placebo layer amount that must be displaced by the expanding push layer. In certain embodiments, the lag time depends upon the molecular weight/grade of the POLYOX® (e.g., POLYOX® grade) present in the placebo layer. In certain embodiments, the lag time increases with increasing the molecular weight/grade of the POLYOX® present in the placebo layer. In certain embodiments, the lag time increases as the amount of POLYOX® in the placebo layer increases. FIG. 18 demonstrates that compositions with placebo layers containing POLYOX®, with an average molecular weight of at least about 300,000 Da, provide a lag time of at least about 6 hours.

In certain embodiments, the placebo layer amount can affect the lag time. In certain embodiments, compositions containing higher amount of placebo layer show longer lag time compared to compositions containing lower amounts of placebo layer. Tablets 45 contained about 32 wt % (about 122 mg) of placebo layer and Tablet 54 contained about 42 wt % (about 200 mg) of placebo layer, based on the total weight of the uncoated tablet core. FIG. 26 demonstrates that lag time increases with increasing weight of the placebo layer, e.g., Tablet 45 exhibits a lag time of about 5 hours, and Tablet 54 exhibits a lag time of about 7 hours. In certain embodiments, the compositions containing POLYOX® 205 in the placebo layer provide a lag time of about 5 hours when the uncoated tablet core includes about 35% of placebo layer.

In certain embodiments, the compositions containing POLYOX® 205 in the placebo layer provide a lag time of about 6 hours at about 35 wt % of the placebo layer, based on the total weight of the uncoated tablet core, e.g., Tablet 50.

In certain embodiments, the compositions containing POLYOX® 205 in the placebo layer provide a lag time of about 7 hours at about 42 wt % of the placebo layer, based on the total weight of the uncoated tablet core, e.g., Tablet 54.

In certain embodiments, the compositions containing POLYOX® 205 in the placebo layer provide a lag time of about 8 hours at 48 wt % of the placebo layer, based on the total weight of the uncoated tablet core, e.g., Tablet 55. In certain embodiments, the lag time does change substantially with the push layer amount.

FIG. 13 shows that programmable osmotic-controlled oral compositions of the disclosure containing POLYOX® 1105 in the placebo layer and containing a drug to polymer weight ratio of about 40:60, do not show any change in lag time, with a change the amount of the push layer. In certain embodiments, the amount of the push layer is changed by changing the amount of sodium chloride/osmogen and/or the amount of POLYOX® in the push layer.

In certain embodiments, the placebo layer contains a wicking agent and/or an osmogen. In certain embodiments, it was observed that presence of a wicking agent and an osmogen together in the placebo layer reduces tablet-to-tablet content uniformity. In certain embodiments, the placebo layer contains at least one osmogen. In certain embodiments, the placebo layer contains no wicking agent. In certain embodiments, the compositions containing an osmogen and without any wicking agent in the placebo layer, improves tablet-to-tablet content uniformity.

In certain embodiments, the release rate and drug recovery of the osmotic-controlled oral compositions of the disclosure depends upon the drug: polymer weight ratio in the active layer. In certain embodiments, the release rate and drug recovery increases with increasing drug: polymer weight ratio. FIG. 7 shows the effect of drug to polymer weight ratio in the active layer on dissolution profiles of various tablets placed in about 900 ml of about 0.01N HCl, using USP II (sinkers) at 50 rpm and 37° C. Active layer in Tablet 22 contained a drug to polymer weight ratio of about 20:80. Active layer in Tablet 23 contained a drug to polymer weight ratio of about 30:70. FIG. 7 demonstrates that release rate, and drug recovery is improved with increasing drug to polymer weight ratio in the active layer. FIG. 26 provides dissolution profiles of Tablets 45, 54A, 54B, 55A, and 55B.in 50 ml of pH 6.8 buffer, using USP Apparatus II (Sinkers), at 5 rpm and 37° C. Tablets 45 and 54A, 54B, and 57 contained a drug: polymer weight ratio in the active layer of about 40:60; Tablets 55 A and 55B contained a drug: polymer weight ratio in the active layer of about 60:40; and Tablet 56 contained a drug: polymer weight ratio in the active layer of about 50:50. FIG. 26 demonstrates that the drug: polymer weight ratio affects the release rate, e.g., compositions with higher drug: polymer weight ratio provide faster release rate compared to compositions with lower drug: polymer weight ratio.

In certain embodiments, the presence of sodium chloride in the active layer increases the rate of hydration of POLYOX® in the active layer and improves drug recovery without changing the lag time. FIG. 8 demonstrates that programmable osmotic-controlled oral compositions of the disclosure containing POLYOX® 1105 in the placebo layer show no change in lag time with or without the presence of sodium chloride in the active layer. Tablet 24 contained sodium chloride in the active layer. Tablet 25 did not contain any amount of sodium chloride in the active layer. FIG. 8 demonstrates that presence of sodium chloride in the active layer improves drug recovery by about 5%, compared to tablets without sodium chloride in the active layer.

In certain embodiments, presence of wicking agent in the active layer increases release rate without affecting lag time. FIG. 20 compares dissolution profiles of Tablets 45, 48, and 49. Tablet 45 with 10% coating weight gain and 48 with 12.5% coating weight gain contained a wicking agent and no sodium chloride/osmogen in the active layer. Tablet 49 with 12.5% coating weight gain contained sodium chloride and no wicking agent in the active layer. The figure demonstrates that the presence of a wicking agent and absence of sodium chloride in the active layer increases the release rate, without affecting lag time.

In certain embodiments, the presence of osmogen/sodium chloride in the push layer affects lag time, release rate, and/or drug recovery of the composition. In certain embodiments, increasing the amount of osmogen in the push layer reduces lag time and improves release rate and drug recovery. In certain embodiments, increasing the amount of osmogen in the push layer increases ingress of water in the push layer. In certain embodiments, the increased ingress of water in the push layer results in increased hydration and gelling of POLYOX® present in the push layer, which increases the release rate and drug recovery from the composition. In certain embodiment, the push layer contains osmogen in an amount of from about 10 wt % to about 30 wt %, based on the total weight of the push layer, to provide a lag time of about 6 hours to about 8 hours. FIG. 9 shows the effect of sodium chloride in the push layer on lag time and drug recovery. FIG. 9 compares dissolution profiles of the tablets 23, 26, 27, and 28 in about 900 ml of about 0.01N HCl, using USP II (sinkers) at 50 rpm and 37° C. Tablet 28 contains no sodium chloride in the push layer; Tablet 23 contains about 10 wt % of sodium chloride, based on the total weight of the push layer; Tablet 27 contains about 18 wt % of sodium chloride, based on the total weight of the push layer; and Tablet 26 contains about 25 wt % of sodium chloride, based on the total weight of the n push layer. FIG. 9 demonstrates that presence of sodium chloride in push layer reduces lag time and improves release rate and drug recovery, when compared with compositions without any sodium chloride in the push layer. FIG. 9 further demonstrates that increasing the amount of sodium chloride in the push layer reduces lag time.

In certain embodiments, the POLYOX® grade in the push layer affects drug recovery and release profile of the composition. FIG. 19 compares the release rate and drug recovery of compositions containing POLYOX® WSR 303 (7M), POLYOX® WSR 301 (3M), and POLYOX® WSR Coagulant (5M) in the push layer. Tablet 38 contained POLYOX® 1105 in the placebo layer and POLYOX® WSR 303 in the push layer; Tablet 43 contained POLYOX® N750 in the placebo layer and POLYOX® WSR 301 in the push layer; and Tablet 44 contained POLYOX® N80 in the placebo layer and POLYOX® WSR Coagulant in the push layer. FIG. 19 demonstrates that compositions containing POLYOX® 303 in the push layer provide faster release profiles and lower drug recovery, compared to compositions containing POLYOX® WSR 301 or POLYOX® WSR Coagulant in the push layer.

In certain embodiments, the lag time and drug recovery depend upon the membrane composition and coating weight gain/coating level of the semipermeable membrane. In certain embodiments, the lag time increases with increasing the coating weight gain/coating level of the semipermeable membrane. In certain embodiments, drug recovery is reduced, and lag time is increased with increasing coating weight gain of the semipermeable membrane. In certain embodiments, the semipermeable membrane comprises at least one water-insoluble polymer and a pore former. In certain embodiments, the membrane comprises cellulose acetate (CA) and polyethylene glycol (e.g., PEG 3350) with a CA to PEG weight ratio of between about 80:20 and about 99.5:0.5. In certain embodiments, the membrane comprises OPADRY® CA with CA: PEG weight ratio of about 90:10, about 95:5 or about 98:2. In certain embodiments, increasing the amount of cellulose acetate in the membrane reduces drug recovery and increases lag time. FIG. 10 shows the effect of the cellulose acetate to polyethylene glycol weight ratio in the semipermeable membrane on lag time and drug recovery of the tablets with 15% coating weight gain. FIG. 10 compares dissolution profiles of Tablets 29 and 30 in about 900 ml of about 0.01N HCl, using USP II (sinkers) at 50 rpm and 37° C. Tablet 29 contained OPADRY® CA with CA:PEG ratio of about 95:5; and Tablet 30 contained OPADRY® CA with CA:PEG ratio of about 98:2. FIG. 10 demonstrates that increasing the amount of cellulose acetate in the membrane, at a same coating weight gain, increases lag time and reduces drug recovery.

FIG. 20 provides dissolution profiles of Tablets 45, 48, and 49 in 5 ml of pH 6.8 buffer, using USP Apparatus II (Sinkers), at 5 rpm and 37° C. (low-volume, low-RPM condition). FIG. 20 demonstrates that Tablet 45, with about 10% coating weight gain, provides an improved release rate and improved drug recovery compared to Tablets 48 and 49, with about 12.5% coating weight gain. FIG. 20 further demonstrates that Tablet 48 containing OPADRY® CA clear (90:10)) in the coating layer provides faster drug release compared to Tablet 49 containing OPADRY® CA clear (95:5), at a same coating weight gain.

In certain embodiments, the size and number of orifices affects % relative standard deviation (% RSD) among tablets. Example 27/Table 27 provides % relative standard deviation (% RSD) for Tablet 45 containing a coating with one orifice with 0.6 mm diameter; Tablet 45 containing a coating with two orifices, each with 0.6 mm diameter; and Tablet 45 containing a coating with one orifice with 1.2 mm diameter. The table shows that Tablet 45 containing two orifices, each with 0.6 mm diameter; and Tablet 45 containing one orifice with 1.2 mm diameter show significantly reduced % RSD among a set of three tablets, compared to Tablet 45 containing one orifice with 0.6 mm diameter.

6.5. Methods of Treatment

In certain embodiments, the programmable osmotic-controlled compositions of the disclosure provide delayed release of a stimulant are used for the treatment of ADHD/ADD. Treatment of ADHD/ADD with stimulants helps to reduce symptoms of these and other attention disorders, and improve self-esteem, cognition, and social and family interactions of the patient. The most commonly prescribed medications for ADHD/ADD include mixed amphetamines and methylphenidate. These medications provide calming and focusing effects on an individual suffering from ADHD/ADD. Methylphenidate is a central nervous system (CNS) stimulant approved by the FDA in 1955 for hyperactivity. The compositions described herein can include methylphenidate in a racemic mixture of dextro and levo conformations or as a pure dextro isomer. The use of pharmaceutically acceptable salts of methylphenidate, such as methylphenidate hydrochloride, is also contemplated in the present disclosure.

In certain embodiments, the disclosure provides programmable osmotic-controlled compositions of methylphenidate hydrochloride that are administered at night, e.g., before bedtime, and deliver a therapeutic amount of methylphenidate hydrochloride in a delayed extended release pattern in order to maintain a constant release of a therapeutic amount of methylphenidate hydrochloride throughout the active periods of the day, including upon waking. In certain embodiments, the composition provides a delayed chrono release of methylphenidate hydrochloride.

In certain embodiments, the disclosure provides therapeutic compositions and methods for treatment of ADD, ADHD, or other attention disorder conditions responsive to CNS stimulants. In certain embodiments, the disclosure provides a method of treating attention disorders in children, comprising administering to a child in need thereof a programmable osmotic-controlled composition of the disclosure providing an immediate release of a sedative, and a delayed and extended release of a CNS stimulant. The immediate release of a therapeutic amount of sedative helps the child sleep during the night, and a delayed and extended release of a therapeutic amount of a CNS stimulant keeps the child alert throughout the active periods of the day, including when the child is waking up. In certain embodiments, the release of stimulant is delayed for at least about 6 hours followed by an extended release or a chrono release of the stimulant. In certain embodiments, the delayed release of the stimulant is delayed chrono release. In certain embodiments, the delayed chrono release is delayed immediate release and a delayed extended release of the stimulant. In certain embodiments, the sedative is clonidine, diphenhydramine, guanfacine, or melatonin. In certain embodiments, the CNS stimulant is methylphenidate hydrochloride. In certain embodiments, the composition is administered before the child goes to bed. In particular, for pediatric patients with ADHD/ADD, once daily doses of such osmotic-controlled oral compositions of the disclosure at bedtime providing an immediate release of a sedative, e.g., clonidine, guanfacine, diphenhydramine, melatonin, for promoting sedation during nighttime, followed by delayed extended release or chrono release of a CNS stimulant, e.g., methylphenidate, that starts working in the morning and lasts during the daytime, addresses problems of insomnia during night, while keeping the child alert and attentive during the day when the child is in school or engaged in activities. In certain embodiments, the release of methylphenidate is delayed for at least 4 hours, at least 5 hours, at least 6 hours, at least 7 hours, at least 8 hours, at least 9 hours, at least 10 hours, at least 11 hours, at least 12 hours, or any intermediate periods. The composition provides a suitable lag time such that the sedative is effective during the sleep time of the patient, and the stimulant is effective during the day.

In certain embodiments, the disclosure provides programmable osmotic-controlled methylphenidate compositions providing improved patient compliance and convenience. The compositions provide clinical benefits of delivering methylphenidate hydrochloride in a delayed and extended manner, independent of drug chemical properties, patient physiological factors, and food. In certain embodiments, the disclosed compositions provide a timed, prolonged therapeutic effect when taken once a day. The programmable osmotic-controlled methylphenidate compositions of the disclosure provide food-independent delayed release that can avoid early morning dosing of methylphenidate hydrochloride stimulant to children suffering from ADHD/ADD. The compositions can be administered, with or without food, at night, before bedtime, for example but not limited to 8:00 pm, and provide delayed controlled release of a stimulant, e.g., methylphenidate hydrochloride. In certain embodiments, the osmotic-controlled compositions of methylphenidate hydrochloride avoid insomnia by limiting residual amount of methylphenidate hydrochloride in plasma to less than 10% of the maximum concentration ($C_{max}$) during the lag time (e.g., the daily lag time) and after the complete recovery period.

In certain embodiments, the disclosure provides programmable osmotic-controlled compositions for treating diseases or conditions comprising, but not limited to, attention deficit disorder (ADD) and attention deficit hyperactive disorder (ADHD). Typically, stimulant-based medications for ADHD/ADD are dosed two hours prior to beginning an early morning routine, with an onset of treatment effect usually about two hours after administration. Such medications require twice-daily administration and cause compliance issues. The compositions of the disclosure avoid the need of early morning dosing that requires an onset time of about two hours and improve the symptoms of a condition in the early morning and throughout the day. Early morning symptom control while getting the children ready for school, is a major challenge for parents and caregivers of children suffering from ADHD/ADD. The programmable osmotic-controlled compositions of the disclosure provide a convenient method of administration in that a single dose can be taken (typically in the evening prior to going to bed, or at whatever time of the day one retires for an extended period of sleep) and the release of drug is delayed for at least about 4 hours, e.g., about 6-12 hours.

The compositions can be administered, with or without food, at night, before bedtime and provide a delayed release of the stimulant. In certain embodiments, the compositions of the disclosure provide minimal variability in lag time in various hydrodynamic conditions and pH (both conditions and regions) of the GI tract. In certain embodiments, the timing of administration is titrated to optimize the tolerability and efficacy the next morning and throughout the day.

6.6. Methods of Manufacture

In certain embodiments, the pull layer and the push layer in the multilayer programmable osmotic-controlled compositions of the disclosure comprise granules made by wet granulation. In certain embodiments, wet granulation comprises mixing of intragranular ingredients into a pre-blend, addition of liquid to the pre-blend for wetting of the pre-blend and formation of granules, milling for deagglomeration of granules, and drying and screening of the resulting granules.

In certain embodiments, the placebo layer comprises a placebo layer blend comprising placebo layer granules and extragranular excipients. In certain embodiments, the placebo layer granules comprise a swellable hydrophilic polymer, a binder, an osmogen, a stabilizer, and a color pigment. In certain embodiments, granules further include a wicking agent. In certain embodiments, glidant and lubricant are present as extragranular excipients in the placebo layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol: water ratio of between about 60:40 and about 99:1 by weight. In certain embodiments, granules are dried, milled, blended with extragranular excipients, and compressed into the placebo layer blend. In certain embodiments, the placebo layer is made by dry granulation/slugging. In certain embodiments, the placebo layer is made by direct compaction In certain embodiments, active layer blend comprises active layer granules and extragranular excipients. In certain embodiments, the active layer granules comprise methylphenidate or a pharmaceutically acceptable salt thereof, a swellable hydrophilic polymer, a binder, an osmogen, a stabilizer, and a color pigment. In certain embodiments, granules further include a surfactant and/or a wicking agent. In certain embodiments, glidant and lubricant are present as extragranular excipients in the active layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol: water ratio of between about 60:40 and about 99:1 by weight. In certain embodiments, granules are dried, milled, blended with extragranular excipients, and compressed into the active layer blend. In certain embodiments, the active layer is made by dry granulation/slugging. In certain embodiments, the active layer is made by direct compaction.

In certain embodiments, the push layer blend comprises push layer granules and extragranular excipients. In certain embodiments, the push layer granules comprise a swellable hydrophilic polymer, a binder, an osmogen, a stabilizer, and a color pigment. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol: water ratio of between about 60:40 and about 99:1 by weight. In certain embodiments, granules are dried, milled, blended with extragranular excipients, and compressed into the push layer blend. In certain embodiments, the push layer is made by dry granulation/slugging. In certain embodiments, the push layer is made by direct compaction.

In certain embodiments, the placebo layer blend, the active layer blend, and the push layer blend are filled into a tablet dye and compressed into a trilayer tablet core. The resulting tablet core is coated with a semipermeable membrane coat followed by laser drilling of an orifice in the coating, and, optionally, coating of an immediate release drug layer/coat over the semipermeable membrane layer/coat. In certain embodiments, the immediate release drug layer contains a sedative. In certain embodiments, the sedative is selected from the group consisting of clonidine, diphenhydramine, guanfacine, melatonin, or pharmaceutically acceptable polymorphs, salts, solvates, and hydrates thereof. In certain embodiments, the semipermeable membrane coat includes a water-soluble pore former. In certain embodiments, the water-soluble pore former is a water-soluble plasticizer, e.g., PEG 400, PEG 1000, PEG 1450, PEG 3350. In certain embodiments, the immediate release layer is further coated with an over coat. In certain embodiments, there is a seal coat between the semipermeable membrane and the immediate release drug layer comprising drug for immediate release. In certain embodiments, coating solvents used for coating comprise, but are not limited to, methylene chloride, carbon tetra chloride, acetone, methanol, ethanol, water, and/or any mixtures thereof. In certain embodiments, the coating solvent is a mixture of acetone and water. In certain embodiments, the acetone: water weight ratio is between 80:20 and 95:5. In certain embodiments, the acetone: water weight ratio is about 80:20, about 85:15, about 90:10, about 95:5, or any intermediate values therein. In certain embodiments, the solvents used for coating the semipermeable membrane include a mixture of acetone and water, wherein the film porosity increases with increasing water content In certain embodiments, the semipermeable membrane is a polymeric film coating containing at least one orifice/hole/delivery port for drug release. In certain embodiments, size of the orifice must be optimized to control drug release from the dosage form. The size of orifice should not be too large to allow solute diffusion from the orifice into the core, and not too small to build hydrostatic pressure within the core.

In certain embodiments, the orifice is made via manual or laser drilling. In certain embodiments, the optimum orifice diameter is less than about 2.0 mm. In certain embodiments, the optimum orifice diameter is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, or any intermediate values therein. In certain embodiments, the optimum orifice diameter is equivalent to the diameter of the top of placebo layer end of the tablet core coated with the semipermeable membrane. In certain embodiments, it is important that the semipermeable membrane is adequately perforated with an orifice without compromising the integrity of the tablet core.

The following examples illustrate the disclosure in a nonlimiting manner. Unless indicated to the contrary, the numerical parameters set forth herein can vary depending upon the desired properties sought to be obtained by the present disclosure.

7. EXAMPLES

The following examples are merely illustrative of the presently disclosed subject matter and should not be considered as limiting the scope of the subject matter in any way.

Example 1

Preparation of Delayed Extended Release Methylphenidate HCl Tablet Compositions The present Example provides various formulations for delayed extended release methylphenidate HCl tablets as outlined in Table 1 and Table 2. Six different tablets were prepared.

TABLE 1

Delayed Extended Release Methylphenidate HCl Tablets

| Composition | Tablet 1 mg/dose | Tablet 2 mg/dose | Tablet 3 mg/dose |
|---|---|---|---|
| Placebo layer | | | |
| Polyethylene oxide (POLYOX ® N80) | NA | 75.00 | NA |
| Polyethylene oxide (POLYOX ® 750) | 75.00 | NA | 75.00 |
| Povidone (KOLLIDON ® 30 LP) | 8.00 | 8.00 | 8.00 |
| Succinic acid | 3.00 | 3.00 | 3.00 |
| Stearic acid | 0.90 | 0.90 | 0.90 |
| Butylated hydroxytoluene | 0.10 | 0.10 | 0.10 |
| Active layer 1 | | | |
| Methylphenidate HCl | 10.80 | 10.80 | NA |
| Polyethylene oxide (POLYOX ® N80) | 54.00 | 54.00 | NA |
| Povidone (KOLLIDON ® 30 LP) | 4.00 | 4.00 | NA |
| Succinic acid | 1.10 | 1.10 | NA |
| Stearic acid | 0.05 | 0.05 | NA |
| Butylated hydroxytoluene | 0.05 | 0.05 | NA |
| Active layer 2 | | | |
| Methylphenidate HCl | 43.20 | 43.20 | 54.00 |
| Polyethylene oxide (POLYOX ® N80) | 149.0 | 149.0 | 207.0 |
| Povidone (KOLLIDON ® 30 LP) | 7.00 | 7.00 | 8.00 |
| Succinic acid | 3.00 | 3.00 | 3.00 |
| Stearic acid | 0.75 | 0.75 | 0.90 |
| Butylated hydroxytoluene | 0.05 | 0.05 | 0.10 |
| Push Layer | | | |
| Polyethylene oxide (POLYOX ® 303) | 135.0 | 135.0 | 135.0 |
| Povidone (KOLLIDON ® 30 LP) | 36.50 | 36.50 | 36.50 |
| Sodium chloride | 9.15 | 9.15 | 9.15 |
| Stearic acid | 0.45 | 0.45 | 0.45 |
| Butylated hydroxytoluene | 0.10 | 0.10 | 0.10 |
| Red Pigment blend | 1.80 | 1.80 | 1.80 |
| Functional Coating Layer | | | |
| Cellulose acetate | 40.70 | 40.70 | 40.70 |
| Polyethylene glycol 3350 | 0.40 | 0.40 | 0.40 |
| Acetone* | NA | NA | NA |
| Purified water* | NA | NA | NA |
| Total Weight | 584.10 | 584.10 | 584.10 |

*Removed during process

TABLE 2

Delayed Extended Release Methylphenidate HCl Tablets

| Composition | Tablet 4 mg/dose | Tablet 5 mg/dose | Tablet 6 mg/dose |
|---|---|---|---|
| Placebo layer | | | |
| Polyethylene oxide (POLYOX ® N80) | NA | 75.00 | NA |
| Polyethylene oxide (POLYOX ® 750) | 75.00 | NA | 75.00 |
| Povidone (KOLLIDON ® 30 LP) | 8.00 | 8.00 | 8.00 |
| Succinic acid | 3.00 | 3.00 | 3.00 |
| Stearic acid | 0.90 | 0.90 | 0.90 |
| Butylated hydroxytoluene | 0.10 | 0.10 | 0.10 |
| Active layer 1 | | | |
| Methylphenidate HCl | 10.80 | 10.80 | NA |
| Polyethylene oxide (POLYOX ® N80) | 37.24 | 37.24 | NA |
| Povidone (KOLLIDON ® 30 LP) | 4.00 | 4.00 | NA |
| Succinic acid | 1.10 | 1.10 | NA |
| Stearic acid | 0.05 | 0.05 | NA |
| Butylated hydroxytoluene | 0.05 | 0.05 | NA |
| Active layer 2 | | | |
| Methylphenidate HCl | 43.20 | 43.20 | 54.0 |
| Polyethylene oxide (POLYOX ® N80) | 216.0 | 216.0 | 270.0 |
| Povidone (KOLLIDON ® 30 LP) | 7.0 | 7.0 | 8.0 |
| Succinic acid | 3.0 | 3.0 | 3.0 |
| Stearic acid | 0.75 | 0.75 | 0.90 |
| Butylated hydroxytoluene | 0.05 | 0.05 | 0.10 |

TABLE 2-continued

Delayed Extended Release Methylphenidate HCl Tablets

| Composition | Tablet 4 mg/dose | Tablet 5 mg/dose | Tablet 6 mg/dose |
|---|---|---|---|
| Push Layer | | | |
| Polyethylene oxide (POLYOX ® 303) | 135.0 | 135.0 | 135.0 |
| Povidone (KOLLIDON ® 30 LP) | 36.50 | 36.50 | 36.50 |
| Sodium chloride | 9.15 | 9.15 | 9.15 |
| Stearic acid | 0.45 | 0.45 | 0.45 |
| Butylated hydroxytoluene | 0.10 | 0.10 | 0.10 |
| Red Pigment blend | 1.80 | 1.80 | 1.80 |
| Functional Coating Layer | | | |
| Cellulose acetate | 40.70 | 40.70 | 40.70 |
| Polyethylene glycol 3350 | 0.40 | 0.40 | 0.40 |
| Acetone* | NA | NA | NA |
| Purified water* | NA | NA | NA |
| Total Weight | 634.34 | 634.34 | 647.1 |

*Removed during process

Tablets 1, 2, 4, and 5 contained two active layers; and Tablets 3 and 6 contained one active layer. Tablets 1 and 2 had different grade of POLYOX® in the placebo layer compared to Tablets 4 and 5. The tablets were made according to the following manufacturing procedure.

Manufacturing Procedure:

Separate blends of placebo layer, active layer 1, active layer 2, and push layer were made as per Tablets 1-6, using the following manufacturing procedure.

1. Preparation of placebo blend: Povidone and BHT were added to dehydrated alcohol in a suitable stainless-steel container and mixed to obtain a clear solution; the resulting solution was sprayed onto polyethylene oxide taken in a high shear mixer; the resulting granules were dried at a temperature of about 40° C. in a forced air oven, and screened through screen #20; the resulting screened granules were taken in a V-blender containing succinic acid (pre-screened through screen #30) and mixed for 7 minutes at 25 RPM, followed by addition of stearic acid (prescreened through screen #30) and further mixing for about 3 minutes at 25 RPM.

2. Preparation of active layer 1 and active layer 2 blend: Povidone and BHT were added to dehydrated alcohol in a suitable stainless-steel container and mixed to obtain a clear solution; the resulting solution was sprayed onto a blend of methylphenidate HCl and polyethylene oxide taken in a high shear mixer; the resulting granules were dried at a temperature of about 40° C. in a forced air oven, and screened through screen #20; the resulting screened granules were taken in a V-blender containing succinic acid (prescreened through screen #30) and mixed for 7 minutes at 25 RPM, followed by addition of stearic acid (prescreened through screen #30) and further mixing for about 3 minutes at 25 RPM.

3. Preparation of push layer blend: Povidone and BHT were added to dehydrated alcohol in a suitable stainless-steel container and mixed to obtain a clear solution; the resulting solution was sprayed onto a blend of polyethylene oxide, sodium chloride, and red pigment blend taken in a high shear mixer; the resulting granules were dried at a temperature of about 40° C. in a forced air oven, and screened through screen #20; the resulting screened granules were taken in a V-blender containing stearic acid (prescreened through screen #30) and mixed for about 3 minutes at 25 RPM.

4. Required amount of each blend was filled into the die, in the order as per Tables 1 and 2, and then compressed into tetra-layer tablet compositions as outlined in Tables 1 and 2.

5. Cellulose acetate was added to a stainless-steel container charged with acetone and mixed to obtain a clear solution.

6. Polyethylene glycol 3350 was added to the solution from step #5, followed by the addition of water, and mixed for about 30 minutes.

7. The tablets from step #4 were taken in a coating pan and coated with the solution from step #6 until the target % weight gain is attained, and then cured at a product temperature of 40° C. for one hour.

8. A hole/orifice of about 0.3 mm is drilled into the coating, at the placebo layer end of the tablet.

Example 2

Preparation of Composition Providing Immediate Release of Clonidine and Delayed Extended Release of Methylphenidate HCl The present Example provides various formulations for delayed extended release methylphenidate HCL tablets that comprise clonidine HCl IR coating. The components of the clonidine HCl IR coating are provided in Table 3 below.

TABLE 3

Clonidine HCl IR coating

| Composition | Tablets 7-12 mg/dose |
|---|---|
| Clonidine HCl | 0.3 |
| Hypromellose (METHOCEL ™ E5 LV) | 2.5 |
| Talc | 0.5 |
| Ethanol* | NA |
| Purified water* | NA |

*Removed during process

The clonidine HCl IR coating is added to Tablets 1-6 of the Example 1 according to the procedure detailed below.

Manufacturing Procedure:

1. Hypromellose is added to ethanol taken in a stainless-steel container and mixed until it is uniformly dispersed. Purified water is slowly added and mixed until a clear solution is formed.

2. To the solution from step #1, clonidine HCl is added and mixed until dissolved.

3. Talc is added to the solution from step #2 and mixed until it is uniformly dispersed.

4. Methylphenidate HCl tablets (Tablets 1-6) are taken in a coating pan and coated with the dispersion from step #3.

Example 3

Preparation of Delayed Extended Release Mixed Amphetamine Tablet Compositions Comprising Two Active Layers The present Example provides three different delayed extended release mixed amphetamine tablet compositions. The components of the different tablets are outlined below in Table 4.

TABLE 4

Mixed Amphetamine Tablet Compositions

| Composition | Tablet 13 mg/dose | Tablet 14 mg/dose | Tablet 15 mg/dose |
|---|---|---|---|
| *Placebo Layer* | | | |
| Polyethylene oxide (POLYOX ® N80) | NA | 6.750 | NA |
| Polyethylene oxide (POLYOX ® 750) | 6.750 | NA | 6.750 |
| Povidone (KOLLIDON ® 30 LP) | 0.720 | 0.720 | 0.720 |
| Succinic acid | 0.270 | 0.270 | 0.270 |
| Stearic acid | 0.081 | 0.081 | 0.081 |
| Butylated hydroxytoluene | 0.009 | 0.009 | 0.009 |
| *Active Layer 1* | | | |
| Mixed amphetamine salts (base equivalence) | 1.000 | 1.000 | NA |
| Polyethylene oxide (POLYOX ® N80) | 3.35 | 3.35 | NA |
| Povidone (KOLLIDON ® 30 LP) | 0.360 | 0.360 | NA |
| Succinic acid | 0.099 | 0.099 | NA |
| Stearic acid | 0.004 | 0.004 | NA |
| Butylated hydroxytoluene | 0.0045 | 0.0045 | NA |
| *Active Layer 2* | | | |
| Total amphetamine base equivalence | 4.000 | 4.000 | 5.000 |
| Polyethylene oxide (POLYOX ® N80) | 19.44 | 19.44 | 24.3 |
| Povidone (KOLLIDON ® 30 LP) | 0.630 | 0.630 | 0.720 |
| Succinic acid | 0.270 | 0.270 | 0.270 |
| Stearic acid | 0.0675 | 0.0675 | 0.081 |
| Butylated hydroxytoluene | 0.0045 | 0.0045 | 0.009 |
| *Push Layer* | | | |
| Polyethylene oxide (POLYOX ® 303) | 12.150 | 12.150 | 12.150 |
| Povidone (KOLLIDON ® 30 LP) | 3.285 | 3.285 | 3.285 |
| Sodium Chloride | 0.823 | 0.823 | 0.823 |
| Stearic acid | 0.45 | 0.45 | 0.45 |
| Butylated hydroxytoluene | 0.0405 | 0.0405 | 0.0405 |
| Red Pigment blend | 0.162 | 0.162 | 0.162 |
| *Functional Coating Layer* | | | |
| Cellulose Acetate | 3.663 | 3.663 | 3.663 |
| Polyethylene Glycol 3350 | 0.036 | 0.036 | 0.036 |
| Acetone* | NA | NA | NA |
| Purified water* | NA | NA | NA |
| Total Weight | 57.67 | 57.67 | 58.819 |

*Removed during process

Tablets 13 and 15 contain POLYOX® 750 in the placebo layer; and Tablet 14 contain POLYOX® N80 in the placebo layer. Tablet 13 and Tablet 14 contain two active layers, and Tablet 15 contain one active layer. The tablets are made according to the following manufacturing procedure.

Manufacturing Procedure:

Tablets 13-15 comprise two active layers, Active layer 1 and Active layer 2, to provide delayed chrono drug release. Separate blends of placebo layer, active layer 1, active layer 2, and push layer are made as per Tablets 13-15.

1. Preparation of placebo blend: Povidone and BHT are added to dehydrated alcohol in a suitable stainless-steel container and mixed to obtain a clear solution; the resulting solution is sprayed onto polyethylene oxide taken in a high shear mixer; the resulting granules are dried at a temperature of about 40° C. in a forced air oven, and screened through screen #20; the resulting screened granules were taken in a V-blender containing succinic acid (prescreened through screen #30) and mixed for 7 minutes at 25 RPM, followed by addition of stearic acid (prescreened through screen #30) and further mixing for about 3 minutes at 25 RPM.

2. Preparation of active layer 1 and active layer 2 blend: Povidone and BHT are added to dehydrated alcohol in a suitable stainless-steel container and mixed to obtain a clear solution; the resulting solution is sprayed onto a blend of mixed amphetamine base, and polyethylene oxide taken in a high shear mixer; the resulting granules are dried at a temperature of about 40° C. in a forced air oven, and screened through screen #20; the resulting screened granules are taken in a V-blender containing succinic acid (prescreened through screen #30) and mixed for 7 minutes at 25 RPM, followed by addition of stearic acid (prescreened through screen #30) and further mixing for about 3 minutes at 25 RPM.

3. Preparation of push layer blend: Povidone and BHT are added to dehydrated alcohol in a suitable stainless-steel container and mixed to obtain a clear solution; the resulting solution is sprayed onto a blend of polyethylene oxide, sodium chloride, and red pigment blend taken in a high shear mixer; the resulting granules are dried at a temperature of about 40° C. in a forced air oven, and screened through screen #20; the resulting screened granules are taken in a V-blender containing stearic acid (prescreened through screen #30) and mixed for about 3 minutes at 25 RPM.

4. Required amount of each blend is filled into the die, in the order as per Table 4, and then compressed as tetra-layer tablet compositions.

5. Cellulose acetate is added to a stainless-steel container charged with acetone and mixed to obtain a clear solution.

6. Polyethylene glycol 3350 is added to the solution from step #5, followed by the addition of water, and mixed for about 30 minutes.

7. The tablets from step #4 are taken in a coating pan and coated with the solution from step #6 until the target % weight gain is attained and then cured at a product temperature of 40° C. for one hour.

8. A hole/orifice of about 0.3 mm is drilled into the coating, at the placebo layer end of the tablet.

Example 4

Preparation of Pulsatile Release Composition Comprising Two Active Layers Separated by a Placebo Layer The present Example provides a formulation for pulsatile release methylphenidate HCl tablet. The components of the tablet are outlined below in Table 5.

TABLE 5

Pulsatile Release Methylphenidate HCl Tablet

| Composition | Tablet 16 mg/dose |
|---|---|
| *Placebo Layer* | |
| Polyethylene oxide (POLYOX ® N80) | 75.00 |
| Povidone (KOLLIDON ® 30 LP) | 8.00 |
| Stearic acid | 0.90 |
| Butylated hydroxytoluene | 0.10 |
| *Active Layer 1* | |
| Methylphenidate HCl | 27.00 |
| Polyethylene oxide (POLYOX ® N80) | 81.00 |
| Povidone (KOLLIDON ® 30 LP) | 4.00 |
| Stearic acid | 0.05 |
| Butylated hydroxytoluene | 0.05 |

TABLE 5-continued

Pulsatile Release Methylphenidate HCl Tablet

| Composition | Tablet 16 mg/dose |
|---|---|
| Placebo Layer | |
| Polyethylene oxide (POLYOX ® N80) | 75.00 |
| Povidone (KOLLIDON ® 30 LP) | 8.00 |
| Stearic acid | 0.90 |
| Butylated hydroxytoluene | 0.10 |
| Active Layer 2 | |
| Methylphenidate HCl | 27.00 |
| Polyethylene oxide (POLYOX ® N80) | 81.0 |
| Povidone (KOLLIDON ® 30 LP) | 4.00 |
| Stearic acid | 0.05 |
| Butylated hydroxytoluene | 0.05 |
| Push Layer | |
| Polyethylene oxide (POLYOX ® 303) | 135.0 |
| Povidone (KOLLIDON ® 30 LP) | 36.50 |
| Sodium Chloride | 9.15 |
| Stearic acid | 0.45 |
| Butylated hydroxytoluene | 0.10 |
| Red Pigment blend | 1.80 |
| Functional Coating Layer | |
| Cellulose Acetate | 40.70 |
| Polyethylene Glycol 3350 | 0.40 |
| Acetone* | NA |
| Purified water* | NA |
| Total Weight | 616.30 |

*Removed during Process

Tablet 16 contains two placebo layers and two active layers disposed alternately. The composition further includes a push layer and a functional coating layer. Tablet 16 is made according to the procedure detailed below.

Manufacturing Procedure:

Separate blends of placebo layers, active layer 1, active layer 2, and push layer are made as per Tablet 16.

1. Preparation of placebo blend: Povidone and BHT are added to dehydrated alcohol in a suitable stainless-steel container and mixed to obtain a clear solution; the resulting solution is sprayed onto polyethylene oxide taken in a high shear mixer; the resulting granules are dried at a temperature of about 40° C. in a forced air oven, and screened through screen #20; the resulting screened granules are taken in a V-blender containing stearic acid (prescreened through screen #30) and mixed for about 3 minutes at 25 RPM.

2. Preparation of active layer 1 and active layer 2 blend: Povidone and BHT are added to dehydrated alcohol in a suitable stainless-steel container and mixed to obtain a clear solution; the resulting solution is sprayed onto a blend of methylphenidate HCL, and polyethylene oxide taken in a high shear mixer; the resulting granules are dried at a temperature of about 40° C. in a forced air oven, and screened through screen #20; the resulting screened granules are taken in a V-blender containing stearic acid (prescreened through screen #30) and mixed for about 3 minutes at 25 RPM.

3. Preparation of push layer blend: Povidone and BHT are added to dehydrated alcohol in a suitable stainless-steel container and mixed to obtain a clear solution; the resulting solution is sprayed onto a blend of polyethylene oxide, sodium chloride, and red pigment blend taken in a high shear mixer; the resulting granules are dried at a temperature of about 40° C. in a forced air oven, and screened through screen #20; the resulting screened granules are taken in a V-blender containing stearic acid (prescreened through screen #30) and mixed for about 3 minutes at 25 RPM.

4. Required amount of each blend is filled into the die, in the order as per Table 5, and then compressed into penta-layer tablet compositions.

5. Cellulose acetate is added to a stainless-steel container charged with acetone and mixed to obtain a clear solution.

6. Polyethylene glycol 3350 is added to the solution from step #5, followed by the addition of water, and mixed for about 30 minutes.

7. The tablets from step #4 are taken in a coating pan and coated with the solution from step #6 until the target % weight gain is attained and then cured at a product temperature of 40° C. for one hour.

8. A hole/orifice of about 0.3 mm is drilled into the coating, at the placebo layer end of the tablet.

Example 5

Clonidine HCl IR Coating

The present Example provides a formulation for pulsatile release methylphenidate HCl tablet that comprises clonidine HCl IR coating. The components of the clonidine HCl IR coating are provided in Table 6 below.

TABLE 6

Clonidine HCl IR Coating

| Composition | Tablet 17 mg/dose |
|---|---|
| Clonidine Hydrochloride | 0.3 |
| Hypromellose (METHOCEL E5LV) | 2.5 |
| Talc | 0.5 |
| Ethanol* | NA |
| Purified water* | NA |

*Removed during Process

The clonidine HCl IR coating is added to Tablet 16 of the Example 4 according to the procedure detailed below.

Manufacturing Procedure:

1. Hypromellose is added to ethanol taken in a stainless-steel container and mixed until it is uniformly dispersed. Purified water is slowly added and mixed until a clear solution is formed.

2. To the solution from step #1, clonidine hydrochloride is added and mixed until dissolved.

3. Talc is added to the solution from step #2 and mixed until it is uniformly dispersed.

4. The methylphenidate HCl tablets (Tablet 16) are taken in a coating pan and coated with the dispersion from step #3.

Example 6

Preparation of Delayed Extended Release Methylphenidate HCl Tablet Compositions Containing One Active Layer The present Example provides two different delayed extended release methylphenidate HCl tablet compositions. The components of the different tablets are outlined below in Table 7.

TABLE 7

Extended Release Methylphenidate HCl Tablet Compositions

| Composition | Tablet 18 mg/dose | Tablet 19 mg/dose |
|---|---|---|
| Placebo Layer | | |
| Polyethylene oxide (POLYOX® WSR 1105) | 100.31 | 100.31 |
| Povidone (KOLLIDON® 30 LP) | 5.22 | 5.22 |
| Stearic acid | 1.00 | 1.00 |
| Butylated hydroxytoluene | 0.13 | 0.13 |
| Red pigment blend | 0.07 | 0.07 |
| Cab-O-Sil® (fumed silica) | 0.27 | 0.27 |
| Dehydrated alcohol* | q.s. | q.s. |
| Active Layer | | |
| Methylphenidate HCl | 54.00 | 54.00 |
| Polyethylene oxide (POLYOX® N80) | 81.00 | 81.00 |
| Sodium chloride | 10.00 | 10.00 |
| Povidone (KOLLIDON® 30 LP) | 7.60 | 7.60 |
| Stearic acid | 0.90 | 0.90 |
| Butylated hydroxytoluene | 0.10 | 0.10 |
| Dehydrated alcohol* | q.s. | q.s. |
| Push Layer | | |
| Polyethylene oxide (POLYOX® WSR 303) | 88.00 | 88.00 |
| Sodium chloride | 22.00 | 22.00 |
| Povidone (KOLLIDON® 30 LP) | 11.50 | 11.50 |
| Stearic acid | 0.50 | 0.50 |
| Butylated hydroxytoluene (BHT) | 0.20 | 0.20 |
| Red pigment blend | 1.50 | 1.50 |
| Cab-O-Sil® | 0.30 | 0.30 |
| Dehydrated alcohol* | q.s. | q.s. |
| Total Core Weight | 384.6 | 384.6 |
| Functional Coating Layer | | |
| OPADRY® CA clear (95:5) | 48.13 | 57.75 |
| Total Tablet Weight | 432.73 | 442.35 |

*Removed during process

Tablet 18 and Tablet 19 include different amounts of OPADRY® CA with CA:PEG ratio of about 95:5. The tablets were made according to the following manufacturing procedure.

Manufacturing Procedure

Separate blends of placebo layer, active layer, and push layer were made as per Tablets 18 and 19.

1. Preparation of placebo blend: Povidone and BHT were added to dehydrated alcohol in a suitable stainless-steel container and mixed to obtain a clear solution; the resulting solution was sprayed onto a blend of polyethylene oxide and red pigment blend taken in a high shear mixer; the resulting granules were dried at a temperature of about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and mixing for 3 minutes.

2. Preparation of active layer blend: Povidone and BHT were added to dehydrated alcohol in a suitable stainless-steel container and mixed to obtain a clear solution; the resulting solution was sprayed onto a blend of methylphenidate HCl, polyethylene oxide and sodium chloride taken in a high shear mixer; the resulting granules were dried at a temperature of about 40° C. in a forced air oven, and screened through screen #20; the resulting screened granules are taken in a V-blender containing stearic acid (prescreened through screen #30) and mixed for about 3 minutes at 25 RPM.

3. Preparation of push layer blend: Povidone and BHT were added to dehydrated alcohol in a suitable stainless-steel container and mixed to obtain a clear solution; the resulting solution was sprayed onto a blend of polyethylene oxide, sodium chloride, and red pigment blend taken in a high shear mixer; the resulting granules were dried at a temperature of about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and further mixing for 3 minutes.

4. Required amount of each blend (as per Tablets 18 and 19) was filled into the die and then compressed as tri-layer tablet composition.

5. OPADRY® CA was added to a stainless-steel container charged with acetone and water (about 92:8) and mixed for not less than 60 minutes to obtain a clear solution.

6. The tablets from step #4 were taken in a coating pan and coated with the solution from step #5 until the target % weight gain was obtained and cured at a product temperature of 40° C. for one hour.

7. A hole/orifice of about 0.3 mm was drilled into the coating, at the placebo layer end of the tablet.

Example 7

Dissolution Profiles of Tablets Containing Different Amounts of POLYOX® WSR 1105 in the Placebo Layer The present Example provides two different delayed extended release methylphenidate HCl tablets with various amounts of POLYOX® WSR 1105 in the placebo layer. The components of the two tablets are outlined below in Table 8.

TABLE 8

Delayed Extended Release Methylphenidate HCl Tablets

| Composition | Tablet 20 mg/dose | Tablet 21 mg/dose |
|---|---|---|
| Placebo Layer | | |
| Polyethylene oxide (POLYOX® WSR 1105) | 150.0 | 75.0 |
| Povidone (KOLLIDON® 30 LP) | 8.0 | 4.0 |
| Stearic acid | 1.6 | 0.8 |
| Butylated hydroxytoluene | 0.20 | 0.10 |
| Dehydrated alcohol* | q.s. | q.s. |
| Active Layer | | |
| Methylphenidate HCl | 54.0 | 54.0 |
| Polyethylene oxide (POLYOX® N80) | 135.0 | 135.0 |
| Povidone (KOLLIDON® 30 LP) | 4.0 | 4.0 |
| Stearic acid | 0.90 | 0.90 |
| Butylated hydroxytoluene | 0.10 | 0.10 |
| Dehydrated alcohol* | q.s. | q.s. |
| Push Layer | | |
| Polyethylene oxide (POLYOX® WSR 303) | 88.00 | 88.00 |
| Sodium chloride | 22.00 | 22.00 |
| Povidone (KOLLIDON® 30 LP) | 12.0 | 12.0 |
| Stearic acid | 0.50 | 0.50 |
| Butylated hydroxytoluene (BHT) | 0.20 | 0.20 |
| Red pigment | 1.50 | 1.50 |
| Dehydrated alcohol* | q.s. | q.s. |
| Total Core Weight | 478.0 | 398.1 |
| Functional Coating Layer | | |
| OPADRY® CA clear (95:5) | 71.7 | 59.7 |
| Total Weight | 549.7 | 457.8 |

*Removed during process

Tablet 20 contained 150 mg of POLYOX® WSR 1105 in the placebo layer; and Tablet 21 contained 75.0 mg of POLYOX® WSR 1105 in the placebo layer. Tablet 20 contained about 34 wt % of placebo layer, based on the total weight of the uncoated tablet core. Tablet 21 contained about 20 wt % of placebo layer, based on the total weight of the uncoated tablet core. Tablets 20 and 21 contained 15 wt % of coating, based on the total weight of the uncoated tablet core. Trilayer methylphenidate HCl tablets were made Trilayer methylphenidate HCl tablets were made following the same procedure as outlined in Example 6.

Tablets 20 and 21 were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. The effect of POLYOX® amount present in placebo layer on lag time and dissolution profile of the tablet is shown in FIG. 6. FIG. 6 demonstrates that tablets with higher amount of POLYOX® WSR 1105 in the placebo layer exhibit higher dissolution rate and higher drug recovery compared to tablets with lesser amounts of POLYOX® WSR 1105 in the placebo layer. FIG. 6 further demonstrates that the POLYOX® WSR 1105 amount in the placebo layer, and weight % of placebo layer, based on the total weight of the uncoated tablet core, does not affect lag time.

Example 8

Dissolution Profiles of Tablets with Different Drug: Polymer Weight Ratios in the Active Layer The present Example provides two delayed extended release methylphenidate HCl tablets comprising active layers with varying drug to polymer weight ratios. The components of the two tablets are outlined below in Table 9.

TABLE 9

Delayed Extended Release Methylphenidate HCl Tablets

| Composition | Tablet 22 mg/dose | Tablet 23 mg/dose |
|---|---|---|
| Placebo Layer | | |
| Polyethylene oxide (POLYOX® WSR 1105) | 150.0 | 150.0 |
| Povidone (KOLLIDON® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX® N80) | 207.0 (20:80) | 135.0 (28:72) |
| Povidone (KOLLIDON® 30 LP) | 4.0 | 4.0 |
| Stearic acid | 0.9 | 0.9 |
| Butylated hydroxytoluene | 0.10 | 0.10 |
| Dehydrated alcohol* | q.s. | q.s. |
| Push Layer | | |
| Polyethylene oxide (POLYOX® WSR 303) | 98.00 | 98.00 |
| Sodium chloride | 12.00 | 12.00 |
| Povidone (KOLLIDON® 30 LP) | 12.0 | 12.0 |
| Stearic acid | 0.50 | 0.50 |

TABLE 9-continued

Delayed Extended Release Methylphenidate HCl Tablets

| Composition | Tablet 22 mg/dose | Tablet 23 mg/dose |
|---|---|---|
| Butylated hydroxy toluene (BHT) | 0.20 | 0.20 |
| Red pigment blend | 1.50 | 1.50 |
| Dehydrated alcohol* | q.s. | q.s. |
| Total core Weight | 550.0 | 478.0 |
| Functional Coating Layer | | |
| OPADRY® CA clear (95:5) | 82.5 | 71.7 |
| Total Weight | 632.5 | 549.7 |

*Removed during process

Tablet 22 contained drug: POLYOX® N 80 weight ratio of about 20:80. Tablet 23 contained drug: POLYOX® N 80 weight ratio of about 30:70. Trilayer methylphenidate Trilayer methylphenidate HCl tablets were made following the procedure as outlined in Example 6. Tablets 22 and 23 were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 7 shows the effect of drug: polymer weight ratio in the active layer on lag time and drug recovery of the tablet. FIG. 7 demonstrates that increasing drug: polymer weight ratio in the active layer reduces lag time. Tablet 23 with a drug to polymer weight ratio of about 30:70 provides a lag time of about 9 hours, Tablet 22 with a drug to polymer weight ratio of about 20:80 provides a lag time of about 10 hours. FIG. 7 further demonstrates that tablets with the drug to polymer weight ratio of about 30:70 provide higher drug recovery compared to tablets with drug to polymer weight ratio of about 20:80.

Example 9

Dissolution Profiles of Tablets with and without Sodium Chloride in the Active Layer The present Example provides two delayed extended release methylphenidate HCl tablets. The components of the two tablets are outlined below in Table 10.

TABLE 10

Delayed Extended Release Methylphenidate HCl Tablets

| Composition | Tablet 24 mg/dose | Tablet 25 mg/dose |
|---|---|---|
| Placebo Layer | | |
| Polyethylene oxide (POLYOX® WSR 1105) | 150.0 | 150.0 |
| Povidone (KOLLIDON® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX® N80) | 125.0 | 135.0 |
| Sodium chloride | 10.0 | — |
| Povidone (KOLLIDON® 30 LP) | 4.0 | 4.0 |
| Stearic acid | 0.9 | 0.9 |
| Butylated hydroxytoluene | 0.10 | 0.10 |
| Dehydrated alcohol* | q.s. | q.s. |

TABLE 10-continued

Delayed Extended Release Methylphenidate HCl Tablets

| Composition | Tablet 24 mg/dose | Tablet 25 mg/dose |
|---|---|---|
| Push Layer | | |
| Polyethylene oxide (POLYOX ® WSR 303) | 98.00 | 98.00 |
| Sodium chloride | 22.00 | 22.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Total Core Weight | 488.0 | 488.0 |
| Functional Coating Layer | | |
| OPADRY ® CA clear (95:5) | 71.7 | 71.7 |
| Total Weight | 559.7 | 559.7 |

*Removed during process

Tablet 24 contained sodium chloride in the active layer; and Tablet 25 did not contain any amount of sodium chloride in the active layer. Trilayer methylphenidate HCl tablets were made following the procedure as outlined in Example 6. Tablets 24 and 25 were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 8 shows a comparison of drug recovery from tablets with and without sodium chloride in the active layer. FIG. 8 demonstrates that Tablet 24 containing NaCl in the active layer exhibits higher drug recovery compared to Tablet 25 containing no amount of sodium chloride in the active layer.

Example 10

Dissolution Profiles of Tablets Containing Different Sodium Chloride Amounts in the Push Layer The present Example provides four delayed extended release methylphenidate HCl tablets comprising different amounts of sodium chloride in the push layer. The components of the four tablets are outlined below in Table 11.

TABLE 11

Delayed Extended Release Methylphenidate HCl Tablets

| Composition | Tablet 23 mg/dose | Tablet 26 mg/dose | Tablet 27 mg/dose | Tablet 28 mg/dose |
|---|---|---|---|---|
| Placebo Layer | | | | |
| Polyethylene oxide (POLYOX ® WSR 1105) | 150.0 | 150.0 | 150.0 | 150.0 |
| Povidone (KOLLIDON ® 30 LP) | 8.0 | 8.0 | 8.0 | 8.0 |
| Stearic acid | 1.6 | 1.6 | 1.6 | 1.6 |
| Butylated hydroxytoluene | 0.20 | 0.20 | 0.2 | 0.2 |
| Dehydrated alcohol* | q.s. | q.s. | q.s. | q.s. |
| Active Layer | | | | |
| Methylphenidate HCl | 54.0 | 54.0 | 54.0 | 54.0 |
| Polyethylene oxide (POLYOX ® N80) | 135.0 | 135.0 | 135.0 | 135.0 |
| Povidone (KOLLIDON ® 30 LP) | 4.0 | 4.0 | 4.0 | 4.0 |
| Stearic acid | 0.9 | 0.9 | 0.9 | 0.9 |
| Butylated hydroxytoluene | 0.10 | 0.10 | 0.10 | 0.10 |
| Dehydrated alcohol* | q.s. | q.s. | q.s. | q.s. |
| Push Layer | | | | |
| Polyethylene oxide (POLYOX ® WSR 303) | 98.00 | 80.00 | 88.0 | 110.0 |
| Sodium chloride | 12.00 | 30.00 | 22.0 | NA |
| Povidone (KOLLIDON ® 30 LP) | 12.0 | 12.0 | 12.0 | 12.0 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.50 | 1.50 | 1.50 | 1.50 |
| Dehydrated alcohol* | q.s. | q.s. | q.s. | q.s. |
| Total Core Weight | 478.0 | 478.0 | 478.0 | 478.0 |
| Functional Coating Layer | | | | |
| OPADRY ® CA clear (95:5) | 71.7 | 71.7 | 71.7 | 71.7 |
| Total Weight | 549.7 | 549.7 | 549.7 | 549.7 |

*Removed during process

Tablet 28 did not contain any amount of sodium chloride in the push layer; Tablet 23 contained about 10 wt % of sodium chloride, based on the total weight of the push layer; Tablet 27 contained about 18 wt % of sodium chloride, based on the total weight of the push layer; and tablet 26 contained about 25 wt % of sodium chloride, based on the in push layer.

Trilayer methylphenidate HCl tablets were made following the procedure as outlined in Example 6. Tablets 23, 26, 27, and 28, were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 9 shows the effect of presence and amount of sodium chloride in the push layer on lag time, release rate, and drug recovery from the tablet. FIG. 9 demonstrates that the presence of sodium chloride in the push layer reduces lag time and improves release rate and drug recovery at 24 hours. FIG. 9 further demonstrates that increasing the amount of sodium chloride in the push layer reduces lag time.

Example 11

Dissolution Profiles of Tablets Containing Different Membrane Compositions

The present Example provides two delayed extended release methylphenidate HCl tablets. The components of the two tablets are outlined below in Table 12.

TABLE 12

Delayed Extended Release Methylphenidate HCl Tablets

| Composition | Tablet 29 mg/dose | Tablet 30 mg/dose |
|---|---|---|
| *Placebo Layer* | | |
| Polyethylene oxide (POLYOX ® N205) | 150.0 | 150.0 |
| Povidone (KOLLIDON ® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| *Active Layer* | | |
| Methylphenidate HCl | 54.0 | 54.0 |
| Polyethylene oxide (POLYOX ® N80) | 135.0 | 135.0 |
| Povidone (KOLLIDON ® 30 LP) | 4.0 | 4.0 |
| Stearic acid | 0.9 | 0.9 |
| Butylated hydroxytoluene | 0.10 | 0.10 |
| Dehydrated alcohol* | q.s. | q.s. |
| *Push Layer* | | |
| Polyethylene oxide (POLYOX ® WSR 303) | 80.00 | 80.00 |
| Sodium chloride | 30.00 | 30.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Core Tablet Weight | 478.0 | 478.0 |
| *Functional Coated Layer* | | |
| OPADRY ® CA clear | 71.7 | 71.7 |
| CA:PEG Ratio | 95:5 | 98:2 |
| Total Weight | 549.7 | 549.7 |

*Removed during process

Tablet 29 contained OPADRY® CA with CA:PEG ratio of about 95:5 in the functional coating layer; and Tablet 30 contained OPADRY® CA with CA:PEG ratio of about 98:2 in the functional coating layer.

Trilayer methylphenidate HCl tablets were prepared by the procedure as outlined in Example 6. Tablets 29 and 30 and were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 10 shows effect of CA to PEG weight ratio in the functional coat/membrane on lag time and drug recovery of the tablets containing about 15% coating weight gain. FIG. 10 demonstrates that increasing the amount of cellulose acetate in the functional coating layer, at a same coating weight gain, increases lag time and reduces drug recovery from the functional coated tablets.

Example 12

Effect of Coating Level and Presence of Sodium Chloride in Active Layer on Lag Time and Drug Recovery The present Example provides four delayed extended release methylphenidate HCl tablets. The components of the Tablets 31, 32, and 33 are outlined below in Table 13.

TABLE 13

Delayed Extended Release Methylphenidate HCl Tablets

| Composition | Tablet 31 mg/dose | Tablet 32 mg/dose | Tablet 33 mg/dose |
|---|---|---|---|
| *Placebo Layer* | | | |
| Polyethylene oxide (POLYOX ® N205) | 150.0 | 150.0 | 75.0 |
| Povidone (KOLLIDON ® 30 LP) | 8.0 | 8.0 | 4.0 |
| Stearic acid | 1.6 | 1.6 | 0.8 |
| Butylated hydroxytoluene | 0.20 | 0.20 | 0.1 |
| Dehydrated alcohol* | q.s. | q.s. | q.s. |
| *Active Layer* | | | |
| Methylphenidate HCl | 54.0 | 54.0 | 54.0 |
| Polyethylene oxide (POLYOX ® N80) | 125.0 | 135.0 | 135.0 |
| Povidone (KOLLIDON ® 30 LP) | 4.0 | 4.0 | 4.0 |
| Stearic acid | 0.9 | 0.9 | 0.9 |
| Sodium chloride | 10.0 | NA | NA |
| Butylated hydroxytoluene | 0.10 | 0.10 | 0.1 |
| Dehydrated alcohol* | q.s. | q.s. | q.s. |
| *Push Layer* | | | |
| Polyethylene oxide (POLYOX ® WSR 303) | 88.0 | 88.0 | 88.0 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.5 |
| Butylated hydroxytoluene (BHT) | 0.20 | 0.20 | 0.2 |
| Red pigment blend | 1.50 | 1.50 | 1.5 |
| Dehydrated alcohol* | q.s. | q.s. | q.s. |
| Core Tablet Weight | 478.0 | 478.0 | 398.1 |
| *Functional Coating Layer* | | | |
| OPADRY ® CA clear (95:5) | 71.7 | 71.7 | 59.7 |
| Total Weight | 549.0 | 549.0 | 457.8 |

*Removed during process

Tablet 31 contained 15% coating weight gain of the functional coat layer and Tablet 31A contained 17.5% coating weight gain of the functional coat layer, based on the total weight of the uncoated tablets. Tablets 31 and 31A contained sodium chloride in the active layer; and Tablets 32 and 33 did not contain any amount of sodium chloride in the active layer. Trilayer methylphenidate HCl tablets were made by following the procedure as outlined in Example 6. Tablets 31, 31A, 32, and 33 were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 11 shows effect of coating weight gain/coating level of the functional coat/semipermeable membrane on drug recovery and lag time. FIG. 11 demonstrates that Tablet 31A containing about 17.5 wt % coating weight gain of the functional coat exhibits reduced drug recovery and increased lag time compared to Tablet 31 with about 15 wt % of the coating weight gain. FIG. 11 further compares drug recovery between coated tablets with and without sodium chloride in active layer. FIG. 11 demonstrates that Tablet 31 containing sodium chloride in the active layer exhibits improved drug recovery compared to Tablets 32 and 33 containing no amount of sodium chloride in the active layer, all tablets at a same coating weight gain.

Example 13

Effect of pH on Lag Time

The present Example provides a delayed extended release methylphenidate HCl tablet comprising a placebo layer, an active layer, a push layer, and a functional coating layer. The components of the tablet are outlined below in Table 14.

TABLE 14

Delayed Extended Release Methylphenidate HCl Tablet

| Composition | Tablet 34 mg/dose |
|---|---|
| Placebo layer | |
| Polyethylene oxide (POLYOX ® N205) | 150.0 |
| Povidone (KOLLIDON ® 30 LP) | 8.0 |
| Stearic acid | 1.6 |
| Butylated hydroxytoluene | 0.20 |
| Dehydrated alcohol* | q.s. |
| Active layer | |
| Methylphenidate HCl | 54.0 |
| Polyethylene oxide (POLYOX ® N80) | 125.0 |
| Povidone (KOLLIDON ® 30 LP) | 4.0 |
| Stearic acid | 0.9 |
| Butylated hydroxytoluene | 0.10 |
| Sodium chloride | 10.0 |
| Dehydrated alcohol* | q.s. |
| Push layer | |
| Polyethylene oxide (POLYOX ® WSR 303) | 88.0 |
| Sodium chloride | 22.00 |
| Povidone (KOLLIDON ® 30 LP) | 12.0 |
| Stearic acid | 0.50 |
| Butylated hydroxy toluene (BHT) | 0.10 |
| Red pigment blend | 1.60 |
| Dehydrated alcohol* | q.s. |
| Core Tablet Weight | 478.0 |
| Functional Coating Layer | |
| OPADRY ® CA clear (95:5) | 71.7 |
| Total Weight | 549.7 |

*Removed during process

Trilayer methylphenidate HCl tablets were made by following the procedure outlined in Example 6. Tablet 34 was tested for dissolution in 900 ml of 0.01N HCl (pH 2.0), pH 4.5 acetate buffer, and pH 6.8 phosphate buffer, for up to 24 hours, using USP Apparatus II (Sinkers), at 50 rpm and 37° C. Percentage dissolution of the tablet was measured at 2, 4, 6, 8, 10, 12, 14, 16, 18, 20, 22, and 24 hours. FIG. 12 shows effect of pH on lag time in a tablet with a drug to polymer weight ratio of about 30:70. FIG. 12 demonstrates that the tablets exhibit minimal variability in lag time with variations in pH of the dissolution medium.

Example 14

Effect of Push Layer Amount on Lag Time

The present Example provides two delayed extended release methylphenidate HCl tablets with different amounts of components in the push layer. The components of the two tablets are outlined below in Table 15.

TABLE 15

Delayed Extended Release Methylphenidate HCl Tablets

| Composition | Tablet 35 mg/dose | Tablet 36 mg/dose |
|---|---|---|
| Placebo Layer | | |
| Polyethylene oxide (POLYOX ® 1105) | 150.0 | 150.0 |
| Povidone (KOLLIDON ® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX ® N80) | 81.0 | 81.0 |
| Povidone (KOLLIDON ® 30 LP) | 4.0 | 4.0 |
| Stearic acid | 0.9 | 0.9 |
| Butylated hydroxytoluene | 0.10 | 0.10 |
| Sodium chloride | 10.0 | 10.0 |
| Dehydrated alcohol* | q.s. | q.s. |
| Push Layer | | |
| Polyethylene oxide (POLYOX ® WSR 303) | 71.00 | 88.00 |
| Sodium chloride | 17.7 | 22.0 |
| Povidone (KOLLIDON ® 30 LP) | 12.0 | 8.4 |
| Stearic acid | 0.40 | 0.50 |
| Butylated hydroxytoluene (BHT) | 0.10 | 0.10 |
| Red pigment blend | 1.3 | 1.6 |
| Dehydrated alcohol* | q.s. | q.s. |
| Core Tablet Weight | 412.3 | 430.4 |
| Functional Coating Layer | | |
| OPADRY ® CA clear (95:5) | 61.5 | 65.1 |
| Total Weight | 473.8 | 495.5 |

*Removed during process

Tablet 35 contained 108.5 mg of push layer (about 26 wt % of push layer, based on the total weight of the uncoated tablet core) and Tablet 36 contained 120.6 mg of push layer (about 28 wt % of push layer, based on the total weight of the uncoated tablet core). Tablets 35 and 36 contained about 15 wt % of the functional coating layer, based on the total weight of the uncoated tablet core. Trilayer methylphenidate HCl tablets were made according to the procedure as per Example 6. Tablets 35 and 36 were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 13 shows the effect of push layer amount on lag time in tablets with drug to polymer weight ratios of about 40:60. The figure demonstrates that an increase in push layer amount, from about 26 wt % to about 28 wt %, based on the total weight of the uncoated tablet core, improves drug recovery without affecting the lag time.

Example 15

Effect of pH and Viscosity of Dissolution Medium on Lag Time

The present Example provides a delayed extended release methylphenidate HCl tablet comprising a placebo layer, an active layer, a push layer and a functional coating layer. The components of the tablet are outlined below in Table 16.

TABLE 16

Delayed Extended Release Methylphenidate HCl Tablet

| Composition | Tablet 37 mg/dose |
|---|---|
| Placebo Layer | |
| Polyethylene oxide (POLYOX ® 1105) | 100.0 |
| Povidone (KOLLIDON ® 30 LP) | 5.2 |
| Stearic acid | 1.0 |
| Butylated hydroxytoluene | 0.20 |
| Cab-O-Sil ® | 0.3 |
| Dehydrated alcohol* | q.s. |
| Active layer | |
| Methylphenidate HCl | 54.0 |
| Polyethylene oxide (POLYOX ® N80) | 81.0 |
| Povidone (KOLLIDON ® 30 LP) | 8.0 |
| Stearic acid | 0.9 |
| Cab-O-Sil ® | 0.4 |
| Butylated hydroxytoluene | 0.10 |
| Sodium chloride | 10.0 |
| Dehydrated alcohol* | q.s. |
| Push layer | |
| Polyethylene oxide (POLYOX ® WSR 303) | 88.00 |
| Sodium chloride | 22.0 |
| Povidone (KOLLIDON ® 30 LP) | 12.0 |
| Stearic acid | 0.50 |
| Butylated hydroxytoluene (BHT) | 0.20 |
| Red pigment blend | 1.5 |
| Cab-O-Sil ® | 0.3 |
| Dehydrated alcohol* | q.s. |
| Core Tablet Weight | 385.6 |
| Functional Coated Layer | |
| OPADRY ® CA (95:5) | 48.16 |
| Total Weight | 433.76 |

*Removed during process

Trilayer methylphenidate HCl tablets were made according to the procedure as per Example 6. Tablet 37 was tested for dissolution in 900 ml of 0.01N HCl, 900 ml of pH 4.5 acetate buffer, and 900 ml of pH 6.8 phosphate buffer, for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 14 compares dissolution rate of Tablet 37 at pH 2, pH 4.5, and pH 6.8. The figure demonstrates that Tablet 37 exhibits minimal variability in lag time with variations in pH of the dissolution medium.

FIG. 15 provides dissolution rate of Tablet 37 in dissolution mediums with different viscosities. The figure demonstrates that Tablet 37 exhibits minimal variability in lag time with variations in viscosity of the dissolution medium.

Example 16

Effect of Discrimination Methods on Lag Time

Dissolution profiles of Tablet 37 were measured for up to 24 hours using USP Apparatus II (Sinkers) in 900 ml of 0.01N HCl at 50 rpm and 37° C. and using USP Apparatus III (Biodis) at 25 dpm and 37° C. (conditions mimicking effect of stomach shear). Percentage dissolution of the tablets was measured at 2, 4, 6, 8, 10, 12, 14, 16, 18, 20, 22, and 24 hours using the two methods. FIG. 16 compares dissolution rate of Tablet 37, containing a drug: polymer weight ratio of about 40:60, using the above two methods. The figure demonstrates that there is no substantial change in lag time with changing hydrodynamics of the dissolution medium.

Example 17

Effect of Sodium Chloride Amount in the Placebo Layer on Lag Time and Release Rate The present Example provides three delayed extended release methylphenidate HCl tablets comprising different amounts of sodium chloride in the placebo layer. The components of the three tablets are outlined below in Table 17.

TABLE 17

Delayed Extended Release Methylphenidate HCl Tablets

| Composition | Tablet 38 mg/dose | Tablet 39 mg/dose | Tablet 40 mg/dose |
|---|---|---|---|
| Placebo Layer | | | |
| Polyethylene oxide (POLYOX ® 1105) | 100.0 | 100.0 | 100.0 |
| Povidone (KOLLIDON ® 30 LP) | 5.2 | 5.2 | 5.2 |
| Stearic acid | 1.0 | 1.0 | 1.0 |
| Sodium chloride | — | 5.33 | 10.67 |
| Butylated hydroxytoluene | 0.20 | 0.20 | 0.2 |
| Cab-O-Sil ® | 0.3 | 0.2 | 0.2 |
| Red pigment blend | 0.1 | 0.1 | 0.1 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX ® N80) | 81.0 | 81.0 | 81.0 |
| Povidone (KOLLIDON ® 30 LP) | 8.0 | 8.0 | 8.0 |
| Stearic acid | 0.9 | 0.9 | 0.9 |
| Cab-O-Sil ® | 0.4 | 0.4 | 0.4 |
| Butylated hydroxytoluene | 0.10 | 0.10 | 0.10 |
| Sodium chloride | 10.0 | 10.0 | 10.0 |
| Dehydrated alcohol* | q.s. | q.s. | q.s |
| Push Layer | | | |
| Polyethylene oxide (POLYOX ® WSR 303) | 88.00 | 88.00 | 88.00 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.50 |
| Butylated hydroxytoluene (BHT) | 0.20 | 0.20 | 0.20 |
| Red pigment blend | 1.5 | 1.5 | 1.5 |
| Cab-O-Sil ® | 0.3 | 0.3 | 0.3 |
| Dehydrated alcohol* | q.s.. | q.s. | q.s. |
| Core Tablet Weight | 385.7 | 390.83 | 396.27 |
| Functional Coating Layer | | | |
| OPADRY ® CA (95:5) | 48.16 | 48.83 | 49.49 |
| Total Weight | 433.86 | 439.66 | 445.76 |

*Removed during process

Tablet 38 did not contain any amount of sodium chloride in the placebo layer; Tablet 39 contained 5.33 mg of sodium chloride in the placebo layer; and Tablet 40 contained 10.67 mg of sodium chloride in the placebo layer. Trilayer methylphenidate HCl tablets were made according to the procedure as per Example 6. Tablets 38, 39, and 40 were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 17 shows effect of sodium chloride in placebo layer on lag time and release rate. The figure demonstrates that the presence and amount of sodium chloride in the placebo layer has negligible effect on lag time and release rate.

Example 18

Effect of POLYOX® Grade in Placebo Layer on Lag Time

The present Example provides three delayed extended release methylphenidate HCl tablets comprising different grades of POLYOX® in the placebo layer. The components of the three tablets are outlined below in Table 18.

TABLE 18

Delayed Extended Release Methylphenidate HCl Tablets

| Composition | Tablet 38 mg/dose | Tablet 41 mg/dose | Tablet 42 mg/dose |
|---|---|---|---|
| Placebo Layer | | | |
| Polyethylene oxide (POLYOX ® 1105) | 100.0 | — | — |
| Polyethylene oxide (POLYOX ® N750) | — | 100.0 | — |
| Polyethylene oxide (POLYOX ® N80) | — | — | 100.0 |
| Povidone (KOLLIDON ® 30 LP) | 5.2 | 5.2 | 5.2 |
| Stearic acid | 1.0 | 1.0 | 1.0 |
| Sodium chloride | — | — | — |
| Butylated hydroxytoluene | 0.20 | 0.20 | 0.2 |
| Cab-O-Sil ® | 0.3 | 0.2 | 0.2 |
| Red pigment blend | 0.1 | 0.1 | 0.1 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX ® N80) | 81.0 | 81.0 | 81.0 |
| Povidone (KOLLIDON ® 30 LP) | 8.0 | 8.0 | 8.0 |
| Stearic acid | 0.9 | 0.9 | 0.9 |
| Cab-O-Sil ® | 0.4 | 0.4 | 0.4 |
| Butylated hydroxytoluene | 0.10 | 0.10 | 0.10 |
| Sodium chloride | 10.0 | 10.0 | 10.0 |
| Dehydrated alcohol* | q.s. | q.s. | q.s |
| Push Layer | | | |
| Polyethylene oxide (POLYOX ® WSR 303) | 88.00 | 88.00 | 88.00 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.50 |
| Butylated hydroxytoluene (BHT) | 0.20 | 0.20 | 0.20 |
| Red pigment blend | 1.5 | 1.5 | 1.5 |
| Cab-O-Sil ® | 0.3 | 0.3 | 0.3 |
| Dehydrated alcohol* | q.s.. | q.s. | q.s. |
| Core Tablet Weight | 385.6 | 385.6 | 385.6 |
| Functional Coating Layer | | | |
| OPADRY ® CA (95:5) | 48.16 | 48.16 | 48.16 |
| Total Weight | 433.76 | 433.76 | 433.76 |

*Removed during process

Tablet 38 contained POLYOX® 1105 in the placebo layer; Tablet 41 contained POLYOX® N750 in the placebo layer; and Tablet 42 contained POLYOX® N80 in the placebo layer. Trilayer methylphenidate HCl tablets were made according to the procedure as per Example 6. Tablets 38, 41, and 42 were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 18 shows the effect of POLYOX® grade/average molecular weight in placebo layer on lag time. The figure compares lag time in compositions containing POLYOX® 80 (200K), POLYOX® 750 (300K), and POLYOX® 1105 (900K) in the placebo layer. The figure demonstrates that the average molecular weight of the POLYOX® in the placebo layer should be at least about 300K for providing a lag time of at least about 6 hours.

Example 19

Effect of POLYOX® Grade in Push Layer on Lag Time

The present Example provides three delayed extended release methylphenidate HCl tablets comprising different grades of POLYOX® in the push layer. The components of the three tablets are outlined below in Table 19.

TABLE 19

Delayed Extended Release Methylphenidate HCl Tablets

| Composition | Tablet 38 mg/dose | Tablet 43 mg/dose | Tablet 44 mg/dose |
|---|---|---|---|
| Placebo Layer | | | |
| Polyethylene oxide (POLYOX ® 1105) | 100.0 | — | — |
| Polyethylene oxide (POLYOX ® N750) | — | 100.0 | — |
| Polyethylene oxide (POLYOX ® N80) | — | — | 100.0 |
| Povidone (KOLLIDON ® 30 LP) | 5.2 | 5.2 | 5.2 |
| Stearic acid | 1.0 | 1.0 | 1.0 |
| Butylated hydroxytoluene | 0.20 | 0.20 | 0.2 |
| Cab-O-Sil ® | 0.3 | 0.2 | 0.2 |
| Red pigment blend | 0.1 | 0.1 | 0.1 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX ® N80) | 81.0 | 81.0 | 81.0 |
| Povidone (KOLLIDON ® 30 LP) | 8.0 | 8.0 | 8.0 |
| Stearic acid | 0.9 | 0.9 | 0.9 |
| Cab-O-Sil ® | 0.4 | 0.4 | 0.4 |
| Butylated hydroxytoluene | 0.10 | 0.10 | 0.10 |
| Sodium chloride | 10.0 | 10.0 | 10.0 |
| Dehydrated alcohol* | q.s. | q.s. | q.s |
| Push Layer | | | |
| Polyethylene oxide (POLYOX ® WSR 303) | 88.00 | — | — |
| Polyethylene oxide (POLYOX ® WSR 301) | — | 88.0 | — |
| Polyethylene oxide (POLYOX ® WSR Coagulant) | — | — | 88.0 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.50 |
| Butylated hydroxytoluene (BHT) | 0.20 | 0.20 | 0.20 |
| Red pigment blend | 1.5 | 1.5 | 1.5 |
| Cab-O-Sil ® | 0.3 | 0.3 | 0.3 |
| Dehydrated alcohol* | q.s.. | q.s. | q.s. |
| Core Tablet Weight | 385.6 | 385.6 | 385.6 |
| Functional Coating Layer | | | |
| OPADRY ® CA (95:5) | 48.16 | 48.16 | 48.16 |
| Total Weight | 433.76 | 433.76 | 433.76 |

*Removed during process

Tablet 38 contained POLYOX® 1105 in the placebo layer and POLYOX® WSR 303 in the push layer; Tablet 43 contained POLYOX® N750 in the placebo layer and POLYOX® WSR 301 in the push layer; and Tablet 44 contained POLYOX® N80 in the placebo layer and POLYOX® WSR Coagulant in the push layer. Trilayer methylphenidate HCl tablets were made according to the procedure as per Example 6. Tablets 38, 43, and 44 were tested for dissolution in 900 ml of 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 19 shows the effect of POLYOX® grade/average molecular weight in push layer on release rate and drug recovery. The figure compares release rate and drug recovery in compositions containing POLYOX® WSR 303 (7M), POLYOX® WSR 301 (3M), and POLYOX® WSR Coagulant (5M) in push layer. The figure demonstrates that compositions containing POLYOX® N750 in the placebo layer and POLYOX® WSR 301 in the push layer or compositions containing POLYOX® N80 in the placebo layer and POLYOX® WSR Coagulant in the push layer provide higher drug recovery, compared to compositions containing POLYOX® 1105 in the placebo layer and POLYOX® WSR 303 in the push layer.

Example 20

Dissolution in pH 6.8 Buffer, Using USP Apparatus II (Sinkers), Under Low-Volume, Low-RPM (Revolutions Per Minute) Conditions at 37° C.

The present Example provides four different delayed extended release methylphenidate HCl tablet compositions. The components of the different tablets are outlined below in Table 20.

TABLE 20

| Composition | Tablet 45 mg/dose | Tablet 46 mg/dose | Tablet 47 mg/dose | Tablet 48 mg/dose | Tablet 49 mg/dose |
|---|---|---|---|---|---|
| Delayed Extended Release Methylphenidate HCl Tablets | | | | | |
| Placebo Layer | | | | | |
| Polyethylene oxide (POLYOX ® WSR 205) | 100.0 | 100.0 | 80.33 | 80.33 | NA |
| Polyethylene oxide (POLYOX ® WSR 1105) | NA | NA | NA | NA | 100.31 |
| Povidone (KOLLIDON ® 30 LP) | 5.30 | 5.30 | 4.26 | 4.26 | 5.22 |
| Sodium chloride | 7.60 | 7.60 | 6.11 | 6.11 | NA |
| Crospovidone | 7.40 | 7.40 | 5.94 | 5.94 | NA |
| Stearic acid | 1.00 | 1.00 | 0.80 | 0.80 | 1.00 |
| Butylated hydroxytoluene | 0.15 | 0.15 | 0.12 | 0.12 | 0.13 |
| Red pigment blend | 0.05 | 0.05 | 0.04 | 0.04 | 0.07 |
| Cab-O-Sil ® (fumed silica) | 0.50 | 0.50 | 0.40 | 0.40 | 0.27 |
| Dehydrated alcohol* | q.s. | q.s. | q.s. | q.s. | q.s. |
| Active Layer | | | | | |
| Methylphenidate HCl | 54.00 | 54.00 | 54.00 | 54.00 | 54.00 |
| Polyethylene oxide (POLYOX ® N80) | 81.00 | 81.00 | 81.00 | 81.00 | 81.00 |
| Sodium chloride | NA | NA | NA | NA | 10.00 |
| Succinic acid | 10.00 | 6.3 | 6.3 | 6.3 | NA |
| Crospovidone | 6.30 | 6.30 | 6.30 | 6.30 | NA |
| Povidone (KOLLIDON ® 30 LP) | 5.00 | 5.00 | 5.00 | 5.00 | 10.00 |
| Stearic acid | 0.90 | 0.90 | 0.90 | 0.90 | 0.90 |
| Butylated hydroxytoluene | 0.10 | 0.10 | 0.10 | 0.10 | 0.10 |
| Cab-O-Sil ® (fumed silica) | 0.40 | 0.40 | 0.40 | 0.40 | 0.40 |
| Dehydrated alcohol* | q.s. | q.s. | q.s. | q.s. | q.s. |
| Push Layer | | | | | |
| Polyethylene oxide (POLYOX ® WSR 303) | NA | 88.00 | 70.97 | NA | 88.00 |
| Polyethylene oxide (POLYOX ® WSR Coagulant) | 88.00 | NA | NA | 70.97 | NA |
| Sodium chloride | 22.00 | 22.00 | 17.74 | 17.74 | 22.00 |
| Povidone (KOLLIDON ® 30 LP) | 11.50 | 11.50 | 9.28 | 9.28 | 11.50 |
| Stearic acid | 0.50 | 0.50 | 0.40 | 0.40 | 0.50 |
| Butylated hydroxytoluene (BHT) | 0.20 | 0.20 | 0.16 | 0.16 | 0.20 |

TABLE 20-continued

Delayed Extended Release Methylphenidate HCl Tablets

| Composition | Tablet 45 mg/dose | Tablet 46 mg/dose | Tablet 47 mg/dose | Tablet 48 mg/dose | Tablet 49 mg/dose |
|---|---|---|---|---|---|
| Red pigment blend | 1.50 | 1.50 | 1.21 | 1.21 | 1.50 |
| Cab-O-Sil® | 0.30 | 0.30 | 0.24 | 0.24 | 0.30 |
| Dehydrated alcohol* | q.s. | q.s. | q.s. | q.s. | q.s. |
| Total Core Weight | 403.70 | 400.00 | 352.0 | 352.0 | 387.4 |
| Functional Coating Layer | | | | | |
| OPADRY® CA clear (95:5) | | 50.00 | 35.20 | | 48.425 |
| OPADRY® CA clear (90:10) | 40.00 | | | 44.00 | |
| Total Tablet Weight | 443.07 | 450.0 | 387.2 | 396.0 | 435.825 |

*Removed during process

Tablets 45-48 contained sodium chloride and crospovidone, as an osmogen and a wicking agent respectively, in the placebo layer; succinic acid and crospovidone, as a stabilizing agent and an osmogen, respectively, in the active layer; and sodium chloride as an osmogen in the push layer. Tablet 49 did not contain sodium chloride and crospovidone in the placebo layer, and succinic acid and crospovidone in the active layer. The tablets were made according to the following manufacturing procedure.

Manufacturing Procedure

Separate blends of placebo layer, active layer, and push layer were made as per Tablets 55-58.

1. Preparation of placebo blend: Povidone and BHT were added to dehydrated alcohol in a suitable stainless-steel container and mixed to obtain a clear solution; the resulting solution was sprayed onto a blend of polyethylene oxide, sodium chloride, crospovidone, and red pigment blend taken in a high shear mixer; the resulting granules were dried at a temperature of about 40° C. in a forced air oven, and screened through screen #20; the resulting screened granules were taken in a V-blender containing Cab-O-Sil® (pre-screened through screen #30) and mixed for about 5 minutes at 25 RPM, followed by addition of stearic acid and further mixing for 3 minutes.

2. Preparation of active layer blend: Povidone and BHT were added to dehydrated alcohol in a suitable stainless-steel container and mixed to obtain a clear solution; the resulting solution was sprayed onto a blend of methylphenidate HCl, polyethylene oxide, succinic acid, and crospovidone taken in a high shear mixer; the resulting granules were dried at a temperature of about 40° C. in a forced air oven, and screened through screen #20; the resulting screened granules were taken in a V-blender containing Cab-O-Sil® (pre-screened through screen #30) and mixed for about 5 minutes at 25 RPM, followed by addition of stearic acid and further mixing for 3 minutes.

3. Preparation of push layer blend: Povidone and BHT were added to dehydrated alcohol in a suitable stainless-steel container and mixed to obtain a clear solution; the resulting solution was sprayed onto a blend of polyethylene oxide, sodium chloride, and red pigment blend taken in a high shear mixer; the resulting granules were dried at a temperature of about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and further mixing for 3 minutes.

4. Required amount of each blend (as per Tablets 45-48) was filled into the die and then compressed as tri-layer tablet composition, as per Table 20.

5. OPADRY® CA was added to a stainless-steel container charged with acetone and water (about 92:8) and mixed for not less than 60 minutes to obtain a clear solution. The tablets from step #4 were taken in a coating pan and coated with the solution from step #5 until the target % weight gain was obtained and cured at a product temperature of 40° C. for one hour.

6. A hole/orifice of about 0.3 mm was drilled into the coating at the placebo layer end of the tablet.

FIG. 20 provides dissolution profiles of Tablets 45, 48, and 49 in 5 ml of pH 6.8 buffer, using USP Apparatus II (Sinkers), at 5 rpm and 37° C. (low-volume, low-RPM condition). Percentage dissolution of the tablets was measured at 2, 4, 6, 8, 10, 12, 14, 16, 18, 20, 22, and 24 hours. FIG. 20 demonstrates that Tablet 45, with about 10% coating weight gain, based on the total weight of the uncoated tablet core, provides an improved release rate and improved drug recovery compared to Tablets 48 and 49, with about 12.5% coating weight gain, based on the total weight of the uncoated tablet core. FIG. 20 further demonstrates that Tablets 45 and 48 containing higher amount of pore former (Polyethylene glycol present in OPADRY® CA clear (90:10)) in the coating layer provide faster drug release compared to Tablet 49 containing less amount of pore former in OPADRY® CA clear (95:5) in the coating layer. FIG. 20 also demonstrates that Tablet 49 containing POLYOX® 1105 in the placebo layer and POLYOX® WSR 303 in the push layer provides longer lag time compared to Tablets 45 and 48 containing POLYOX® 205 in placebo layer and POLYOX® WSR coagulant in the push layer.

Example 21

Oral Bioavailability of Methylphenidate HCl from Osmotic-Controlled Compositions of the Disclosure A single dose pharmacokinetic (PK) study was conducted in healthy volunteers under fed conditions to evaluate and compare the PK performance of delayed extended release methylphenidate HCl compositions of the present disclosure with a marketed extended release methylphenidate HCl product (CONCERTA®). An open label, balanced, randomized, three-treatment, six-sequence three-period, single oral dose, three-way crossover bioequivalence study of Tablets 45 and 48 with CONCERTA® (methylphenidate hydrochloride extended-release tablets), 54 mg, was conducted in normal, healthy, adult, human subjects under fed conditions.

TABLE 21

Pharmacokinetic Results of Methylphenidate HCl

| Pharmacokinetic Parameters (units) | Mean ± SD (CV %) (N = 18) | | |
|---|---|---|---|
| | Tablet 45 | Tablet 48 | Reference Product (54 mg) |
| Cmax | 22.0 (44) | 17.4 (36) | 21.0 (35.6) |
| Tmax | 12.0 (15.6) | 14.2 (23) | 9.1 (19.5) |
| AUC0-∞ | 219.0 (51) | 222.0 (40) | 296.0 (38) |

The data demonstrates that $C_{max}$ of Tablet 45 is comparable to the $C_{max}$ of the marketed extended release product. The data from this study (Table 21/FIG. 21) demonstrates that Tablet 45 provides a lag time of about 7 hours and $C_{max}$ of about 22 ng at 12 hours post administration.

Example 22

Dissolution in pH 6.8 Buffer, Using USP Apparatus II (Sinkers), Under Low-Volume, Low-RPM (Revolutions Per Minute) Conditions at 37° C.

The present Example provides four different delayed extended release methylphenidate HCl tablet compositions. The components of the different tablets are outlined below in Table 22.

TABLE 22

Delayed Extended Release Methylphenidate HCl Tablets

| Composition | Tablet 45 mg/dose | Tablet 50A mg/dose | Tablet 50B mg/dose | Tablet 50C mg/dose |
|---|---|---|---|---|
| Placebo Layer | | | | |
| Granulation Solvent | Alcohol 100% | Alcohol:water (90:10) | Alcohol:water (90:10) | Alcohol:water (90:10) |
| Polyethylene oxide (POLYOX® WSR 205) | | 123.00 | 123.00 | 123.00 |
| Polyethylene oxide (POLYOX® WSR 1105) | 100.0 | | | |
| Povidone (KOLLIDON® 30 LP) | 5.22 | 6.52 | 6.52 | 6.52 |
| Sodium chloride | 7.60 | 18.45 | 18.45 | 18.45 |
| Crospovidone | 7.40 | NA | NA | NA |
| Stearic acid | 1.00 | 1.23 | 1.23 | 1.23 |
| Butylated hydroxytoluene | 0.13 | 0.18 | 0.18 | 0.18 |
| Red pigment blend | 0.07 | 0.06 | 0.06 | 0.06 |
| Cab-O-Sil® (fumed silica) | 0.27 | 0.62 | 0.62 | 0.62 |
| Active Layer | | | | |
| Granulation Solvent | Alcohol 100% | Alcohol:water (70:30) | Alcohol:water (70:30) | Alcohol:water (70:30) |
| Methylphenidate HCl | 54.00 | 54.00 | 54.00 | 54.00 |
| Polyethylene oxide (POLYOX® N80) | 81.00 | 81.00 | 81.00 | 81.00 |
| Sodium chloride | 10.00 | NA | NA | NA |
| Succinic acid | NA | 10.00 | 10.00 | 10.00 |
| Crospovidone | NA | 6.30 | 6.30 | 6.30 |
| Povidone (KOLLIDON® 30 LP) | 10.00 | 5.00 | 5.00 | 5.00 |
| Stearic acid | 0.90 | 0.90 | 0.90 | 0.90 |
| Butylated hydroxytoluene | 0.10 | 0.10 | 0.10 | 0.10 |
| Cab-O-Sil® (fumed silica) | 0.40 | 0.40 | 0.40 | 0.40 |
| Push Layer | | | | |
| Polyethylene oxide (POLYOX® WSR 303) | 88.00 | | | |
| Polyethylene oxide (POLYOX® WSR Coagulant) | | 88.00 | 88.00 | 88.00 |
| Sodium chloride | 22.00 | 22.00 | 22.00 | 22.00 |
| Povidone (KOLLIDON® 30 LP) | 11.50 | 11.50 | 11.50 | 11.50 |
| Stearic acid | 0.50 | 0.50 | 0.50 | 0.50 |
| Butylated hydroxytoluene (BHT) | 0.20 | 0.20 | 0.20 | 0.20 |

TABLE 22-continued

Delayed Extended Release Methylphenidate HCl Tablets

| Composition | Tablet 45 mg/dose | Tablet 50A mg/dose | Tablet 50B mg/dose | Tablet 50C mg/dose |
|---|---|---|---|---|
| Red pigment blend | 1.50 | 1.50 | 1.50 | 1.50 |
| Cab-O-Sil ® | 0.30 | 0.40 | 0.40 | 0.40 |
| Total Core Weight | 387.4 | 431.86 | 431.86 | 431.86 |
| Functional Coating Layer | | | | |
| OPADRY ® CA clear (90:10) | | 42.80 | 53.50 | 42.8 |
| OPADRY ® CA clear (95:5) | 48.13 | | | |
| Orifice Size | | 0.6 mm x1 | 0.6 mm x2 | 1.2 mm x1 |
| Total Weight | 435.53 | 474.66 | 485.36 | 474.66 |

*Removed during process

Tablet 50A contained a coating with 10% coating weight gain and one orifice with about 0.6 mm diameter; Tablet 50B contained a coating with 12.5% coating weight gain and two orifices, each with 0.6 mm diameter; and Tablet 50C contained a coating with 10% coating weight gain and one orifice with 1.2 mm diameter. Tablet 45 contained about 32 wt % of placebo layer, based on the total weight of the uncoated tablet core; Tablets 50A, 50B, and 50C contained about 35 wt % of placebo layer, based on the total weight of the uncoated tablet core. Trilayer methylphenidate HCl tablets were made by following the procedure as outlined Example 20. FIG. 22 provides dissolution profiles of Tablets 45, 50 A, 50B, and 50C in 900 ml of 0.01N HCl, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 22 demonstrates that drug recovery increases with increasing size of the orifice, at a similar coating weight gain. FIG. 22 further demonstrates that Tablet 50B at about 12.5% coating weight gain and containing 2 orifices provided similar recovery compared to Tablet 50A with about 10% coating weight gain and containing one orifice, i.e., the reduction in drug recovery with increased coating weight gain was minimized with the presence of two orifices in the coating with higher coating weight gain. FIG. 22 further demonstrates that lag time increases from about 5 hours to about 6 hours with increasing placebo layer amount from about 32 wt % to about 35 wt %, based on the total weight of the uncoated tablet core.

Example 23

Effect of Granulation Solvent in Placebo Layer on Dissolution Profile

The present Example provides four different delayed extended release methylphenidate HCl tablet compositions. The components of the different tablets are outlined below in Table 23.

TABLE 23

Delayed Extended Release Methylphenidate HCl Tablets

| Composition | Tablet 51A mg/dose | Tablet 51B mg/dose | Tablet 52A mg/dose | Tablet 52B mg/dose |
|---|---|---|---|---|
| Placebo Layer | | | | |
| Granulation Solvent | Alcohol 100% | Alcohol 100% | Alcohol:water (90:10) | Alcohol:water (90:10) |
| Polyethylene oxide (POLYOX ® WSR 205) | 100.00 | 100.00 | 100.00 | 100.00 |
| Povidone (KOLLIDON ® 30 LP) | 5.30 | 5.30 | 5.30 | 5.30 |
| Sodium chloride | 15.00 | 15.00 | 15.00 | 15.00 |
| Stearic acid | 1.00 | 1.00 | 1.00 | 1.00 |
| Butylated hydroxytoluene | 0.15 | 0.15 | 0.15 | 0.15 |
| Red pigment blend | 0.05 | 0.05 | 0.05 | 0.05 |
| Cab-O-Sil ® (fumed silica) | 0.50 | 0.50 | 0.50 | 0.50 |
| Active Layer | | | | |
| Granulation Solvent | Alcohol:water (70:30) | Alcohol:water (70:30) | Alcohol:water (70:30) | Alcohol:water (70:30) |
| Methylphenidate HCl | 54.00 | 54.00 | 54.00 | 54.00 |
| Polyethylene oxide (POLYOX ® N80) | 81.00 | 81.00 | 81.00 | 81.00 |
| Succinic acid | 10.00 | 10.00 | 10.00 | 10.00 |
| Crospovidone | 6.30 | 6.30 | 6.30 | 6.30 |
| Povidone (KOLLIDON ® 30 LP) | 5.00 | 5.00 | 5.00 | 5.00 |

TABLE 23-continued

Delayed Extended Release Methylphenidate HCl Tablets

| Composition | Tablet 51A mg/dose | Tablet 51B mg/dose | Tablet 52A mg/dose | Tablet 52B mg/dose |
|---|---|---|---|---|
| Stearic acid | 0.90 | 0.90 | 0.90 | 0.90 |
| Butylated hydroxytoluene | 0.10 | 0.10 | 0.10 | 0.10 |
| Cab-O-Sil ® (fumed silica) | 0.40 | 0.40 | 0.40 | 0.40 |
| Push Layer | | | | |
| Polyethylene oxide (POLYOX ® WSR Coagulant) | 88.00 | 88.00 | 88.00 | 88.00 |
| Sodium chloride | 22.00 | 22.00 | 22.00 | 22.00 |
| Povidone (KOLLIDON ® 30 LP) | 11.50 | 11.50 | 11.50 | 11.50 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.50 | 1.50 | 1.50 | 1.50 |
| Cab-O-Sil ® | 0.30 | 0.40 | 0.40 | 0.40 |
| Total Core Weight | 403.80 | 403.80 | 403.80 | 403.80 |
| Functional Coating Layer | | | | |
| OPADRY ® CA clear (90:10) | 40.00 | 50.00 | 40.00 | 50.00 |
| Orifice Size | 0.6 mm | 0.6 mm | 0.6 mm | 0.6 mm |
| Total Tablet Weight | 443.80 | 453.80 | 443.80 | 453.80 |

*Removed during process

Placebo layer granules in Tablet 51A and Tablet 51B were made using 100% alcohol as the granulating solvent. Placebo layer granules in Tablet 52A and 52B were made using a mixture of alcohol and water as the granulating solvent. Trilayer methylphenidate HCl tablets were made according to the procedure as per Example 20. FIG. 23 provides dissolution profiles of Tablets 45, 51A, 51B, 52A, and 52B in 900 ml of 0.01N HCl, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 23 demonstrates that granulation solvent does not have significant effect on release profile and lag time of the composition.

Example 24

Effect of the Average Molecular Weight of POLYOX Present in Placebo Layer on Release Profile of the Composition The present Example provides four different delayed extended release methylphenidate HCl tablet compositions. The components of the different tablets are outlined below in Table 24.

TABLE 24

Delayed Extended Release Methylphenidate HCl Tablets

| Composition | Tablet 53A mg/dose | Tablet 53B mg/dose | Tablet 52A mg/dose | Tablet 52B mg/dose |
|---|---|---|---|---|
| Placebo Layer | | | | |
| Granulation Solvent | Alcohol:water (90:10) | Alcohol:water (90:10) | Alcohol:water (90:10) | Alcohol:water (90:10) |
| Polyethylene oxide (POLYOX ® WSR 205) | | | 100.00 | 100.00 |
| Polyethylene oxide (POLYOX ® WSR 1105) | 100.00 | 100.00 | | |
| Povidone (KOLLIDON ® 30 LP) | 5.30 | 5.30 | 5.30 | 5.30 |
| Sodium chloride | 15.00 | 15.00 | 15.00 | 15.00 |
| Stearic acid | 1.00 | 1.00 | 1.00 | 1.00 |
| Butylated hydroxytoluene | 0.15 | 0.15 | 0.15 | 0.15 |
| Red pigment blend | 0.05 | 0.05 | 0.05 | 0.05 |
| Cab-O-Sil ® (fumed silica) | 0.50 | 0.50 | 0.50 | 0.50 |

TABLE 24-continued

Delayed Extended Release Methylphenidate HCl Tablets

| Composition | Tablet 53A mg/dose | Tablet 53B mg/dose | Tablet 52A mg/dose | Tablet 52B mg/dose |
|---|---|---|---|---|
| Active Layer | | | | |
| Granulation Solvent | Alcohol:water (70:30) | Alcohol:water (70:30) | Alcohol:water (70:30) | Alcohol:water (70:30) |
| Methylphenidate HCl | 54.00 | 54.00 | 54.00 | 54.00 |
| Polyethylene oxide (POLYOX ® N80) | 81.00 | 81.00 | 81.00 | 81.00 |
| Succinic acid | 10.00 | 10.00 | 10.00 | 10.00 |
| Crospovidone | 6.30 | 6.30 | 6.30 | 6.30 |
| Povidone (KOLLIDON ® 30 LP) | 5.00 | 5.00 | 5.00 | 5.00 |
| Stearic acid | 0.90 | 0.90 | 0.90 | 0.90 |
| Butylated hydroxytoluene | 0.10 | 0.10 | 0.10 | 0.10 |
| Cab-O-Sil ® (fumed silica) | 0.40 | 0.40 | 0.40 | 0.40 |
| Push Layer | | | | |
| Polyethylene oxide (POLYOX ® WSR Coagulant) | 88.00 | 88.00 | 88.00 | 88.00 |
| Sodium chloride | 22.00 | 22.00 | 22.00 | 22.00 |
| Povidone (KOLLIDON ® 30 LP) | 11.50 | 11.50 | 11.50 | 11.50 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.50 | 1.50 | 1.50 | 1.50 |
| Cab-O-Sil ® | 0.30 | 0.40 | 0.40 | 0.40 |
| Total Core Weight | 403.70 | 403.70 | 403.70 | 403.70 |
| Functional Coating Layer | | | | |
| OPADRY ® CA clear (90:10) | 40.00 | 50.00 | 40.00 | 50.00 |
| Orifice Size | 0.6 mm | 0.6 mm | 0.6 mm | 0.6 mm |
| Total Tablet Weight | 444.07 | 453.70 | 440.70 | 453.70 |

*Removed during process

Placebo layer granules in Tablet 52A and Tablet 52B contained POLYOX® WSR 205. Placebo layer granules in Tablet 53A and 53B contained POLYOX® WSR 1105. Trilayer methylphenidate HCl tablets were made by following the procedure as outlined in Example 20. FIG. 24 provides dissolution profiles of Tablets 45, 52A, 52B, 53A, and 53B.in 900 ml of 0.01N HCl, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 24 demonstrates that average molecular weight of POLYOX® present in the placebo layer does not have significant effect on release profile and lag time.

Example 25

Effect of the Amount of POLYOX Present in Placebo Layer on Release Profile of the Composition Dissolution profiles of Tablets 45, 50A, 50B, 52A, and 52B.were determined in 900 ml of 0.01N HCl, using USP Apparatus II (Sinkers), at 50 rpm and 37° C. FIG. 25 shows percentage dissolution of the tablets as measured at 2, 4, 6, 8, 10, 12, 14, 16, 18, 20, 22, and 24 hours. FIG. 25 demonstrates that the amount of POLYOX® present in the placebo layer does not have significant effect on release profile and lag time.

Example 26

Dissolution Profiles of Delayed Extended Release Methylphenidate HCl Compositions of the Disclosure in Low-Volume, Low-RPM Conditions The present example provides for dissolution profiles of delayed extended release methylphenidate HCl compositions of the disclosure in low-volume, low-RPM conditions. Compositions of each of the tablets tested are shown in Table 25 and Table 26.

TABLE 25

Delayed Extended Release Methylphenidate HCl Tablets

| Composition | Tablet 54A mg/dose | Tablet 55A mg/dose | Tablet 56 mg/dose | Tablet 57 mg/dose |
|---|---|---|---|---|
| Placebo Layer | | | | |
| Granulation Solvent | Alcohol:water (90:10) | Alcohol:water (90:10) | Alcohol:water (90:10) | Alcohol:water (90:10) |
| Polyethylene oxide (POLYOX ® WSR 205) | 164.00 | 164.00 | 100.00 | 100.00 |
| Povidone (KOLLIDON ® 30 LP) | 8.50 | 8.50 | 5.30 | 5.30 |
| Sodium chloride | 25.00 | 25.00 | 15.00 | 15.00 |
| Stearic acid | 1.50 | 1.50 | 1.00 | 1.00 |
| Butylated hydroxytoluene | 0.25 | 0.25 | 0.15 | 0.15 |
| Red pigment blend | 0.10 | 0.10 | 0.05 | 0.05 |
| Cab-O-Sil ® (fumed silica) | 0.75 | 0.75 | 0.50 | 0.50 |
| Active Layer | | | | |
| Granulation Solvent | Alcohol:water (70:30) | Alcohol:water (70:30) | Alcohol:water (70:30) | Alcohol:water (70:30) |
| Methylphenidate HCl | 54.00 | 54.00 | 54.00 | 54.00 |
| Polyethylene oxide (POLYOX ® N80) | 81.00 | 33.67 | 60.00 | 81.00 |
| Succinic acid | 10.00 | 4.09 | 5.32 | 10.00 |
| Crospovidone | 6.30 | 4.09 | 5.32 | 6.30 |
| Povidone (KOLLIDON ® 30 LP) | 5.00 | 3.25 | 4.23 | 5.00 |
| Stearic acid | 0.90 | 0.58 | 0.75 | 0.90 |
| Butylated hydroxytoluene | 0.10 | 0.06 | 0.08 | 0.10 |
| Cab-O-Sil ® (fumed silica) | 0.40 | 0.26 | 0.34 | 0.40 |
| Push Layer | | | | |
| Polyethylene oxide (POLYOX ® WSR Coagulant) | 88.00 | 88.00 | 71.00 | NA |
| Polyethylene oxide (POLYOX ® WSR 303) | | | | 88.00 |
| Sodium chloride | 22.00 | 22.00 | 17.7 | 22.00 |
| Povidone (KOLLIDON ® 30 LP) | 11.50 | 11.50 | 9.3 | 11.50 |
| Stearic acid | 0.50 | 0.50 | 0.40 | 0.50 |
| Butylated hydroxytoluene (BHT) | 0.20 | 0.20 | 0.20 | 0.20 |
| Red pigment blend | 1.50 | 1.50 | 1.20 | 1.50 |
| Cab-O-Sil ® | 0.30 | 0.30 | 0.20 | 0.30 |
| Total Core Weight | 481.80 | 424.10 | 352.04 | 403.7 |
| Functional Coating Layer | | | | |
| OPADRY ® CA clear (90:10) | 48.18 | 42.41 | 35.20 | 40.37 |
| Total Tablet Weight | 529.98 | 466.51 | 387.24 | 444.07 |

*Removed during process

TABLE 26

| Composition | Tablet 54B mg/dose | Tablet 55B mg/dose |
|---|---|---|
| Placebo Layer | | |
| Granulation Solvent | Alcohol:water (90:10) | Alcohol:water (90:10) |
| Polyethylene oxide (POLYOX ® WSR 205) | 164.00 | 164.00 |
| Povidone (KOLLIDON ® 30 LP) | 8.50 | 8.50 |
| Sodium chloride | 25.00 | 25.00 |
| Stearic acid | 1.50 | 1.50 |
| Butylated hydroxytoluene | 0.25 | 0.25 |
| Red pigment blend | 0.10 | 0.10 |
| Cab-O-Sil ® (fumed silica) | 0.75 | 0.75 |
| Active Layer | | |
| Granulation Solvent | Alcohol:water (70:30) | Alcohol:water (70:30) |
| Methylphenidate HCl | 54.00 | 54.00 |
| Polyethylene oxide (POLYOX ® N80) | 81.00 | 33.67 |

TABLE 26-continued

| Composition | Tablet 54B mg/dose | Tablet 55B mg/dose |
| --- | --- | --- |
| Succinic acid | 10.00 | 4.09 |
| Crospovidone | 6.30 | 4.09 |
| Povidone (KOLLIDON ® 30 LP) | 5.00 | 3.25 |
| Stearic acid | 0.90 | 0.58 |
| Butylated hydroxytoluene | 0.10 | 0.06 |
| Cab-O-Sil ® (fumed silica) | 0.40 | 0.26 |
| Push Layer | | |
| Polyethylene oxide (POLYOX ® WSR Coagulant) | 88.00 | 88.00 |
| Polyethylene oxide (POLYOX ® WSR 303) | | |
| Sodium chloride | 22.00 | 22.00 |
| Povidone (KOLLIDON ® 30 LP) | 11.50 | 11.50 |
| Stearic acid | 0.50 | 0.50 |
| Butylated hydroxytoluene (BHT) | 0.20 | 0.20 |
| Red pigment blend | 1.50 | 1.50 |
| Cab-O-Sil ® | 0.30 | 0.30 |
| Total Core Weight | 481.80 | 424.10 |
| Functional Coating Layer | | |
| OPADRY ® CA clear (90:10) | 57.81 | 50.892 |
| Total Tablet Weight | 539.60 | 474.992 |

*Removed during process

Placebo layer granules and active layer granules in Tablet 45 were made using dehydrated alcohol as the granulation solvent. Placebo layer granules and active layer granules in Tablets 54A, 54B, 55A, and 55B were made using a mixture of alcohol and water as the granulation solvent. Tablets 45 and 54A, 54B, and 57 contained a drug: polymer weight ratio in the active layer of about 40:60; Tablets 55A and 55B contained a drug: polymer weight ratio in the active layer of about 60:40; and Tablet 56 contained a drug: polymer weight ratio in the active layer of about 50:50. Tablet 45 contained 122 mg of placebo layer (about 32 wt % of the placebo layer, based on the total weight of the uncoated tablet core) and Tablet 54 contained 196 mg of placebo layer (about 42 wt % of placebo layer, based on the total weight of the uncoated tablet core). Trilayer methylphenidate HCl tablets were made by following the procedure as outlined in Example 20. FIG. 26 provides dissolution profiles of Tablets 45, 54A, 54B, 55A, and 55B in 50 ml of pH 6.8 buffer, using USP Apparatus II (Sinkers), at 5 rpm and 37° C.". Percentage dissolution of the tablets was measured at 2, 4, 6, 8, 10, 12, 14, 16, 18, 20, 22, and 24 hours. FIG. 26 demonstrates that amount of POLYOX® present in the active layer, and granulation medium for making active layer granules and placebo layer granules affects lag time. FIG. 26 further demonstrates that the drug: polymer weight ratio affects the release rate, e.g., compositions with higher drug: polymer weight ratio provide faster release rate compared to compositions with lower drug: polymer weight ratio. FIG. 26 further demonstrates that lag time increases with increasing weight % of the placebo layer, based on the total weight of the uncoated tablet core e.g., Tablet 54 exhibits higher lag time compared to Tablet 45.

FIG. 27 provides dissolution profiles of Tablets 45, 55A with one 0.6 mm diameter orifice, Tablet 55A with two 0.6 mm diameter orifices, and Tablet 55A with placebo layer top diameter orifice, in 50 ml of pH 6.8 buffer, using USP Apparatus II (Sinkers), at 5 rpm and 37° C. Percentage dissolution of the tablets was measured at 2, 4, 6, 8, 10, 12, 14, 16, 18, 20, 22, and 24 hours.

Example 27

Effect of the Number of Orifices on the Placebo Layer End of the Functional Coated Tablets on % Variability (Relative Standard Deviation)

Table 27 provides dissolution data of functional coated methylphenidate hydrochloride tablets with % relative standard deviation (% RSD) for Tablet 45A containing a functional coating with one orifice with 0.6 mm diameter; Tablet 45B containing a functional coating with two orifices, each with 0.6 mm diameter; and Tablet 45C containing a functional coating with one orifice with 1.2 mm diameter. The tablets were tested for dissolution in 900 ml of 0.01N HCl for up to 24 hours, using USP Apparatus II (Sinkers), at 50 rpm and 37° C. The % RSD was determined based on dissolution data for a set of three tablets each, for Tablets 45A, 45B, and 45C, at different time points. The table shows that Tablet 45B containing two orifices, each with 0.6 mm diameter; and Tablet 45C containing one orifice with 1.2 mm diameter show significantly reduced % RSD among a set of three tablets, compared to Tablet 45A containing one orifice with 0.6 mm diameter.

TABLE 27

| | Tablet 45A (10% coat-0.6 mm, 1 hole) | | Tablet 45B (10% coat-0.6 mm, 2 holes) | | Tablet 45C (10% coat-1.2 mm, 1 hole) | |
| --- | --- | --- | --- | --- | --- | --- |
| Time (hrs) | % Dissolved | % RSD | % Dissolved | % RSD | % Dissolved | % RSD |
| 0 | 0.0 | 0.0 | 0.0 | 0.0 | 0.0 | 0.0 |
| 6 | 12.0 | 43.1 | 10.0 | 21.5 | 10.0 | 14.8 |
| 7 | 21.0 | 19.6 | 24.0 | 15.0 | 24.0 | 29.2 |
| 8 | 33.0 | 30.2 | 44.0 | 13.0 | 41.0 | 25.7 |
| 9 | 48.0 | 36.3 | 65.0 | 11.5 | 58.0 | 18.9 |
| 10 | 63.0 | 30.2 | 82.0 | 8.5 | 73.0 | 11.7 |
| 12 | 82.0 | 14.1 | 97.0 | 4.6 | 90.0 | 3.2 |

The present disclosure is not to be limited in scope by the specific embodiments described herein. Indeed, various modifications of the disclosure in addition to those described herein will become apparent to those skilled in the art from the foregoing description. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

Patents, patent applications, publications, product descriptions, and protocols are cited throughout this application, the disclosures of which are incorporated herein by reference in their entireties for all purposes.

The invention claimed is:

1. An osmotic-controlled oral pharmaceutical composition providing delayed release of a therapeutically effective amount of methylphenidate or a pharmaceutically acceptable salt thereof, the composition comprising:
   a) a multilayered core comprising a placebo layer, an active layer, and a push layer, wherein:
      (i) the placebo layer comprises at least one polyethylene oxide polymer having an average molecular weight of from about 600,000 Da to about 900,000 Da,
      (ii) the active layer comprises methylphenidate or a pharmaceutically acceptable salt thereof, and at least one polyethylene oxide polymer having an average molecular weight of from about 100,000 Da to about 300,000 Da,
      (iii) the push layer comprises at least one polyethylene oxide polymer having an average molecular weight of greater than or equal to 1000,000 Da, and at least one osmogen; and
   b) a semipermeable membrane comprising at least one orifice and surrounding the core,
   wherein the layers in the multilayer core are placed in the following order: the placebo layer in fluid communication with the orifice in the semipermeable membrane; the active layer; and the push layer facing away from the orifice.

2. The composition of claim 1, wherein the semipermeable membrane comprises a water-insoluble polymer and a pore former.

3. The composition of claim 2, wherein the water-insoluble polymer and the pore former are present in a polymer to pore former ratio of between about 80:20 and about 99.5:0.5.

4. The composition of claim 2, wherein the water-insoluble polymer in the semipermeable membrane comprises polymers selected from the group consisting of cellulose acetate, cellulose diacetate, cellulose triacetate, cellulose propionate, cellulose acetate butyrate, and combinations thereof.

5. The composition of claim 2, wherein the pore former is selected from the group consisting of polyethylene glycol, hydroxypropyl cellulose, polyvinyl pyrrolidone sucrose, glucose, fructose, lactose, mannose, mannitol, sorbitol, methyl cellulose, poloxamers, triethyl citrate, triacetin, hydroxypropyl methylcellulose, glycerol, and combinations thereof.

6. The composition of claim 2, wherein the semipermeable membrane further comprises at least one plasticizer selected from the group consisting of polyethylene glycols, triethyl citrate, triacetin, diethyl tartrate, dibutyl sebacate, and combinations thereof.

7. The composition of claim 1, wherein the polyethylene oxide polymer in the placebo layer has an average molecular weight of about 600,000 Da or about 900,000 Da, and the polyethylene oxide polymer in the active layer has an average molecular weight of about 200,000 Da.

8. The composition of claim 1, wherein any of the placebo layer, the active layer, and the push layer further comprise a binder, a stabilizer, and/or a lubricant.

9. The composition of claim 1, wherein the polyethylene oxide polymer in the push layer has an average molecular weight of about 1000,000 Da, about 2000,000 Da, about 4000,000 Da, about 5000,000 Da, about 7000,000 Da, or intermediate values therein.

10. The composition of claim 1, wherein the osmogen in the push layer is selected from the group consisting of sodium chloride, potassium chloride, potassium sulfate, lithium sulfate, sodium sulfate, lactose, dextrose, sucrose, mannitol, fructose, sorbitol, xylitol, dibasic sodium phosphate, and combinations thereof.

11. The composition of claim 1, wherein the osmogen in the push layer is present in an amount of between about 5 wt % and about 40 wt %, based on the total weight of the push layer.

12. The composition of claim 1, wherein the semipermeable membrane is applied at a coating weight gain of about 1 wt % to 50 wt %, based on the total weight of the uncoated tablet core.

13. The composition of claim 1, wherein the composition provides a lag time of at least about 6 hours, during which the composition releases no more than 10 wt % of the methylphenidate or a pharmaceutically acceptable salt thereof, measured in 900 ml of 0.01N HCl, using USP II (sinkers) at 50 rpm and 37° C.

14. The composition of claim 1, wherein the composition further comprises an immediate release layer containing a sedative and placed over the semipermeable membrane.

15. The composition of claim 14, wherein the sedative is selected from the group consisting of clonidine, guanfacine, diphenhydramine, melatonin, and pharmaceutically acceptable salts thereof.

16. A method for treating attention deficit hyperactivity disorder (ADHD) in a subject, the method comprising orally administering to the subject an osmotic-controlled oral pharmaceutical composition providing delayed release of methylphenidate or a pharmaceutically acceptable salt thereof, the composition comprising:
   a) a multilayered core comprising a placebo layer, an active layer, and a push layer, wherein:
      (i) the placebo layer comprises at least one polyethylene oxide polymer having an average molecular weight of from about 600,000 Da to about 900,000 Da,
      (ii) the active layer comprises methylphenidate or a pharmaceutically acceptable salt thereof, and at least one polyethylene oxide polymer having an average molecular weight of from about 100,000 Da to about 300,000 Da,
      (iii) the push layer comprises at least one polyethylene oxide polymer having an average molecular weight of greater than or equal to 1000,000 Da, and at least one osmogen, and
   b) a semipermeable membrane, comprising at least one orifice and surrounding the core,
   wherein the layers in the multilayer core are placed in the following order: the placebo layer in fluid communication with the orifice in the semipermeable membrane; the active layer; and the push layer facing away from the orifice.

17. A method for treating attention deficit hyperactivity disorder in a subject, the method comprising orally administering to the subject, in the night before bedtime, an osmotic-controlled oral pharmaceutical composition providing delayed release of methylphenidate or a pharmaceutically acceptable salt thereof,
   wherein the composition comprises:
   a) a multilayered core comprising a placebo layer, an active layer, and a push layer, wherein:
      (i) the placebo layer comprises at least one polyethylene oxide polymer having an average molecular weight of from about 600,000 Da to about 900,000 Da, (ii) the active layer comprises methylphenidate or a pharmaceutically acceptable salt thereof, and at least one polyethylene oxide polymer having an average molecular weight of from about 100,000 Da to about 300,000 Da, (iii) the push layer comprises at least one polyethylene oxide polymer having an average molecular weight of greater than or equal to 1000,000 Da, and at least one osmogen, and b) a semipermeable membrane comprising at least one orifice and surrounding the core, wherein the layers in the multilayer core are placed in the following order: the placebo layer in fluid communication with the orifice in the semipermeable membrane; the active layer; and the push layer facing away from the orifice, wherein the composition provides a therapeutic amount of methylphenidate throughout the following day.

18. A method for making an osmotic-controlled oral pharmaceutical composition providing delayed release of methylphenidate or a pharmaceutically acceptable salt thereof, the method comprising:

i) making placebo layer blend comprising at least one polyethylene oxide polymer having an average molecular weight of from about 600,000 Da to about 900,000 Da;

ii) making an active layer blend comprising methylphenidate or a pharmaceutically acceptable salt thereof, and at least one polyethylene oxide polymer having an average molecular weight of from about 100,000 Da to about 300,000 Da;

iii) making a push layer blend comprising at least one polyethylene oxide polymer having an average molecular weight of greater than or equal to 1000,000 Da, and at least one osmogen;

iv) filling the placebo layer blend, the active layer blend, and the push layer blend into a tablet dye and compressing into a trilayer tablet core;

v) coating the trilayer tablet core with a semipermeable membrane coat comprising a water-insoluble polymer and a pore former at a polymer to pore former ratio of between about 80:20 and about 99.5:0.5; and vi) drilling of an orifice in the semipermeable membrane coating.

* * * * *